(12) United States Patent
Shinkura

(10) Patent No.: US 9,765,151 B2
(45) Date of Patent: Sep. 19, 2017

(54) METHOD FOR PRODUCING MONOCLONAL IGA ANTIBODY

(71) Applicant: CURED INC., Yokohama-shi, Kanagawa (JP)

(72) Inventor: Reiko Shinkura, Shiga (JP)

(73) Assignee: CURED INC., Yokohama-Shi, Kanagawa (JP)

( * ) Notice: Subject to any disclaimer, the term of this patent is extended or adjusted under 35 U.S.C. 154(b) by 105 days.

(21) Appl. No.: 14/773,923

(22) PCT Filed: Mar. 10, 2014

(86) PCT No.: PCT/JP2014/056216
§ 371 (c)(1),
(2) Date: Oct. 16, 2015

(87) PCT Pub. No.: WO2014/142084
PCT Pub. Date: Sep. 18, 2014

(65) Prior Publication Data
US 2016/0039944 A1 Feb. 11, 2016

(30) Foreign Application Priority Data

Mar. 11, 2013 (JP) ................ 2013-048365
Aug. 9, 2013 (JP) ................ 2013-167120

(51) Int. Cl.
| | |
|---|---|
| C12N 15/09 | (2006.01) |
| A61K 39/395 | (2006.01) |
| C07K 16/40 | (2006.01) |
| C07K 16/12 | (2006.01) |
| A61K 39/00 | (2006.01) |

(52) U.S. Cl.
CPC .......... *C07K 16/40* (2013.01); *C07K 16/1228* (2013.01); *A61K 2039/505* (2013.01); *C07K 2317/34* (2013.01)

(58) Field of Classification Search
None
See application file for complete search history.

(56) References Cited

FOREIGN PATENT DOCUMENTS

CN 1381567 A 11/2002

OTHER PUBLICATIONS

Reiko Shinkura, "Isolation of intestinal IgA antibodies effective for intestinal flora control and their application", Yakult Bio-Science Foundation Nenpo, Sep. 30, 2013, No. 21, pp. 32-40 (26 total pages with English translation).
Reiko Shinkura, "Chonai Flora Seigyo ni Yuko na Chokan IgA Kotai no Bunri", Yakult Bio-Science Foundation Nenpo, Jan. 31, 2013, No. 20, pp. 50-57 (and English translation thereof).
Min Wei et al., "Mice carrying a knock-in mutation of Aicda resulting in a defect in somatic hypermutation have impaired gut homeostasis and compromised mucosal defense", Nature Immunology, Mar. 2011, vol. 12, No. 3, pp. 264-270.
Reiko Shinkura, "Chonai Flora Seigyo ni Yuko na Chokan IgA Kotai no Bunri to sono Oyo", Yakult Bio-Science Foundation Nenpo, Sep. 30, 2013, No. 21, pp. 32-40.
Cerf-Bensussan et al., "The immune system and the gut microbiota: friends or foes?", Nature Reviews Immunology, Oct. 2010, vol. 10, pp. 735-744.
Hooper et al., "Immune adaptations that maintain homeostasis with the intestinal microbiota", Nature Reviews Immunology, Mar. 2010, vol. 10, pp. 159-169.
Round et al., "Inducible Foxp3+ regulatory T-cell development by a commensal bacterium of the intestinal microbiota", Proceedings of the National Academy of Sciences of United States of America, Jul. 6, 2010, vol. 107, No. 27, pp. 12204-12209.
Vijay-Kumar et al., "Metabolic Syndrome and Altered Gut Microbiota in Mice Lacking Toll-Like Receptor 5", Science, 2010, vol. 328, pp. 228-231.
Shulzhenko et al., "Crosstalk between B lymphocytes, microbiota and the intestinal epithelium governs immunity versus metabolism in the gut", Nature Medicine, Dec. 2011, vol. 17, No. 12, pp. 1585-1593.
Bry et al., "A Model of Host-Microbial Interactions in an Open Mammalian Ecosystem", Science, Sep. 6, 1996, vol. 273, pp. 1380-1383.
Turnbaugh et al., "An obesity-associated gut microbiome with increased capacity for energy harvest", Nature, Dec. 28, 2006, vol. 444, pp. 1027-1031.
Cerutti et al., "Regulation of mucosal IgA responses: lessons from primary immunodeficiencies", Annals of the New York Academy of Sciences, 2011, vol. 1238, pp. 132-144.
Fagarasan et al., "Adaptive Immune Regulation in the Gut: T Cell-Dependent and T Cell-Independent IgA Synthesis", Annual Review of Immunology, 2010, vol. 28, pp. 243-273.
Fernandez et al., "Anti-Inflammatory Role for Intracellular Dimeric Immunoglobulin A by Neutralization of Lipopolysaccharide in Epithelial Cells", Immunity, Jun. 2003, vol. 18, pp. 739-749.
Martinoli et al., "Entry Route of *Salmonella typhimurium* Directs the Type of Induced Immune Response", Dec. 2007, vol. 27, pp. 975-984.
Boullier et al., "Secretory IgA-Mediated Neutralization of Shigella flexneri Prevents Intestinal Tissue Destruction by Down-Regulating Inflammatory Circuits", The Journal of Immunology, 2009, vol. 183, pp. 5879-5885.
Phalipon et al., "Secretory Component: A New Role in Secretory IgA-Mediated Immune Exclusion in Vivo", Immunity, Jul. 2002, vol. 17, pp. 107-115.
Macpherson et al., "Induction of Protective IgA by Intestinal Dendritic Cells Carrying Commensal Bacteria", Science, 2004, vol. 303, pp. 1662-1665.

(Continued)

*Primary Examiner* — Jennifer Graser
(74) *Attorney, Agent, or Firm* — MH2 Technology Law Group, LLP

(57) ABSTRACT

The present invention provides a component having effects in vivo of improving or optimizing the intestinal environment, suppressing intestinal putrefaction, or suppressing alternation of intestinal bacterial growth and/or pathological changes of intestinal bacterial growth in gut microbiota. The invention also provides an active ingredient suitably used for treating intestinal diseases. The invention provides a monoclonal IgA antibody that binds to amino acids 11 to 333 of serine hydroxymethyltransferase.

13 Claims, 9 Drawing Sheets

(56) References Cited

OTHER PUBLICATIONS

Shinkura et al., "Separate domains of AID are required for somatic hypermutation and class-switch recombination", Nature Immunology, Jul. 2004, vol. 5, No. 7, pp. 707-712.

Ta et al., "AID mutant analyses indicate requirement for class-switch-specific cofactors", Sep. 2003, vol. 4, No. 9, pp. 843-848.

Chaudhurl et al., "Transcription-targeted DNA deamination by the AID antibody diversification enzyme", Nature, Apr. 17, 2003, vol. 422, No. 4, pp. 726-730.

Morgan et al., "Coordination of the cell-specific distribution of the four subunits of glycine decarboxylase and of serine hydroxymethyltransferase in leaves of C3-C4 intermediate species from different genera", Planta, 1993, vol. 190, pp. 468-473.

Strong et al., "Purification and Properties of Serine Hydroxymethyltransferase and C1-Tetrahydrofolate Synthase from L1210 Cells", The Journal of Biological Chemistry, 1990, vol. 265, No. 21, pp. 12149-12155.

Zeng et al., "Differential proteomic analysis during the vegetative phase change and the floral transition in *Malus domestica*", Develop. Growth Differ., 2010, vol. 52, No. 7, pp. 635-644.

Giammarioli et al., "Production and Characterization of Murine IgA monoclonal Antibodies to the Surface Antigens of Rhesus Rotavirus", Virology, 1996, vol. 225, No. 1, pp. 97-110.

Tanikawa et al., "Production and characterization of IgA Monoclonal Antibody Against Ovalbumin", Hybridoma, 2007, vol. 26, No. 5, pp. 328-332.

Imai et al., "Production of IgA monoclonal antibody against Shiga toxin binding subunits employing nasal-associated lymphoid tissue", Journal of Immunological Methods, 2005, vol. 302, pp. 125-135.

Kolberg et al., "Production and Characterization of a Mouse Monoclonal Antibody Specific for Lentil Lectin", Biol. Chem. Hopp-Seyler., Jan. 1991, vol. 372, pp. 57-61.

Reiko Shinkura, "The critical role of somatic hypermutation in gut immune responses", The Annual Meeting of the Japanese Society for Immunology, Nov. 29, 2011, Abstract 1 page, Slide pp. 1-25.

Extended European search report dated Nov. 10, 2016 for European Patent Application No. 14762432.4, 10 pages.

Turner et al., "Identification and Localization of Multiple Forms of Serine Hydroxymethyltransferase in Pea (*Pisum sativum*) and Charactrization of a cDNA Encoding a Mitochondrial Isoform", The Journal of Biological Chemistry, Jul. 5, 1992, vol. 267, No. 19, pp. 13528-13534.

Read et al., "Dynamic subcellular localization of isoforms of the folate pathway enzyme serine hydroxymethyltransferase (SHMT) through the erythrocytic cycle of Plasmodium falciparum", Malaria Journal, 2010, vol. 9, No. 1, p. 351, 19 pages.

Burns et al., "Protective Effect of Rotavirus VP6-Specific IgA Monoclonal Antibodies That Lack Neutralizing Activity", Science, Apr. 5, 1996, vol. 272, No. 5258, pp. 104-107.

Yu et al., "Neutralization of HIV by Milk Expressed Antibody", Journal of Acquired Immune Deficiency Syndromes, Jan. 1, 2013, vol. 62, No. 1, pp. 10-16.

Peterson et al., "IgA Response to Symbiotic Bacteria as a Mediator of Gut Homeostasis", Cell Host & Microbe, Nov. 2007, vol. 2, No. 5, pp. 328-339.

Oliver Pabst, "New concepts in the generation and functions of IgA", Nature Reviews Immunology, Dec. 2012, vol. 12, No. 12, pp. 821-832.

Okai et al., "High-affinity monoclonal IgA regulates gut microbiota and prevents colitis in mice", Nature Microbiology, 2016, vol. 1, No. 9, pp. 1-11.

Figure 5
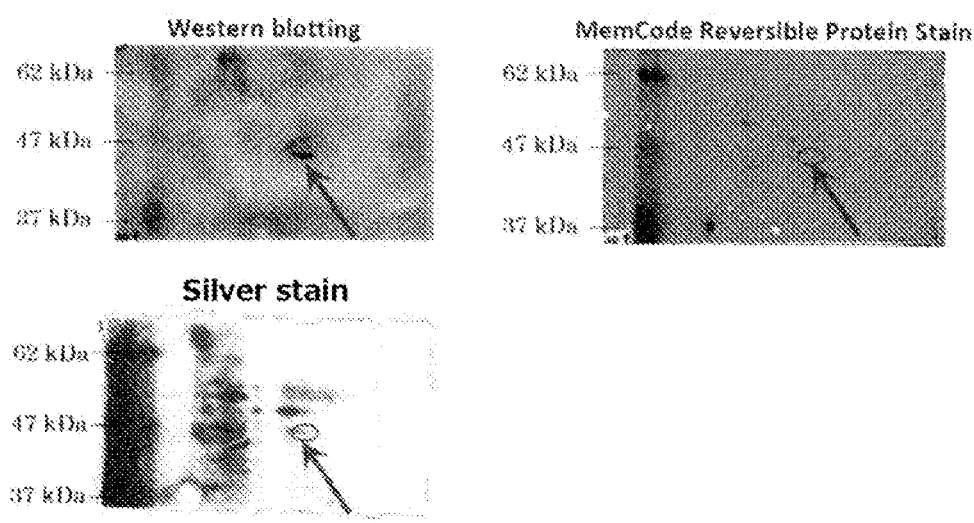
Figure 6
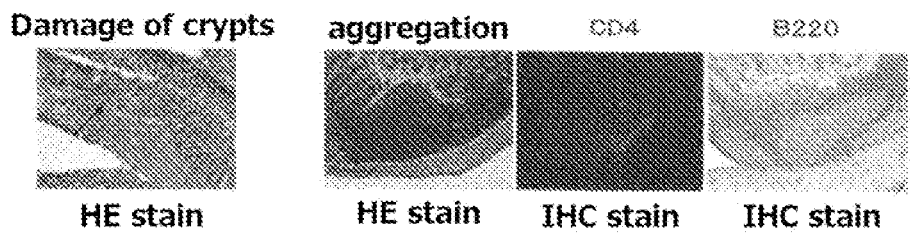
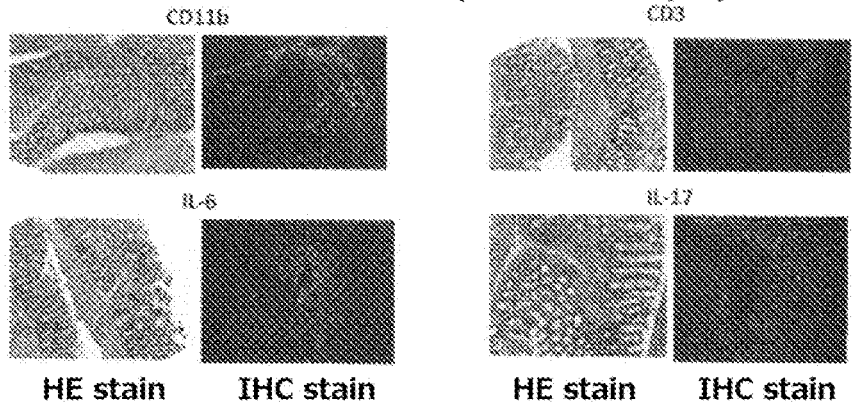

*p<0.005  p<0.001  ***p<0.0005

METHOD FOR PRODUCING MONOCLONAL IGA ANTIBODY

CROSS-REFERENCE TO RELATED APPLICATIONS

This application is U.S. National Stage application of PCT/JP2014/056216 filed 10 Mar. 2014, which claims priority to Japanese Application No. 2013-048365 filed 11 Mar. 2013 and Japanese Application No. 2013-167120 filed 9 Aug. 2013, the entire disclosures of which are hereby incorporated by reference in their entireties.

TECHNICAL FIELD

The present invention relates to a monoclonal IgA antibody, an orally or enterally administered composition containing the monoclonal IgA antibody, and a pharmaceutical composition containing the monoclonal IgA antibody.

BACKGROUND ART

For a living body, the inside of the intestinal tract is equivalent to the outside of the body and is always exposed to a very wide variety and large number of intestinal indigenous bacteria, viruses, and antigens derived from, for example, food. These intestinal indigenous bacteria form gut microbiota (hereinafter "gut microbiota" may be referred to as "intestinal bacterial flora").

It has been clarified that gut microbiota performs various functions in a living body via mucosal surfaces constructed with intestinal epithelial cells and other cells. It has also been found that when intestinal bacteria are not present, the intestinal immune system cannot normally develop (Non-patent Literature (NPL) 1 to 3).

If gut microbiota undergoes a change, and the symbiotic balance between the host and intestinal bacteria is disrupted, the homeostasis of the intestinal immune system is disrupted due to the intestinal immune system being overly stimulated. As a result, many diseases, such as inflammatory bowel disease, colorectal cancer, asthma, allergies, and obesity, may be induced with the disruption of the homeostasis. In view of this, the intestinal immune system is known to play an important role not only in eliminating pathogens, etc., but also in maintaining homeostasis of the whole immune system (Non-patent Literature (NPL) 4 to 7).

The surface of mucosal tissue in the gastrointestinal tract is a route by which antigens, such as indigenous bacteria, pathogenic microorganisms, and allergens, invade a living body. The surface of mucosal tissue is continuously attacked as the site where these many pathogenic microorganisms from the external environment invade, and is exposed to various antigens. The system for recognizing and/or responding to foreign antigens, including these pathogenic microorganisms, is called the mucosal immune system. Many cells that are responsible for mucosal immune system are present immediately below the surface of mucosal tissue in the gastrointestinal tract. These cells form a dynamic immune organization by which an immune response occurs against pathogenic microorganisms, food antigens, allergens, exogenous foreign antigens, and the like.

The mucosal immune system constructs a unique immune system that is based on an IgA antibody derived from an intestine against foreign exogenous antigens taken up through the mucosal surface constructed with intestinal epithelial cells. The intestine-derived IgA antibody is produced not only within specific tissues that are sites of immune response, such as Peyer's patches, mesenteric lymph nodes, and isolated lymphoid follicles, in a T-cell-dependent manner, but also produced in a large amount by antibody-producing cells disseminated among the intestinal lamina propria (Non-patent Literature (NPL) 8 and 9).

One of the functions of the intestine-derived IgA antibody is to eliminate pathogens. The intestine-derived IgA antibody secreted into the lumen binds to pathogens and their toxins in the intestinal lumen and neutralizes them. Alternatively, the intestine-derived IgA antibody binds to pathogens, toxins, etc., that invade intestinal epithelial cells, lamina propria, and the like, and neutralizes them while eliminating them as the intestine-derived IgA antibody itself is secreted into the lumen. A feature of the function of intestine-derived IgA antibody is that they do not cause inflammatory reactions, unlike reactions of the systemic immune system in which general antibodies are involved (Non-patent Literature (NPL) 10 to 12).

Another function of intestine-derived IgA antibody is to maintain the symbiotic relationship between intestinal indigenous bacteria and their hosts. An intestine-derived IgA antibody recognizes and binds to not only pathogens but also indigenous bacteria to prevent excessive entry of indigenous bacteria into the mucous membrane. In addition, it is believed that indigenous bacteria are not eliminated by intestine-derived IgA, and that intestine-derived IgA antibodies binding to indigenous bacteria are localized in the mucin layer on epithelial cells and form a biological film with the indigenous bacteria, in which the biological film prevents pathogens from contacting or invading the epithelial cells (Non-patent Literature (NPL) 13 and 14).

In relation to these intestinal mucosal immune systems, somatic hypermutation and class switching of antibody are known to play an important role to construct, in particular, the humoral immune system. Somatic hypermutation is a mechanism that is provided in vivo so as to diversify the immunoglobulin gene of antibody-producing B cells and produce high-affinity antibodies. Antibody class switching is a phenomenon in which the structure of the H-chain constant region is changed while the variable region of the antibody is maintained. In other words, antibody class switching is a phenomenon in which the class of immunoglobulin generated from a selected cell producing an IgM antibody is changed to different classes of immunoglobulins, such as IgG, IgE, and IgA, with the same variable region as the IgM. Due to a combination of somatic hypermutation and class switch recombination of the antibody, a variety of antibodies with various antigen-binding sites is produced, and antibodies of each class with respect to each antigen-binding site are produced. As a result, it is possible to appropriately regulate the immune functions in the body.

Both somatic hypermutation and class switching are known to require an activation-induced cytidine deaminase (AID) protein. The N-terminal domain of the AID protein is known to be involved in somatic hypermutation, while C-terminal domain of AID protein is known to be involved in class switching (Non-patent Literature (NPL) 15 and 16). In somatic hypermutation, AID is highly likely to cause DNA cleavage in an antibody gene, and the DNA cleavage triggers the introduction of mutation in an antibody gene (Non-patent Literature (NPL) 17).

In mice expressing AID-G23S (AID G23S mouse), which carries one amino acid substitution (glycine to serine) at position 23 of the AID protein, class switching occurs, and antibodies of each class are sufficiently produced. However, somatic hypermutation does not occur, and antigen-binding ability of the antibodies is reduced in an AID G23S mouse (Non-patent literature (NPL) 18).

Inflammatory bowel disease is difficult to cure and is thus specified as an intractable disease. This disease is an example of diseases caused by disruption of the balance between the host immune system and intestinal bacteria, i.e., alternation of intestinal bacterial growth and/or pathological changes of intestinal bacterial growth in gut microbiota ("alternation of intestinal bacterial growth and/or pathological changes of intestinal bacterial growth in gut microbiota" may be refer to as "dysbiosis"). In a clinical setting, this disease is treated by systemic administration of an immunosuppressant agent, such as a steroid and an anti-TNF antibody. However, these drugs require long-term administration, and a significant problem of side effects arises from these drugs. Therefore, it is desired that a medicinal drug that has reduced side effects and that is effective in treating or preventing intestinal diseases, such as inflammatory bowel disease, is developed.

CITATION LIST

Non-patent Literature

NPL 1: Cerf-Bensussan N and Gaboriau-Routhiau V, Nat Rev Immunol 2010; 10:735
NPL 2: Hooper L V and Macpherson A J, Nat Rev Immunol 2010; 10:159
NPL 3: Round J L and Mazmanian S K, Proc Natl Acad Sci USA 2010; 107:12204
NPL 4: Vijay-Kumar M et al., Science 2010; 328:228
NPL 5: Shulzhenko N et al., Nat Med 2011; 17:1585
NPL 6: Bry L et al., Science 1996; 273:1380
NPL 7: Turnbaugh P J et al., Nature 2006; 444:1027
NPL 8: Cerutti A et al., Ann NY Acad Sci 2011; 1238:132
NPL 9: Fagarasan S et al., Annu Rev Immunol 2010; 28:243
NPL 10: Fernandez M I et al., Immunity 2003; 18:739
NPL 11: Martinoli C et al., Immunity 2007; 27:975
NPL 12: Boullier S et al., J Immunol 2009; 183:5879
NPL 13: Phalipon A et al., Immunity 2002; 17:107
NPL 14: Macpherson A J and Uhr T, Science 2004; 303:1662
NPL 15: Shinkura R et al., Nat Immunol 2004; 5:707
NPL 16: Ta V T et al., Nat Immunol 2003; 4:843
NPL 17: Chaudhuri J et al. Nature 2003; 422:726
NPL 18: Wei M et al., Nature Immunology 12(3), 264-270, 2011

SUMMARY OF INVENTION

Technical Problem

An object of the present invention is to provide a component having effects in vivo of improving or optimizing the intestinal environment, suppressing intestinal putrefaction, or suppressing alternation of intestinal bacterial growth or pathological changes of intestinal bacterial growth in gut microbiota. Another object of the present invention is to provide an active ingredient suitably used for treating intestinal diseases.

Solution to Problem

The present inventor conducted extensive research to solve the above problems and found that a monoclonal IgA antibody that specifically binds to a particular region of a protein having a particular amino acid sequence has effects to suppress an excessive response in the intestinal immune system and to make recovery from reduction of crypts in the lamina propria in the large intestine. These effects of a monoclonal IgA antibody were confirmed by orally administering the antibody to an individual.

The present invention has been accomplished based on the above findings and includes the broad embodiments described below.

Item 1: A monoclonal IgA antibody that binds to amino acids 11 to 333 of serine hydroxymethyltransferase.

The embodiment of the invention described in Item 1 broadly includes the embodiments of monoclonal IgA antibody described in the following Items 1-1 to 1-17.

Item 1-1: The monoclonal IgA antibody according to Item 1, wherein the monoclonal IgA antibody binds to amino acids 25 to 44 of serine hydroxymethyltransferase.

Item 1-2: The monoclonal IgA antibody according to Item 1, wherein the monoclonal IgA antibody binds to amino acids 25 to 28 of serine hydroxymethyltransferase.

Item 1-3: The monoclonal IgA antibody according to Item 1, 1-1, or 1-2, wherein the monoclonal IgA antibody comprises a heavy chain variable region containing
(1) a heavy chain CDR 1 consisting of the amino acid sequence represented by SEQ ID NO: 3, 13, 23, 33, or 43,
(2) a heavy chain CDR 2 consisting of the amino acid sequence represented by SEQ ID NO: 4, 14, 24, 34, or 44, and
(3) a heavy chain CDR 3 consisting of the amino acid sequence represented by SEQ ID NO: 5, 15, 25, 35, or 45, and/or a light chain variable region containing
(I) a light chain CDR 1 consisting of the amino acid sequence represented by SEQ ID NO: 8, 18, 28, 38, or 48,
(II) a light chain CDR 2 consisting of the amino acid sequence represented by SEQ ID NO: 9, 19, 29, 39, or 49, and
(III) a light chain CDR 3 consisting of the amino acid sequence represented by SEQ ID NO: 10, 20, 30, 40 or 50.

Item 1-4: The monoclonal IgA antibody according to any one of Items 1 and 1-1 to 1-3, wherein the monoclonal IgA antibody comprises a heavy chain variable region consisting of the amino acid sequence represented by SEQ ID NO: 2, 12, 22, 32, or 42, and/or a light chain variable region consisting of the amino acid sequence represented by SEQ ID NO: 7, 17, 27, 37, or 47.

Item 1-5: The monoclonal IgA antibody according to any one of Items 1 and 1-1 to 1-4, wherein the monoclonal IgA antibody comprises a heavy chain consisting of the amino acid sequence represented by SEQ ID NO: 1, 11, 21, 31, or 41, and/or a light chain consisting of the amino acid sequence represented by SEQ ID NO: 6, 16, 26, 36, or 46.

Item 1-6: The monoclonal IgA antibody according to any one of Items 1 and 1-1 to 1-5, wherein the monoclonal IgA antibody inhibits the growth of at least two kinds of intestinal bacteria.

Item 1-7: The monoclonal IgA antibody according to any one of Items 1 and 1-1 to 1-6, wherein the intestinal bacteria are at least two kinds of bacteria selected from the group consisting of
bacteria belonging to the genus *Prevotella*,
bacteria belonging to the genus *Bacteroides*,
bacteria belonging to the genus *Megamonas*,
bacteria belonging to the genus *Bifidobacterium*,
bacteria belonging to the genus *Faecalibacterium*,
bacteria belonging to the genus *Coprococcus*,
bacteria belonging to the genus *Ruminococcus*,
bacteria belonging to the genus *Blautia*, bacteria belonging to the genus *Eubacterium*,
bacteria belonging to the genus *Roseburia*,
bacteria belonging to the genus *Lactobacillus*,
bacteria belonging to the genus *Clostridium*,
bacteria belonging to the genus *Escherichia*,
bacteria belonging to the genus *Staphylococcus*,
bacteria belonging to the genus *Enterococcus*,
bacteria belonging to the genus *Pseudomonas*, and
bacteria belonging to the genus *Enterorhabdus*.

Item 1-8: The monoclonal IgA antibody according to any one of Items 1 and 1-1 to 1-7, wherein the intestinal bacteria are at least two kinds of bacteria selected from the group consisting of
*Prevotella melaninogenica*,
*Bacteroidetes vulgatus*,
*Megamonas funiformis*,
*Megamonas hypermegale*,
*Bifidobacterium bifidum*,
*Faecalibacterium prausnitzii*,
*Coprococcus eutactus*,
*Ruminococcus obeum*,
*Blautia productus*,
*Blautia coccoides*,
*Eubacterium rectale*,
*Roseburia intestinalis*,
*Clostridium difficile*,
*Escherichia coli*,
*Staphylococcus aureus*,
*Lactobacillus murinus*,
*Lactobacillus casei*,
*Enterococcus faecalis*,
*Pseudomonas fulva*, and
*Enterorhabdus mucosicola*.

Item 1-9: The monoclonal IgA antibody according to any one of Items 1 and 1-1 to 1-8, wherein the monoclonal IgA antibody is $IgA_1$ or $IgA_2$.

Item 1-10: The monoclonal IgA antibody according to any one of Items 1 and 1-1 to 1-9, wherein the monoclonal IgA antibody contains a J chain-containing polymer.

Item 1-11: The monoclonal IgA antibody according to any one of Items 1 and 1-1 to 1-10, wherein the monoclanal IgA antibody contains a secretory component.

Item 1-12: The monoclonal IgA antibody according to any one of Items 1 and 1-1 to 1-11, wherein the monoclonal IgA antibody has an amino acid sequence derived from the same species.

Item 1-13: The monoclonal IgA antibody according to any one of Items 1 and 1-1 to 1-12, wherein the monoclonal IgA antibody has an amino acid sequence derived from mouse, rat, hamster, rabbit, goat, sheep, donkey, pig, cow, horse, chicken, monkey, chimpanzee, or human.

Item 1-14: The monoclonal IgA antibody according to any one of Items 1 and 1-1 to 1-11, wherein the monoclonal IgA antibody has amino acid sequences derived from different species.

Item 1-15: The monoclonal IgA antibody according to any one of Items 1, 1-1 to 1-11, and 1-14, wherein the monoclonal IgA antibody has amino acid sequences derived from at least two species selected from the group consisting of a mouse, rat, hamster, rabbit, goat, sheep, donkey, pig, cow, horse, monkey, chicken, chimpanzee, and human.

Item 1-16: The monoclonal IgA antibody according to any one of Items 1, 1-1 to 1-11, 1-14, and 1-15, wherein the monoclonal IgA antibody is a humanized antibody.

Item 1-17: The monoclonal IgA antibody according to any one of Items 1, 1-1 to 1-11, 1-14, and 1-15, wherein the monoclonal IgA antibody is a chimeric antibody.

Item 2: A method for producing the monoclonal IgA antibody of Item 1, wherein the method comprises the following steps 1 and 2:

(1) step 1: mixing and fusing B cells collected from an intestinal lamina propria with other types of cells to prepare hybridomas; and (2) step 2: culturing the hybridomas formed in step 1, determining cells that produce a monoclonal IgA antibody that binds to at least two kinds of intestinal bacteria, and collecting the IgA antibody from the cells.

The embodiment of the invention described in Item 2 broadly includes the embodiments of the monoclonal IgA antibody production method described in the following Items 2-1 to 2-18.

Item 2-1: The production method according to Item 2, wherein the B cells are IgA antibody-producing cells.

Item 2-2: The production method according to Item 2 or 2-1, wherein the intestinal lamina propria is derived from mouse, rat, hamster, rabbit, goat, sheep, donkey, pig, cow, horse, chicken, monkey, chimpanzee, or human.

Item 2-3: The production method according to Item 2, 2-1, or 2-2, wherein the other cells are myeloma cells.

Item 2-4: The production method according to any one of Items 2 and 2-1 to 2-3, wherein the other cells are derived from mouse, rat, hamster, rabbit, goat, sheep, donkey, pig, cow, horse, chicken, monkey, chimpanzee, or human.

Item 2-5: The production method according to any one of Items 2 and 2-1 to 2-4, wherein the intestinal bacteria are at least two kinds of bacteria selected from the group consisting of
bacteria belonging to the genus *Prevotella*,
bacteria belonging to the genus *Bacteroides*,
bacteria belonging to the genus *Megamonas*,
bacteria belonging to the genus *Bifidobacterium*,
bacteria belonging to the genus *Faecalibacterium*,
bacteria belonging to the genus *Coprococcus*,
bacteria belonging to the genus *Ruminococcus*,
bacteria belonging to the genus *Blautia*,
bacteria belonging to the genus *Eubacterium*,
bacteria belonging to the genus *Roseburia*,
bacteria belonging to the genus *Lactobacillus*,
bacteria belonging to the genus *Clostridium*,
bacteria belonging to the genus *Escherichia*,
bacteria belonging to the genus *Staphylococcus*,
bacteria belonging to the genus *Enterococcus*,
bacteria belonging to the genus *Pseudomonas*, and
bacteria belonging to the genus *Enterorhabdus*.

Item 2-6: The production method according to any one of Items 2 and 2-1 to 2-5, wherein the intestinal bacteria are at least two kinds of bacteria selected from the group consisting of
*Prevotella melaninogenica*,
*Bacteroidetes vulgatus*,
*Megamonas funiformis*,
*Megamonas hypermegale*,
*Bifidobacterium bifidum*,
*Faecalibacterium prausnitzii*,
*Coprococcus eutactus*,
*Ruminococcus obeum*,
*Blautia productus*,
*Blautia coccoides*,
*Eubacterium rectale*,
*Roseburia intestinalis*,
*Lactobacillus murinus*,
*Lactobacillus casei*,
*Clostridium difficile*,
*Escherichia coli*,

*Staphylococcus aureus,*
*Enterococcus faecalis,*
*Pseudomonas fulva,* and
*Enterorhabdus mucosicola.*

Item 2-7: The production method according to any one of Items 2 and 2-1 to 2-6, wherein the monoclonal IgA antibody is IgA$_1$ or IgA$_2$.

Item 2-8: The production method according to any one of Items 2 and 2-1 to 2-7, wherein the monoclonal IgA antibody contains a J chain-containing polymer.

Item 2-9: The production method according to any one of Items 2 and 2-1 to 2-8, wherein the monoclonal IgA antibody contains a secretory component.

Item 2-10: The production method according to any one of Items 2 and 2-1 to 2-9, wherein the monoclonal IgA antibody has an amino acid sequence derived from the same species.

Item 2-11: The production method according to any one of Items 2 and 2-1 to 2-10, wherein the monoclonal IgA antibody has an amino acid sequence derived from mouse, rat, hamster, rabbit, goat, sheep, donkey, pig, cow, horse, chicken, monkey, chimpanzee, or human.

Item 2-12: The production method according to any one of Items 2 and 2-1 to 2-9, wherein the monoclonal IgA antibody has amino acid sequences derived from different species.

Item 2-13: The production method according to any one of Items 2, 2-1 to 2-9, and 2-12, wherein the monoclonal IgA antibody has amino acid sequences derived from at least two species selected from the group consisting of mouse, rat, hamster, rabbit, goat, sheep, donkey, pig, cow, horse, chicken, monkey, chimpanzee, and human.

Item 2-14: The production method according to any one of Items 2, 2-1 to 2-9, 2-12, and 2-13, wherein the monoclonal IgA antibody is a humanized antibody.

Item 2-15: The production method according to any one of Items 2, 2-1 to 2-9, 2-12, and 2-13, wherein the monoclonal IgA antibody is a chimeric antibody.

Item 2-16: The production method according to any one of Items 2 and 2-1 to 2-15, wherein the monoclonal IgA antibody comprises a heavy chain variable region containing
(1) a heavy chain CDR 1 consisting of the amino acid sequence represented by SEQ ID NO: 3, 13, 23, 33, or 43,
(2) a heavy chain CDR 2 consisting of the amino acid sequence represented by SEQ ID NO: 4, 14, 24, 34, or 44, and
(3) a heavy chain CDR 3 consisting of the amino acid sequence represented by SEQ ID NO: 5, 15, 25, 35, or 45, and/or a light chain variable region containing
(I) a light chain CDR 1 consisting of the amino acid sequence represented by SEQ ID NO: 8, 18, 28, 38, or 48,
(II) a light chain CDR 2 consisting of the amino acid sequence represented by SEQ ID NO: 9, 19, 29, 39, or 49, and
(III) a light chain CDR 3 consisting of the amino acid sequence represented by SEQ ID NO: 10, 20, 30, 40 or 50.

Item 2-17: The production method according to any one of Items 2 and 2-1 to 2-16, wherein the monoclonal IgA antibody comprises a heavy chain variable region consisting of the amino acid sequence represented by SEQ ID NO: 2, 12, 22, 32, or 42, and/or a light chain variable region consisting of the amino acid sequence represented by SEQ ID NO: 7, 17, 27, 37, or 47.

Item 2-18: The production method according to any one of Items 2 and 2-1 to 2-17, wherein the monoclonal IgA antibody comprises a heavy chain consisting of the amino acid sequence represented by SEQ ID NO: 1, 11, 21, 31, or 41, and/or a light chain consisting of the amino acid sequence represented by SEQ ID NO: 6, 16, 26, 36, or 46.

Item 3: A pharmaceutical composition containing the monoclonal IgA antibody of Item 1.

The embodiment of the invention described in Item 3 broadly includes the embodiments of pharmaceutical composition described in the following Items 3-1 to 3-6.

Item 3-1: The pharmaceutical composition according to Item 3, wherein the pharmaceutical composition is used in the treatment of an intestinal disease.

Item 3-2: The pharmaceutical composition according to Item 3 or 3-1, wherein the intestinal disease is caused by alternation of intestinal bacterial growth and/or pathological changes of intestinal bacterial growth in gut microbiota.

Item 3-3: The pharmaceutical composition according to Item 3, 3-1, or 3-2, wherein the intestinal disease caused by alternation of intestinal bacterial growth and/or pathological changes of intestinal bacterial growth in gut microbiota is selected from the group consisting of inflammatory bowel disease, ulcerative colitis, Crohn's disease, allergies, asthma, obesity, and autoimmune diseases.

Item 3-4: The pharmaceutical composition according to any one of Items 3 and 3-1 to 3-3, wherein the intestinal bacteria are at least two kinds of bacteria selected from the group consisting of
bacteria belonging to the genus *Prevotella,*
bacteria belonging to the genus *Bacteroides,*
bacteria belonging to the genus *Megamonas,*
bacteria belonging to the genus *Bifidobacterium,*
bacteria belonging to the genus *Faecalibacterium,*
bacteria belonging to the genus *Coprococcus,*
bacteria belonging to the genus *Ruminococcus,*
bacteria belonging to the genus *Blautia,*
bacteria belonging to the genus *Eubacterium,*
bacteria belonging to the genus *Roseburia,*
bacteria belonging to the genus *Lactobacillus,*
bacteria belonging to the genus *Clostridium,*
bacteria belonging to the genus *Escherichia,*
bacteria belonging to the genus *Staphylococcus,*
bacteria belonging to the genus *Enterococcus,*
bacteria belonging to the genus *Pseudomonas,* and
bacteria belonging to the genus *Enterorhabdus.*

Item 3-5: The pharmaceutical composition according to any one of Items 3 and 3-1 to 3-4, wherein the intestinal bacteria are at least two kinds of bacteria selected from the group consisting of
*Prevotella melaninogenica,*
*Bacteroidetes vulgatus,*
*Megamonas funiformis,*
*Megamonas hypermegale,*
*Bifidobacterium bifidum,*
*Faecalibacterium prausnitzii,*
*Coprococcus eutactus,*
*Ruminococcus obeum,*
*Blautia productus,*
*Blautia coccoides,*
*Eubacterium rectale,*
*Roseburia intestinalis,*
*Lactobacillus murinus,*
*Lactobacillus casei,*
*Clostridium difficile,*
*Escherichia coli,*
*Staphylococcus aureus,*
*Enterococcus faecalis,*
*Pseudomonas fulva,* and
*Enterorhabdus mucosicola.*

Item 3-6: The pharmaceutical composition according to any one of Items 3 and 3-1 to 3-5, wherein the pharmaceutical composition is orally or enterally administered.

Item 4: An orally or enterally administered composition containing the monoclonal IgA antibody of Item 1.

The embodiment of the invention described in Item 4 broadly includes the embodiments of the orally or enterally administered composition described in the following Items 4-1 to 4-6.

Item 4-1: The orally or enterally administered composition according to Item 4, wherein the orally or enterally administered composition suppresses alternation of intestinal bacterial growth and/or pathological changes of intestinal bacterial growth in gut microbiota.

Item 4-2: The orally or enterally administered composition according to Item 4 or 4-1, wherein the intestinal bacteria are at least two kinds of bacteria selected from the group consisting of
bacteria belonging to the genus *Prevotella*,
bacteria belonging to the genus *Bacteroides*,
bacteria belonging to the genus *Megamonas*,
bacteria belonging to the genus *Bifidobacterium*,
bacteria belonging to the genus *Faecalibacterium*,
bacteria belonging to the genus *Coprococcus*,
bacteria belonging to the genus *Ruminococcus*,
bacteria belonging to the genus *Blautia*,
bacteria belonging to the genus *Eubacterium*,
bacteria belonging to the genus *Roseburia*,
bacteria belonging to the genus *Lactobacillus*,
bacteria belonging to the genus *Clostridium*,
bacteria belonging to the genus *Escherichia*,
bacteria belonging to the genus *Staphylococcus*,
bacteria belonging to the genus *Enterococcus*,
bacteria belonging to the genus *Pseudomonas*, and
bacteria belonging to the genus *Enterorhabdus*.

Item 4-3: The orally or enterally administered composition according to Item 4, 4-1, or 4-2, wherein the intestinal bacteria are at least two kinds of bacteria selected from the group consisting of
*Prevotella melaninogenica*,
*Bacteroidetes vulgatus*,
*Megamonas funiformis*,
*Megamonas hypermegale*,
*Bifidobacterium bifidum*,
*Faecalibacterium prausnitzii*,
*Coprococcus eutactus*,
*Ruminococcus obeum*,
*Blautia productus*,
*Blautia coccoides*,
*Eubacterium rectale*,
*Roseburia intestinalis*,
*Lactobacillus murinus*,
*Lactobacillus casei*,
*Clostridium difficile*,
*Escherichia coli*,
*Staphylococcus aureus*,
*Enterococcus faecalis*,
*Pseudomonas fulva*, and
*Enterorhabdus mucosicola*.

Item 4-4: The orally or enterally administered composition according to any one of Items 4 and 4-1 to 4-3, wherein the orally or enterally administered composition is a composition that improves the intestinal environment, a composition that optimizes the intestinal environment, or a composition that prevents intestinal putrefaction.

Item 4-5: The orally or enterally administered composition according to any one of Items 4 and 4-1 to 4-4, wherein the orally or enterally administered composition is a food and beverage composition.

Item 4-6: The orally or enterally administered composition according to any one of Items 4 and 4-1 to 4-5, wherein the orally or enterally administered composition is a feed composition.

Item 5: A nucleic acid encoding the monoclonal IgA antibody of Item 1.

Item 6: A hybridoma that produces the monoclonal IgA antibody of Item 1.

The embodiment of the invention described in Item 6 broadly includes the embodiments of the hybridoma described in the following Items 6-1 to 6-4.

Item 6-1: The hybridoma according to Item 6, wherein the hybridoma is derived from the same species.

Item 6-2: The hybridoma according to Item 6 or 6-1, wherein the hybridoma is derived from mouse, rat, hamster, rabbit, goat, sheep, donkey, pig, cow, horse, chicken, monkey, chimpanzee, or human.

Item 6-3: The hybridoma according to Item 6, wherein the hybridoma is derived from different species.

Item 6-4: The hybridoma according to Item 6 or 6-2, wherein the hybridoma is derived from at least two species selected from the group consisting of mouse, rat, hamster, rabbit, goat, sheep, donkey, pig, cow, horse, chicken, monkey, chimpanzee, or human.

Item 7: A method for suppressing the growth of at least two kinds of intestinal bacteria, wherein the method comprises step of contacting the antibody of Item 1 to at least two kinds of intestinal bacteria.

The embodiment of the invention described in Item 7 broadly includes the embodiments of the disease treatment method described in the following Items 7-1 to 7-3.

Item 7-1: The method according to Item 7, wherein the contacting of the antibody to the intestinal bacteria is performed within the intestine.

Item 7-2: The treatment method according to Item 7 or 7-1, wherein the intestinal bacteria are at least two kinds of bacteria selected from the group consisting of
bacteria belonging to the genus *Prevotella*,
bacteria belonging to the genus *Bacteroides*,
bacteria belonging to the genus *Megamonas*,
bacteria belonging to the genus *Bifidobacterium*,
bacteria belonging to the genus *Faecalibacterium*,
bacteria belonging to the genus *Coprococcus*,
bacteria belonging to the genus *Ruminococcus*,
bacteria belonging to the genus *Blautia*,
bacteria belonging to the genus *Eubacterium*,
bacteria belonging to the genus *Roseburia*,
bacteria belonging to the genus *Lactobacillus*,
bacteria belonging to the genus *Clostridium*,
bacteria belonging to the genus *Escherichia*,
bacteria belonging to the genus *Staphylococcus*,
bacteria belonging to the genus *Enterococcus*,
bacteria belonging to the genus *Pseudomonas*, and
bacteria belonging to the genus *Enterorhabdus*.

Item 7-3: The treatment method according to any one of Items 7, 7-1, or 7-2, wherein the intestinal bacteria are at least two kinds of bacteria selected from the group consisting of
*Prevotella melaninogenica*,
*Bacteroidetes vulgatus*,
*Megamonas funiformis*,
*Megamonas hypermegale*,
*Bifidobacterium bifidum*,

*Faecalibacterium prausnitzii,*
*Coprococcus eutactus,*
*Ruminococcus obeum,*
*Blautia productus,*
*Blautia coccoides,*
*Eubacterium rectale,*
*Roseburia intestinalis,*
*Lactobacillus murinus,*
*Lactobacillus casei,*
*Clostridium difficile,*
*Escherichia coli,*
*Staphylococcus aureus,*
*Enterococcus faecalis,*
*Pseudomonas fulva,* and
*Enterorhabdus mucosicola.*

Item 8: A method for treating an intestinal disease, wherein the method comprises the step of administering an effective amount of the antibody of Item 1 to a human suffering from an intestinal disease.

The embodiment of the invention described in Item 8 broadly includes the embodiments of the disease treatment method described in the following Items 8-1 to 8-5.

Item 8-1: The treatment method according to Item 8, wherein the intestinal disease is caused by alternation of intestinal bacterial growth and/or pathological changes of intestinal bacterial growth in gut microbiota.

Item 8-2: The treatment method according to Item 8 or 8-1, wherein the intestinal disease caused by alternation of intestinal bacterial growth and/or pathological changes of intestinal bacterial growth in gut microbiota is selected from the group consisting of inflammatory bowel disease, ulcerative colitis, Crohn's disease, allergies, asthma, obesity, and autoimmune diseases.

Item 8-3: The treatment method according to Item 8, 8-1, or 8-2, wherein the intestinal bacteria are at least two kinds of bacteria selected from the group consisting of
bacteria belonging to the genus *Prevotella,*
bacteria belonging to the genus *Bacteroides,*
bacteria belonging to the genus *Megamonas,*
bacteria belonging to the genus *Bifidobacterium,*
bacteria belonging to the genus *Faecalibacterium,*
bacteria belonging to the genus *Coprococcus,*
bacteria belonging to the genus *Ruminococcus,*
bacteria belonging to the genus *Blautia,*
bacteria belonging to the genus *Eubacterium,*
bacteria belonging to the genus *Roseburia,*
bacteria belonging to the genus *Lactobacillus,*
bacteria belonging to the genus *Clostridium,*
bacteria belonging to the genus *Escherichia,*
bacteria belonging to the genus *Staphylococcus,*
bacteria belonging to the genus *Enterococcus,*
bacteria belonging to the genus *Pseudomonas,* and
bacteria belonging to the genus *Enterorhabdus.*

Item 8-4: The treatment method according to any one of Items 8 and 8-1 to 8-3, wherein the intestinal bacteria are at least two kinds of bacteria selected from the group consisting of
*Prevotella melaninogenica,*
*Bacteroidetes vulgatus,*
*Megamonas funiformis,*
*Megamonas hypermegale,*
*Bifidobacterium bifidum,*
*Faecalibacterium prausnitzii,*
*Coprococcus eutactus,*
*Ruminococcus obeum,*
*Blautia productus,*
*Blautia coccoides,*
*Eubacterium rectale,*
*Roseburia intestinalis,*
*Lactobacillus murinus,*
*Lactobacillus casei,*
*Clostridium difficile,*
*Escherichia coli,*
*Staphylococcus aureus,*
*Enterococcus faecalis,*
*Pseudomonas fulva,* and
*Enterorhabdus mucosicola.*

Item 8-5: The treatment method according to any one of Items 8 and 8-1 to 8-4, wherein the administration is performed orally or enterally.

Item 9: A monoclonal IgA antibody for use in treating an intestinal disease, wherein the monoclonal IgA antibody is defined in Item 1.

The embodiment of the invention described in Item 9 broadly includes the embodiments of the monoclonal IgA antibody described in the following Items 9-1 to 9-5.

Item 9-1: The monoclonal IgA antibody according to Item 9, wherein the monoclonal IgA antibody is used in treating an intestinal disease caused by alternation of intestinal bacterial growth and/or pathological changes of intestinal bacterial growth in gut microbiota.

Item 9-2: The monoclonal IgA antibody according to Item 8 or 8-1, wherein the intestinal disease caused by alternation of intestinal bacterial growth and/or pathological changes of intestinal bacterial growth in gut microbiota is selected from the group consisting of inflammatory bowel disease, ulcerative colitis, Crohn's disease, allergies, asthma, obesity, and autoimmune diseases.

Item 9-3: The monoclonal IgA antibody according to Item 9, 9-1, or 9-2, wherein the intestinal bacteria are at least two kinds of bacteria selected from the group consisting of
bacteria belonging to the genus *Prevotella,*
bacteria belonging to the genus *Bacteroides,*
bacteria belonging to the genus *Megamonas,*
bacteria belonging to the genus *Bifidobacterium,*
bacteria belonging to the genus *Faecalibacterium,*
bacteria belonging to the genus *Coprococcus,*
bacteria belonging to the genus *Ruminococcus,*
bacteria belonging to the genus *Blautia,*
bacteria belonging to the genus *Eubacterium,*
bacteria belonging to the genus *Roseburia,*
bacteria belonging to the genus *Lactobacillus,*
bacteria belonging to the genus *Clostridium,*
bacteria belonging to the genus *Escherichia,*
bacteria belonging to the genus *Staphylococcus,*
bacteria belonging to the genus *Enterococcus,*
bacteria belonging to the genus *Pseudomonas,* and
bacteria belonging to the genus *Enterorhabdus.*

Item 9-4: The monoclonal IgA antibody according to any one of Items 9 and 9-1 to 9-3, wherein the intestinal bacteria are at least two kinds of bacteria selected from the group consisting of
*Prevotella melaninogenica,*
*Bacteroidetes vulgatus,*
*Megamonas funiformis,*
*Megamonas hypermegale,*
*Bifidobacterium bifidum,*
*Faecalibacterium prausnitzii,*
*Coprococcus eutactus,*
*Ruminococcus obeum,*
*Blautia productus,*
*Blautia coccoides,*
*Eubacterium rectale,*
*Roseburia intestinalis,*

*Lactobacillus murinus,*
*Lactobacillus casei,*
*Clostridium difficile,*
*Escherichia coli,*
*Staphylococcus aureus,*
*Enterococcus faecalis,*
*Pseudomonas fulva,* and
*Enterorhabdus mucosicola.*

Item 9-5: The monoclonal IgA antibody according to any one of Items 9 and 9-1 to 9-4, wherein the monoclonal IgA antibody is used for oral or enteral administration.

Item 10: Use of the monoclonal IgA antibody of Item 1, for the manufacture of a medicament for treating an intestinal disease.

The embodiment of the invention described in Item 10 broadly includes the embodiments of the use of monoclonal IgA antibody described in the following Items 10-1 to 10-5.

Item 10-1: The use according to Item 10, wherein the intestinal disease is caused by alternation of intestinal bacterial growth and/or pathological changes of intestinal bacterial growth in gut microbiota.

Item 10-2: The use according to Item 10 or 10-1, wherein the intestinal disease caused by alternation of intestinal bacterial growth and/or pathological changes of intestinal bacterial growth in gut microbiota is selected from the group consisting of inflammatory bowel disease, ulcerative colitis, Crohn's disease, allergies, asthma, obesity, and autoimmune diseases.

Item 10-3: The use according to Item 10, 10-1, or 10-2, wherein the intestinal bacteria are at least two kinds of bacteria selected from the group consisting of
bacteria belonging to the genus *Prevotella,*
bacteria belonging to the genus *Bacteroides,*
bacteria belonging to the genus *Megamonas,*
bacteria belonging to the genus *Bifidobacterium,*
bacteria belonging to the genus *Faecalibacterium,*
bacteria belonging to the genus *Coprococcus,*
bacteria belonging to the genus *Ruminococcus,*
bacteria belonging to the genus *Blautia,*
bacteria belonging to the genus *Eubacterium,*
bacteria belonging to the genus *Roseburia,*
bacteria belonging to the genus *Lactobacillus,*
bacteria belonging to the genus *Clostridium,*
bacteria belonging to the genus *Escherichia,*
bacteria belonging to the genus *Staphylococcus,*
bacteria belonging to the genus *Enterococcus,*
bacteria belonging to the genus *Pseudomonas,* and
bacteria belonging to the genus *Enterorhabdus.*

Item 10-4: The use according to any one of Items 10 and 10-1 to 10-3, wherein the intestinal bacteria are at least two kinds of bacteria selected from the group consisting of
*Prevotella melaninogenica,*
*Bacteroidetes vulgatus,*
*Megamonas funiformis,*
*Megamonas hypermegale,*
*Bifidobacterium bifidum,*
*Faecalibacterium prausnitzii,*
*Coprococcus eutactus,*
*Ruminococcus obeum,*
*Blautia productus,*
*Blautia coccoides,*
*Eubacterium rectale,*
*Roseburia intestinalis,*
*Lactobacillus murinus,*
*Lactobacillus casei,*
*Clostridium difficile,*
*Escherichia coli,*
*Staphylococcus aureus,*
*Enterococcus faecalis,*
*Pseudomonas fulva,* and
*Enterorhabdus mucosicola.*

Item 10-5: The use according to any one of Items 10 and 10-1 to 10-4, wherein the use is for oral or enteral administration.

BRIEF DESCRIPTION OF DRAWINGS

In FIG. 1, the rows in the table indicate the bacteria from top to bottom: *Escherichia coli* (DH5α strain), *Escherichia coli* (a cloned strain from mouse intestinal bacteria), *Staphylococcus aureus, Enterococcus faecalis, Pseudomonas fulva, Lactobacillus murinus, Enterorhabdus mucosicola, Lactobacillus casei, Coprococcus eutactus, Blautia coccoides, Megamonas hypermegale, Eubacterium rectale,* and *Bifidobacterium bifidum. * In FIG. 1, the columns in the table indicate the names of the following clones from left to right: W1, W2, W3, W4, W6, W7, W11, W14, W24, W27, W28, W30, W32, W34, W37, W43, and W45, followed by G1, G8, G9, G10, G12, G14, G15, G16, G18, and G19. "N/A" in FIG. 1 indicates "unconfirmed."

FIG. 4A-D show results of Western blot analysis for cell extracts from various intestinal bacteria by using various monoclonal IgA antibodies. FIG. 4(A) indicates experimental results using W27 monoclonal IgA antibody, FIG. 4 (B) indicates experimental results using W30 monoclonal IgA antibody, and FIG. 4 (C) indicates experimental results using W45 monoclonal IgA antibody. In each figure, the lanes from left to right indicate the extracts of *Escherichia coli* (DH5α strain; commercially available product), *Escherichia coli* (a cloned strain from mouse intestinal bacteria), *Pseudomonas fulva,* and *Staphylococcus aureus.

FIG. 5 shows results of two-dimensional electrophoresis. The top left indicates results of Western blotting, the top right indicates results of MemCode reversible protein staining, and the bottom row indicates results of silver staining.

Spots (arrows) were confirmed to be located at the same position in all the figures, and the gel was excised and subjected to MS analysis.

FIG. 6 shows HE-stained sections of the large intestine of G23S mice.

Figure 7:
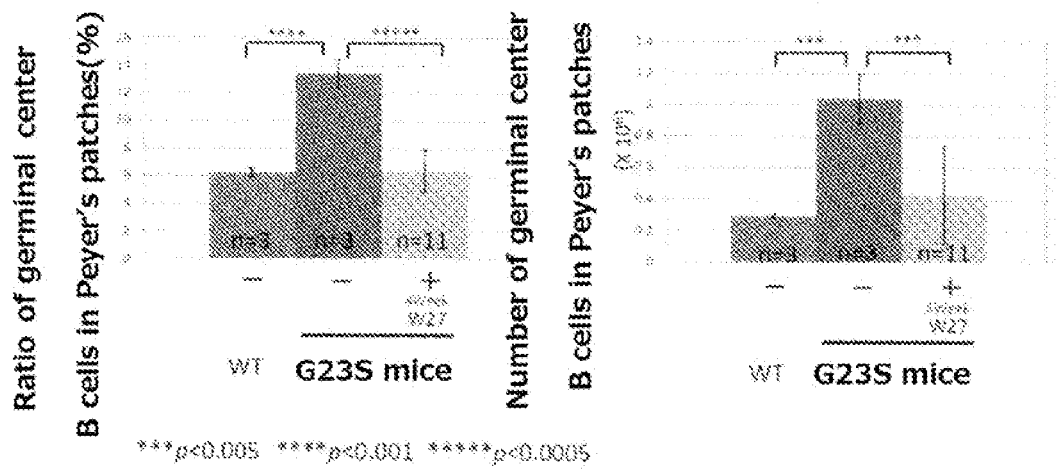

FIG. 7 shows experimental results to measure the number of Peyer's patch germinal center B cells when W27 monoclonal IgA antibody was orally administered to mice.

Figure 8:
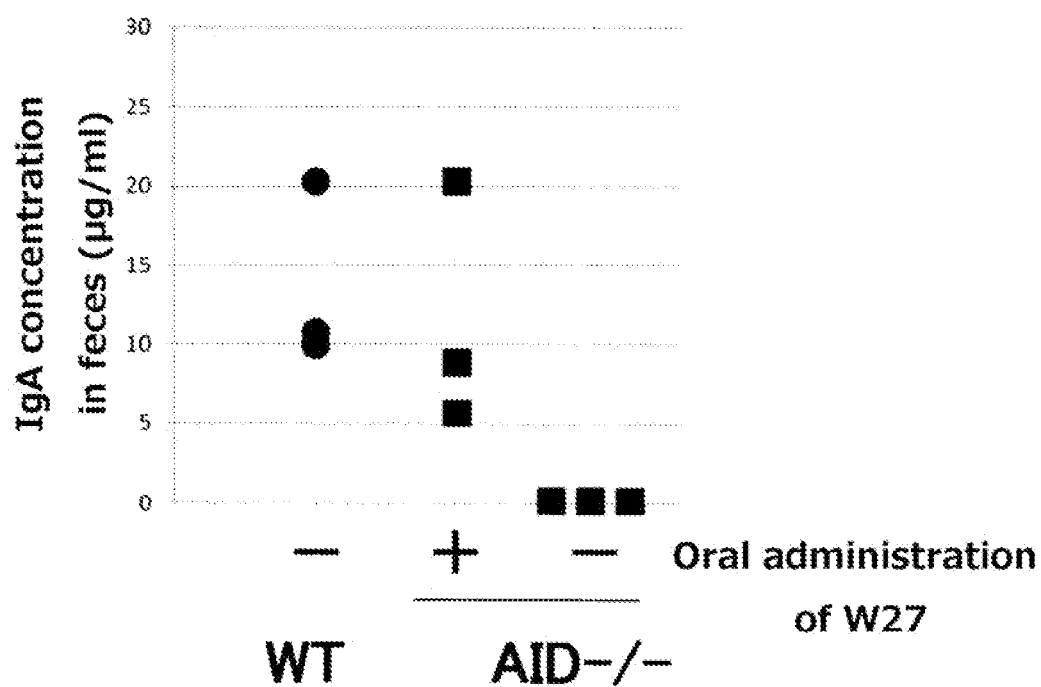

FIG. 8 is a graph showing experimental results to confirm the kinetics in the body when W27 monoclonal IgA antibody was orally administered to mice. The ordinate in the graph indicates the antibody titer (μg/ml) of the IgA antibody in feces.

Figure 9:
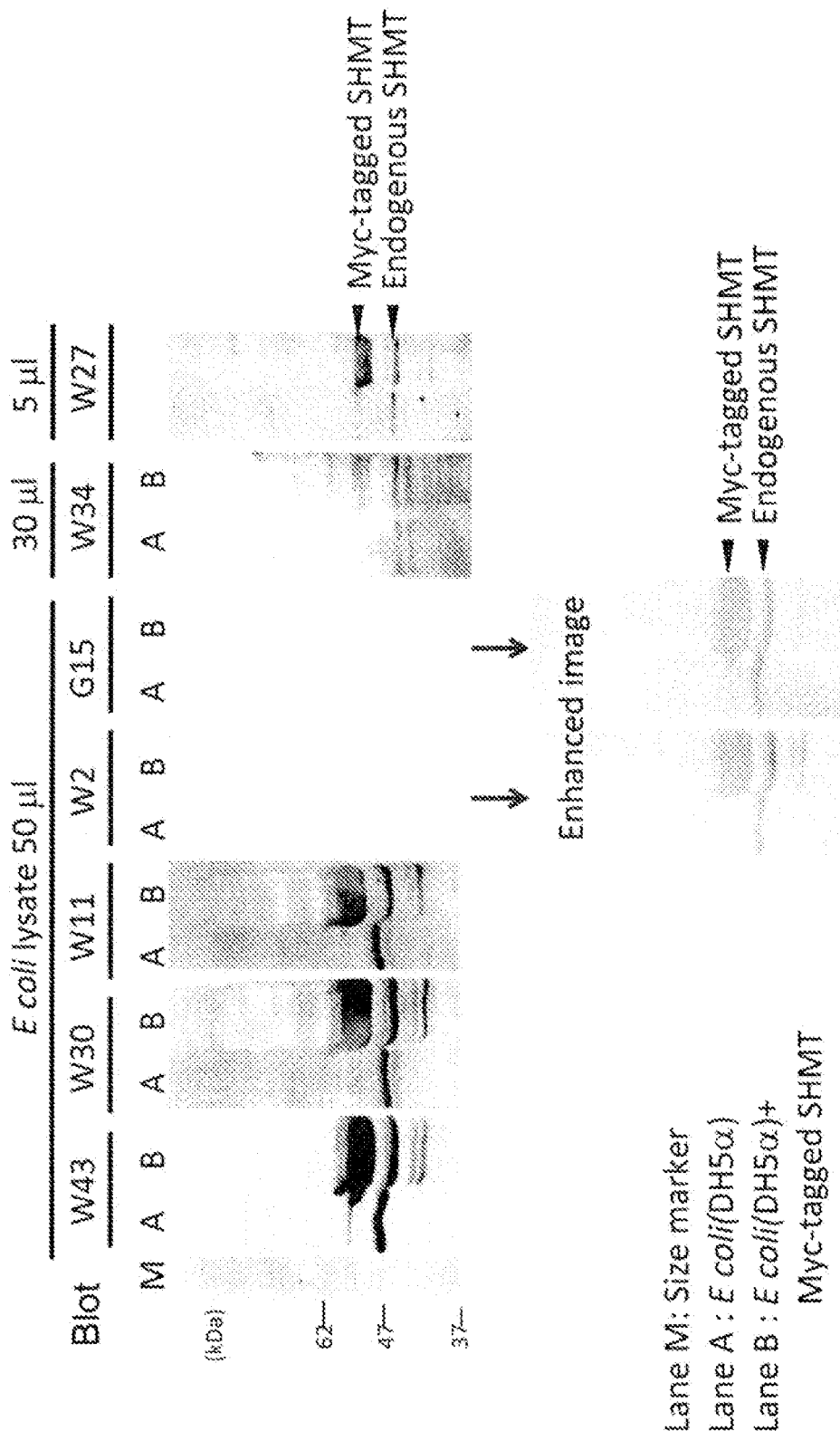

FIG. 9 shows results of Western blotting using various monoclonal IgA antibodies. Most of these poly-reactive IgA antibodies recognize serine hydroxymethyltransferase (SHMT).

Figure 10:
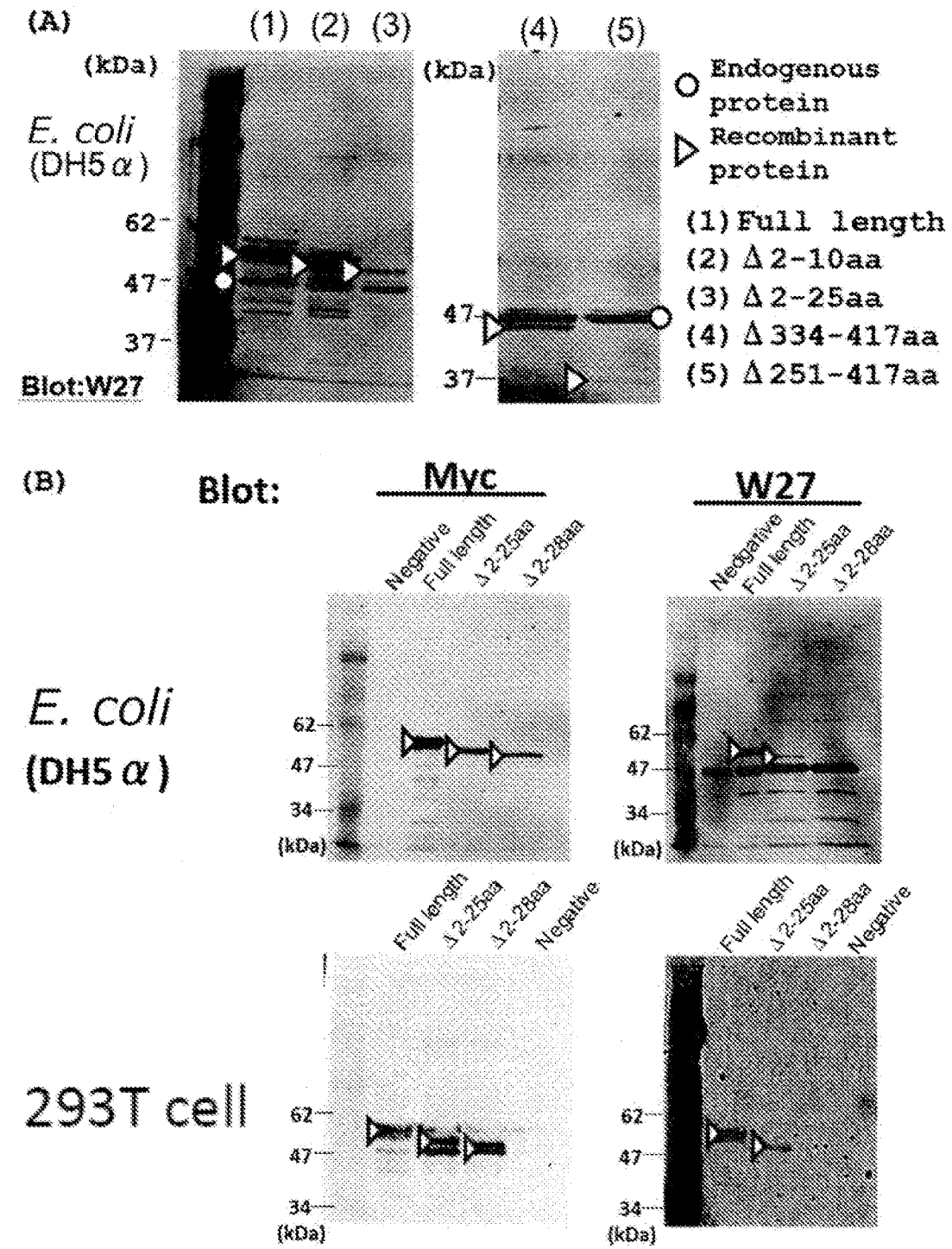

FIG. 10 shows results of an experiment to identify the epitope for various monoclonal IgA antibodies, using various mutants of serine hydroxymethyltransferase.

Figure 11:
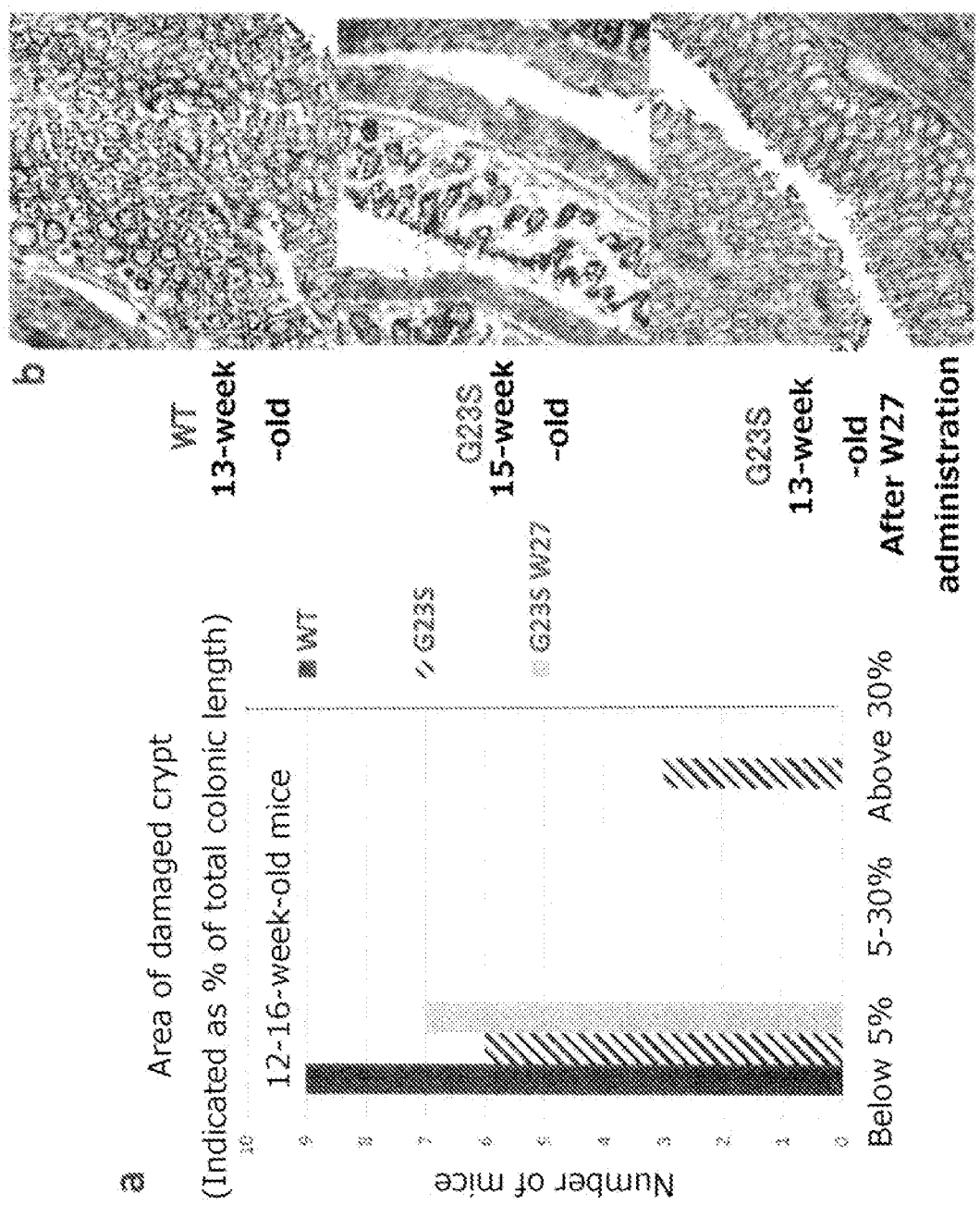

FIG. 11 shows HE-stained sections of the large intestine of G23S mice. This shows the state of the crypts when W27 monoclonal IgA antibody was administered. The atrophy in the crypts observed in the large intestine of G23S mice was normalized by administration of the W27 antibody.

Figure 12:
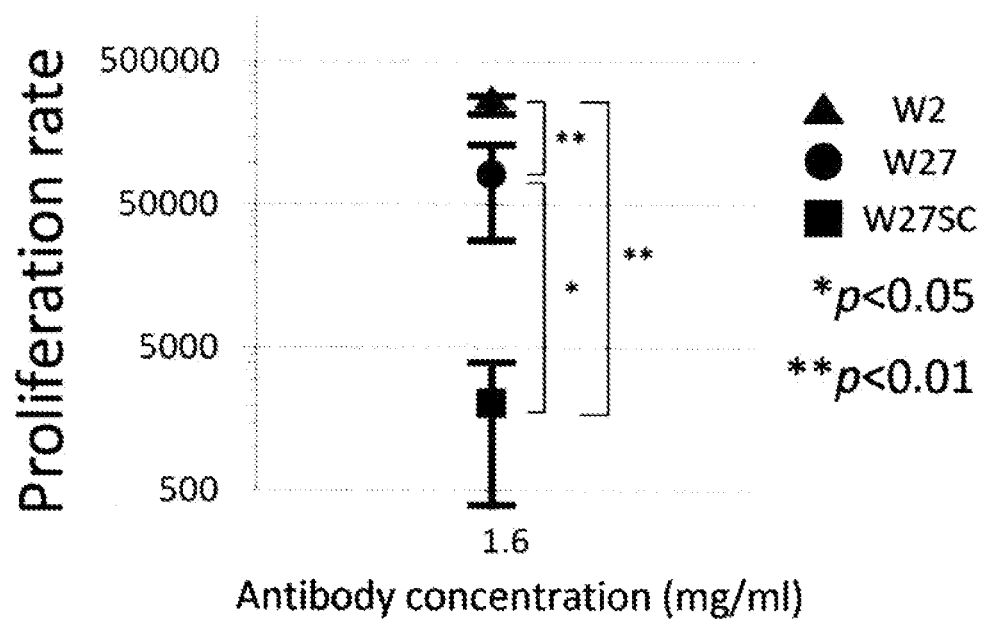

FIG. 12 is a graph showing the effect of the monoclonal IgA antibody of the present invention on *Escherichia coli* growth suppression.

DESCRIPTION OF EMBODIMENTS

Monoclonal IgA Antibody

The monoclonal IgA antibody of the present invention specifically binds to amino acids 11 to 333 of the amino acid sequence of serine hydroxymethyltransferase. The amino acids from either 11 or 25 to any of 28, 37, 44, 250, or 330 (11 to 250, 11 to 44, 11 to 37, 11 to 28, 25 to 333, 25 to 250, 25 to 44, 25 to 37, or 25 to 28) of the amino acid sequence are preferable, and the amino acids 25 to 44 of the amino acid sequence are more preferable, and the amino acids 25 to 28 of the amino acid sequence are most preferable.

Serine hydroxymethyltransferase has a molecular weight of about 45 to 50 kDa and an isoelectric point of about 4.3 to 4.7. Specifically, when it is derived from, for example, *Escherichia coli*, serine hydroxymethyltransferase is a protein consisting of, for example, the amino acid sequence of accession no. J01620 J01621; and version J01620.1 GI: 146216, shown on the NCBI website. More specifically, this protein has the amino acid sequence represented by SEQ ID NO: 74. This protein is an enzyme that functions to reversibly convert L-serine to glycine, and tetrahydrofolic acid to 5,10-methylene tetrahydrofolic acid at the same time. The conformation of this enzyme is highly conserved in *Escherichia coli* and also in mammals.

TABLE 1

| Origine | (Start aa) | -----sequence---- | (end aa) |
|---|---|---|---|
| *Escherichia coli* | 21 | QEKV RQ EEHI ELIASEN YTSPRVM | 44 |
| *Eubacterium rectale* | 20 | DEFE RQ NSHI ELIASEN WVSPAVM | 43 |
| *Pseudomonas fulva* | 21 | QEAL RQ EEHI ELIASEN YTSPAVM | 44 |
| *Staphylococcus aureus* | 17 | REFQ RQ NSNI ELIASEN FVSEAVM | 40 |
| *Bacteroides fragilis* | 13 | KEHQ RQ LKGI ELIASEN EVSDQVM | 36 |
| *Haemophilus influenzae* | 21 | DENR RQ EEHI ELIASEN YASPRVM | 44 |
| *Klebsiella pneumoniae* | 21 | QEKV RQ EEHI ELIASEN YTSPRVM | 44 |
| *Legionella pneumophilia* | 21 | DEKR RQ EEHI ELIASEN YVSPRVL | 44 |
| *Rickettsia rickettsii* | 21 | HEKL RQ SSVI ELIASEN FVSPAVL | 44 |
| *Salmonella paratyphi A* | 21 | QEKV RQ EEHI ELIASEN YTSPRVM | 44 |
| *Salmonella typhimurium* | 21 | OEKV RQ EEHI ELIASEN YTSPRVM | 44 |
| *Shigella flexneri* | 21 | QEKV RQ EEHI ELIASEN YTSPRVM | 44 |
| *Streptococcus pneumoniae* | 21 | KEEE RQ QNNI ELIASEN VVSKAVM | 44 |
| *Yersinia pestis bv. AntiqueM* | 21 | QEVV RQ EEHI ELIASEN YTSPRVM | 44 |
| *Mycobacteirum tuberculosis* | 18 | KELG RQ RDTL EMIASEN FVPRAVL | 41 |
| *Burkholderia mallei* | 22 | QENV RQ EEHI ELIASEN YTSPAVM | 45 |
| *Lactobacillus casei* | 16 | NEEE RQ EHNI ELIASEN IVSPAVR | 39 |
| *Coprococcus eutactus* | 20 | DELN RQ NNNL ELIASEN IVSKAVM | 43 |
| *Bordetella parapertussia* | 12 | AERQ RQ MHSI ELIASEN FVSQAVL | 55 |
| *Saccharomyces cerevisiae* | 46 | QERH RQ KHSI TLIPSEN FTSKAVM | 69 |
| *Schizosaccharomyces pompe* | 47 | SEKS RQ KESI ALIASEN FTSRAVM | 70 |
| *Arabidopsis thaliana* | 96 | KEKD RQ FRSL ELIASEN FTSRAVM | 119 |

TABLE 1-continued

| Origine | (Start aa)-----sequence----(end aa) |
|---|---|
| Rabbit | 62 REKD RQ CRGL ELIASEN FCIRAAL 85 |
| Mouse | 33 KESN RQ RVGL ELIASEN PASRAVL 56 |
| Human | 62 REKD RQ CRGL ELIASEN FCSRAAL 85 |
| *Megamonas hypermegale* | motif not found |
| *Bifidobacterium bifidum* | motif not found |

Table 1 shows the alignment between the amino acids 21 to 44 of the amino acid sequence of *Escherichia coli*-derived serine hydroxymethyltransferase, in which the amino acid sequence of serine hydroxymethyltransferase is represented by SEQ ID NO: 74, and the amino acid sequence of other intestinal bacteria which correspond to amino acids 21 to 44 of the amino acid sequences of *Escherichia coli*-derived serine hydroxymethyltransferase. Amino acids 25 to 26 (RQ), 31 to 44, and, in particular, 31 to 37 (ELIASEN) of *Escherichia coli*-derived serine hydroxymethyltransferase are highly conserved in a large number of the species as shown in Table 1. As described in the Examples below, these amino acid sequences, i.e., amino acids 25 to 26 (RQ) and 31 to 44 of the amino acid sequence of *Escherichia coli*-derived serine hydroxymethyltransferase, are the smallest units of the amino acid sequence that are considered to be included in the epitope of *Escherichia coli*-derived serine hydroxymethyltransferase, to which the monoclonal IgA antibody of the present invention binds. Therefore, the epitope for the monoclonal IgA antibody of the present invention is considered to contain regions corresponding to amino acids 25 to 26 and 31 to 44 of the amino acid sequence represented by SEQ ID NO: 74, in addition to amino acids 25 to 28 of the amino acid sequence.

In addition to *Escherichia coli*, examples of the origins of serine hydroxymethyltransferase which are bound with the monoclonal IgA antibody of the present invention include, but are not particularly limited to, bacteria belonging to the genus *Pseudomonas*, such as *Pseudomonas fulva*; *Staphylococci*, such as *Staphylococcus aureus*; *Eubacterium rectale*, *Haemophilus influenzae*, *Klebsiella pneumoniae*, *Legionella pneumophila*, *Salmonella paratyphi* A, *Salmonella typhimurium*, *Shigella flexneri*, *Yersinia pestis* bv. *Antique*, *Burkholderia mallei*, and the like.

The serine hydroxymethyltransferase that is derived from an origin other than the origins listed as examples above is not bound with monoclonal IgA antibody of the present invention or the antibody tends to dissociate immediately even if the binding between the serine hydroxymethyltransferase and the antibody occurs. Examples of such origins include, but are not particularly limited to, *Lactobacillus casei*, *Bifidobacterium bifidum*, and like *lactobacillus*, *Blautia coccoides*, *Coprococcus eutactus*, *Megamonas hypermegale*, and *Bordetella parapertussis*; *Saccharomyces cerevisiae*, *Schizosaccharomyces pompe*, *Arabidopsis thaliana*, rabbit, mouse, human, and like eukaryotes. The presence or absence of the bond and the binding tendency are confirmed by applying Western blotting using the monoclonal IgA antibody of the present invention to the lysates of various cultured cells.

As described above, the particular site (epitope) of serine hydroxymethyltransferase which is specifically bound with the monoclonal IgA antibody of the present invention may be confirmed, for example, as described in the Examples of the present specification: a truncated mutant of serine hydroxymethyltransferase is produced, and known immunochemistry techniques, such as Western blotting, may be used to confirm whether the monoclonal IgA of the present invention binds to the produced truncated mutant protein.

Alternatively, a mutant may be produced in which a portion of the amino acid sequence of wild-type serine hydroxymethyltransferase derived from, for example, *Escherichia coli* to which the monoclonal IgA antibody of the present invention binds as described above is replaced with an amino acid sequence that corresponds to the portion of the amino acid sequence above and that is a portion of the amino acid sequence of wild-type serine hydroxymethyltransferase derived from, for example, *lactobacillus* in which the portion is not bound with the monoclonal IgA antibody of the present invention or dissociates immediately even if the binding between the portion and the antibody occurs as described above. When the produced mutant protein cannot be bound with the monoclonal IgA antibody of the present invention or shows decrease in binding ability compared to that of wild-type serine hydroxymethyltransferase, the replaced portion of the amino acid sequence may be determined to be the amino acid sequence to which the monoclonal IgA antibody of the present invention specifically binds in the amino acid sequence of the serine hydroxymethyltransferase. To confirm whether the binding occurs, whether the binding ability is deteriorated, and the like, well-known immunochemistry techniques, such as those described above, may be appropriately used.

The term "monoclonal" used in this specification is a modifying word, expressing characteristics of, for example, antibodies obtained from a substantially homogeneous population of antibodies. The individual antibodies in the population of antibodies are identical, except for naturally occurring mutations that may possibly be present in minor amounts.

The monoclonal IgA antibody of the present invention is one type of immunoglobulin. Examples of embodiments of the antibody include antibodies having a heavy chain variable region and/or a light chain variable region. Of these, more preferable embodiments of the antibody include antibodies comprising a heavy chain further having a constant region and/or a light chain further having a constant region. Even more preferable embodiments of the antibody include antibodies comprising a heavy chain and a light chain.

The heavy chain and the light chain are constructed mainly from polypeptide chains, and the heavy chain and the light chain each contain a region called a variable region, which recognizes an antigen. (These regions are usually called a "heavy chain variable region" and a "light chain variable region," respectively.)

The variable region sequentially contains regions called CDRs 1 to 3, which are defined as regions with more particular recognition of antigens, in this order from the amino terminus. More precisely, the CDRs 1 to 3 are also referred to as a heavy chain CDR 1, a heavy chain CDR 2, a heavy chain CDR 3, a light chain CDR 1, a light chain CDR 2, a light chain CDR 3, and the like. Regions other than CDRs 1 to 3 in the heavy chain and the light chain are referred to as heavy chain FRs 1 to 4 and light chain FRs 1 to 4, respectively, in order from the amino terminus.

Neither the heavy chain variable region nor the light chain variable region of the monoclonal IgA antibody of the present invention necessarily contains all of the CDRs 1 to 3, and each may contain at least one CDR, and preferably contain CDR 3.

The amino acid sequences of polypeptides which construct the heavy chain CDRs 1 to 3 and the light chain CDRs 1 to 3 are not particularly limited. Examples are,
for the heavy chain CDR 1, the amino acid sequence represented by any of SEQ ID NOs: 3, 13, 23, 33, or 43;
for the heavy chain CDR 2, the amino acid sequence represented by any of SEQ ID NOs: 4, 14, 24, 34, or 44;
for the heavy chain CDR 3, the amino acid sequence represented by any of SEQ ID NOs: 5, 15, 25, 35, or 45;
for the light chain CDR 1, the amino acid sequence represented by any of SEQ ID NOs: 8, 18, 28, 38, or 48;
for the light chain CDR 2, the amino acid sequence represented by any of SEQ ID NOs: 9, 19, 29, 39, or 49; and
for the light chain CDR 3, the amino acid sequence represented by any of SEQ ID NOs: 10, 20, 30, 40, or 50.

The heavy chain variable region of the monoclonal IgA antibody of the present invention is not particularly limited. Examples of embodiments of the heavy chain variable region containing CDRs 1 to 3 include a heavy chain variable region which sequentially contains the following CDRs 1 to 3:
(1) heavy chain CDR 1 consisting of the amino acid sequence represented by any of SEQ ID NOs: 3, 13, 23, 33, or 43;
(2) heavy chain CDR 2 consisting of the amino acid sequence represented by any of SEQ ID NOs: 4, 14, 24, 34, or 44; and
(3) heavy chain CDR 3 consisting of the amino acid sequence represented by any of SEQ ID NOs: 5, 15, 25, 35, or 45, in this order from the amino terminus.

The light chain variable region containing CDRs 1 to 3 is also not limited. Examples of such an embodiment include a light chain variable region which sequentially contains the following CDRs 1 to 3:
(I) light chain CDR 1 consisting of the amino acid sequence represented by any of SEQ ID NOs: 8, 18, 28, 38, or 48;
(II) light chain CDR 2 consisting of the amino acid sequence represented by any of SEQ ID NOs: 9, 19, 29, 39, or 49; and
(III) light chain CDR 3 consisting of the amino acid sequence represented by any of SEQ ID NOs: 10, 20, 30, 40, or 50, in this order from the amino terminus.

More preferable examples of embodiments of the heavy chain variable region containing CDRs 1 to 3 include a heavy chain variable region which sequentially contains a heavy chain CDR 1 consisting of the amino acid sequence represented by SEQ ID NO: 3, a heavy chain CDR 2 consisting of the amino acid sequence represented by SEQ ID NO: 4, and a heavy chain CDR 3 consisting of the amino acid sequence represented by SEQ ID NO: 5, in this order from the amino terminus;

a heavy chain variable region sequentially containing a heavy chain CDR 1 consisting of the amino acid sequence represented by SEQ ID NO: 13, a heavy chain CDR 2 consisting of the amino acid sequence represented by SEQ ID NO: 14, and a heavy chain CDR 3 consisting of the amino acid sequence represented by SEQ ID NO: 15, in this order from the amino terminus;

a heavy chain variable region sequentially containing a heavy chain CDR 1 consisting of the amino acid sequence represented by SEQ ID NO: 23, a heavy chain CDR 2 consisting of the amino acid sequence represented by SEQ ID NO: 24, and a heavy chain CDR 3 consisting of the amino acid sequence represented by SEQ ID NO: 25, in this order from the amino terminus;

a heavy chain variable region sequentially containing a heavy chain CDR 1 consisting of the amino acid sequence represented by SEQ ID NO: 33, a heavy chain CDR 2 consisting of the amino acid sequence represented by SEQ ID NO: 34, and a heavy chain CDR 3 consisting of the amino acid sequence represented by SEQ ID NO: 35, in this order from the amino terminus; or a heavy chain variable region sequentially containing a heavy chain CDR 1 consisting of the amino acid sequence represented by SEQ ID NO: 43, a heavy chain CDR 2 consisting of the amino acid sequence represented by SEQ ID NO: 44, and a heavy chain CDR 3 consisting of the amino acid sequence represented by SEQ ID NO: 45, in this order from the amino terminus.

An even more preferable heavy chain variable region is a heavy chain variable region which sequentially contains a heavy chain CDR 1 consisting of the amino acid sequence represented by SEQ ID NO: 3, a heavy chain CDR 2 consisting of the amino acid sequence represented by SEQ ID NO: 4, and a heavy chain CDR 3 consisting of the amino acid sequence represented by SEQ ID NO: 5, in this order from the amino terminus.

More preferable examples of the light chain variable region containing CDRs 1 to 3 include a light chain variable region which sequentially contains a light chain CDR 1 consisting of the amino acid sequence represented by SEQ ID NO: 8, a light chain CDR 2 consisting of the amino acid sequence represented by SEQ ID NO: 9, and a light chain CDR 3 consisting of the amino acid sequence represented by SEQ ID NO: 10, in this order from the amino terminus;

a light chain variable region sequentially containing a light chain CDR 1 consisting of the amino acid sequence represented by SEQ ID NO: 18, a light chain CDR 2 consisting of the amino acid sequence represented by SEQ ID NO: 19, and a light chain CDR 3 consisting of the amino acid sequence represented by SEQ ID NO: 20, in this order from the amino terminus;

a light chain variable region sequentially containing a light chain CDR 1 consisting of the amino acid sequence represented by SEQ ID NO: 28, a light chain CDR 2 consisting of the amino acid sequence represented by SEQ ID NO: 29, and a light chain CDR 3 consisting of the amino acid sequence represented by SEQ ID NO: 30, in this order from the amino terminus;

a light chain variable region sequentially containing a light chain CDR 1 consisting of the amino acid sequence represented by SEQ ID NO: 38, a light chain CDR 2 consisting of the amino acid sequence represented by SEQ ID NO: 39, and a light chain CDR 3 consisting of the amino acid sequence represented by SEQ ID NO: 40, in this order from the amino terminus; or a light chain variable region sequentially containing a light chain CDR 1 consisting of the amino acid sequence represented by SEQ ID NO: 48, a light chain CDR 2 consisting of the amino acid sequence represented by SEQ ID NO: 49, and a light chain CDR 3 consisting of the amino acid sequence represented by SEQ ID NO: 50, in this order from the amino terminus.

An even more preferable light chain variable region containing CDRs 1 to 3 is a light chain variable region which sequentially contains a light chain CDR 1 consisting of the amino acid sequence represented by SEQ ID NO: 8, a light chain CDR 2 consisting of the amino acid sequence represented by SEQ ID NO: 9, and a light chain CDR 3 consisting of the amino acid sequence represented by SEQ ID NO: 10, in this order from the amino terminus.

Of the heavy chain variable regions mentioned above, a heavy chain variable region consisting of the amino acid sequence represented by SEQ ID NO: 2, 12, 22, 32, or 42 is more preferable, and a heavy chain variable region consisting of the amino acid sequence represented by SEQ ID NO: 2 is most preferable.

Of the light chain variable regions mentioned above, a light chain variable region consisting of the amino acid sequence represented by SEQ ID NO: 7, 17, 27, 37, or 47 is more preferable, and a light chain variable region consisting of the amino acid sequence represented by SEQ ID NO: 7 is most preferable.

The monoclonal IgA antibody of the present invention may also have a construct in which the heavy chain variable region and/or the light chain variable region described above are appropriately combined. The monoclonal IgA antibody of these other embodiments has a structure called, for example, F(ab')$_2$, Fab, Fv, scFv, scFv-Fc, and minibody.

Examples of more preferable embodiments of the monoclonal IgA antibody of the present invention include a monoclonal IgA antibody in which each of the heavy chain variable region and/or a light chain variable region described above further contains a constant region.

Such monoclonal IgA is not particularly limited. Examples include a monoclonal IgA antibody comprising a heavy chain which consists of the amino acid sequence represented by SEQ ID NO: 1, 11, 21, 31 or 41, and/or a light chain which consists of the amino acid sequence represented by SEQ ID NO: 6, 16, 26, 36, or 46.

A monoclonal IgA antibody comprising a heavy chain which consists of the amino acid sequence represented by SEQ ID NO: 1, 11, 21, 31, or 41, and a light chain which consists of the amino acid sequence represented by SEQ ID NO: 6, 16, 26, 36, or 46 is more preferable.

Even more preferable embodiments include a monoclonal IgA antibody which comprises a heavy chain consisting of the amino acid sequence represented by SEQ ID NO: 1 and a light chain consisting of the amino acid sequence represented by SEQ ID NO: 6;
a monoclonal IgA antibody which comprises a heavy chain consisting of the amino acid sequence represented by SEQ ID NO: 11 and a light chain consisting of the amino acid sequence represented by SEQ ID NO: 16;
a monoclonal IgA antibody which comprises a heavy chain consisting of the amino acid sequence represented by SEQ ID NO: 21 and a light chain consisting of the amino acid sequence represented by SEQ ID NO: 26;
a monoclonal IgA antibody which comprises a heavy chain consisting of the amino acid sequence represented by SEQ ID NO: 31 and a light chain consisting of the amino acid sequence represented by SEQ ID NO: 36;
a monoclonal IgA antibody which comprises a heavy chain consisting of the amino acid sequence represented by SEQ ID NO: 41 and a light chain consisting of the amino acid sequence represented by SEQ ID NO: 46.

Of these, a monoclonal IgA antibody which comprises a heavy chain consisting of the amino acid sequence represented by SEQ ID NO: 1 and a light chain consisting of the amino acid sequence represented by SEQ ID NO: 6 is even more preferable.

The monoclonal IgA antibody of the present invention may be a monomer or a polymer, and preferably a dimer. When the monoclonal antibody is a polymer, the monoclonal antibody contains a J chain described later.

A J chain is a peptide consisting of an amino acid sequence with no antigen-recognition site, and is a peptide consisting of an amino acid sequence different from those of the heavy chains and light chains mentioned above. Specific examples of this amino acid sequence include an amino acid sequence derived from mouse, such as an amino acid sequence of accession no. AAA38673; version AAA38673.1 GI: 196379, shown on the National Center of Biotechnology Information (NCBI) website (http://www.ncbi.nlm.nih.gov/); an amino acid sequence derived from human, such as an amino acid sequence of accession no. NP_653247; version NP_653247.1 GI: 21489959, also shown on the NCBI website; and the like. The monoclonal IgA antibody monomers are connected with a J chain by forming disulfide are bound between each monomer havey chain and the J chain.

The amino acid sequence for the above monoclonal IgA antibody of the present invention may be appropriately mutated to an extent that the functions, effects, etc., of the monoclonal IgA antibody described in this specification are not attenuated. The exact number of introduced mutations is also not particularly limited. Mutations are usually introduced such that the amino acid sequence of the resulting mutant has an identity of 85% or more, preferably 90% or more, more preferably 95% or more, and most preferably 99% or more, with the amino acid sequence before mutation.

The term "identity" used in this specification refers to the degree of identical amino acid sequences or nucleotide sequences among two or more comparable amino acid sequences or nucleotide sequences. Accordingly, when the identity between two amino acid sequences or nucleotide sequences is high, the identity or similarity of these sequences is high. The level of identity between amino acid sequences or between nucleotide sequences is determined using, for example, FASTA, which is a sequence analysis tool, based on default parameters.

Alternatively, level of identity may be determined using the BLAST algorithm by Karlin and Altschul (e.g., Karlin S, Altschul S F, Proc Natl Acad Sci USA. 87: 2264-2268 (1990); and Karlin S. Altschul S F, Natl Acad Sci USA, 90: 5873-7(1993)). Programs such as BLASTN and BLASTX based on the BLAST algorithm described above have been developed (e.g., Altschul S F, Gish W. Miller W, Myers E W, Lipman D J, J Mol Biol, 215: 403-10 (1990)). Detailed procedures for these analytical methods are known, and the detailed procedures may be referred to the website of NCBI.

The term "mutation" used above includes substitution, deletion, insertion, and the like. A known method without particular limitation may be used as a specific method for introducing mutations. For example, conservative substitution may be used for substitution.

The term "conservative substitution" used in this specification refers to a replacement of an amino acid residue with another amino acid residue having a similar side chain.

For example, a conservative substitution refers to a technique of replacement between amino acid residues with basic side chains, such as lysine, arginine, and histidine. A conservative substitution also includes a replacement between amino acid residues with acid side chains, such as aspartic acid and glutamic acid; a replacement between amino acid residues with uncharged polar side chains, such as glycine, asparagine, glutamine, serine, threonine, tyrosine, and cysteine; a replacement between amino acid residues with non-polar side chains, such as alanine, valine, leucine, isoleucine, proline, phenylalanine, methionine, and tryptophan; a replacement between amino acid residues with β-branched side chains, such as threonine, valine, and isoleucine; and a replacement between amino acid residues with aromatic side chains, such as tyrosine, phenylalanine, tryptophan, and histidine.

The subclasses of the monoclonal IgA antibody above are not particularly limited, and may be, for example, $IgA_1$ and $IgA_2$.

The monoclonal IgA antibody of the present invention may contain a secretory component. A secretory component is a peptide containing an amino acid sequence with no antigen recognition site, as with the J chain described above, and is usually a sugar chain-modified peptide containing an amino acid sequence that is different from those of the heavy chains and light chains mentioned above.

A specific example of the amino acid sequence of the secretory component is derived from a mouse. Specific examples of the amino acid sequence of the secretory component include an amino acid sequence which corresponds to an extracellular domain of the amino acid sequence of polyimmunoglobulin receptor of accession no. 070570; version 070570.1 GI: 6225856, shown on the NCBI website, and the like. In the amino acid sequence shown in the accession no. 070570, the amino acids 19 to 638 of the amino acid sequence correspond to the secretory component.

A specific example of the amino acid sequence of the secretory component derived from a human. Examples include an amino acid sequence which corresponds to an extracellular domain of the amino acid sequence of polyimmunoglobulin receptor of accession no. P01833; version P01833.4 GI; 150421625, shown on the NCBI website, and the like. In the amino acid sequence shown in the accession P01833, the amino acids 19 to 645 of the amino acid sequence correspond to the secretory component.

To produce the monoclonal IgA antibody containing the secretory component described above, it is possible to encompass a further step of introducing a nucleic acid having the base sequence encoding the secretory component region of the polyimmunoglobulin receptor into the hybridomas obtained in step 1 above. The detailed methods of the introduction are not particularly limited, and a known method may be appropriately modified.

The monoclonal IgA antibody above may have an amino acid sequence derived from the same species. Alternatively, the monoclonal IgA antibodies above may have amino acid sequences derived from different species. Examples of the origins of the monoclonal IgA antibody from the same species include human, mouse, rat, hamster, rabbit, goat, donkey, pig, cow, horse, chicken, monkey, chimpanzee, and the like.

Examples of the monoclonal IgA antibodies from different species include, but are not particularly limited to, the monoclonal IgA antibodies from at least two species selected from human, mouse, rat, hamster, rabbit, goat, donkey, pig, cow, horse, chicken, monkey, chimpanzee, and the like.

Specific examples of embodiments of the monoclonal IgA antibodies having amino acid sequences derived from different species include the monoclonal IgA antibodies having an amino acid sequence derived from a human, together with an amino acid sequence derived from a non-human animal species. In this monoclonal IgA antibody, the amino acid sequence of the entire heavy chain and light chain variable regions are derived from a non-human animal species while the amino acid sequences of the other regions are derived from a human. This monoclonal IgA antibody is sometimes called, in particular, a chimeric antibody.

The monoclonal IgA antibody of the present invention inhibits the growth of at least two kinds of intestinal bacteria.

The term "intestinal bacteria" used in this specification is not particularly limited as long as they are indigenous bacteria in the intestine of a living body. Examples of the intestinal bacteria include bacteria that form gut microbiota in the living body and that are involved in maintaining homeostasis in the intestinal immune system.

Examples of intestinal bacteria include, but are not particularly limited to,
bacteria belonging to the genus *Prevotella*,
bacteria belonging to the genus *Bacteroides*,
bacteria belonging to the genus *Megamonas*,
bacteria belonging to the genus *Bifidobacterium*,
bacteria belonging to the genus *Faecalibacterium*,
bacteria belonging to the genus *Coprococcus*,
bacteria belonging to the genus *Ruminococcus*,
bacteria belonging to the genus *Blautia*,
bacteria belonging to the genus *Eubacterium*,
bacteria belonging to the genus *Roseburia*,
bacteria belonging to the genus *Lactobacillus*,
bacteria belonging to the genus *Clostridium*,
bacteria belonging to the genus *Escherichia*,
bacteria belonging to the genus *Staphylococcus*,
bacteria belonging to the genus *Enterococcus*,
bacteria belonging to the genus *Pseudomonas*,
bacteria belonging to the genus *Enterorhabdus*, and the like.

In the genus of bacteria listed above, more specific examples include bacteria such as
*Prevotella melaninogenica*,
*Bacteroidetes vulgatus*,
*Megamonas funiformis*,
*Megamonas hypermegale*,
*Bifidobacterium bifidum*,
*Faecalibacterium prausnitzii*,
*Coprococcus eutactus*,
*Ruminococcus obeum*,
*Blautia productus*,
*Blautia coccoides*,
*Eubacterium rectale*,
*Roseburia intestinalis*,
*Lactobacillus murinus*,
*Lactobacillus casei*,
*Clostridium difficile*,
*Escherichia coli*,
*Staphylococcus aureus*,
*Enterococcus faecalis*,
*Pseudomonas fulva*,
*Enterorhabdus mucosicola*, and the like.

The monoclonal antibody of the present invention has an effect of making recovery from the reduction of crypts or the atrophy of crypts in the large intestinal lamina propria, as described in the Examples below. A reduction in the crypts in the large intestinal lamina propria is seen in histopathological findings of an intestinal disease caused by, in particular, alternation of intestinal bacterial growth and/or pathological changes of intestinal bacterial growth in gut microbiota, and is, in general, a chronic pathology often observed in ulcerative colitis.

Therefore, the monoclonal IgA antibody of the present invention is expected to have effects of suppressing alternation of intestinal bacterial growth and/or pathological changes of intestinal bacterial growth in gut microbiota, and is further expected to have effects of treating, for example, intestinal diseases that are caused by alternation of intestinal bacterial growth and/or pathological changes of intestinal bacterial growth in gut microbiota, such as inflammatory bowel disease, ulcerative colitis, Crohn's disease, allergies, asthma, obesity, and autoimmune diseases.

The alternation of intestinal bacterial growth is not particularly limited, and refers to, for example, a state of growth alternation of bacteria that reside in the intestine.

The pathological changes in gut microbiota are not particularly limited, and refer to a state of abnormality in maintaining the homeostasis in the symbiotic relationship with the host, the abnormality being caused by, for example, a change in the species of intestinal bacteria that form gut microbiota and a change in the proportion of each of the intestinal bacterium.

The alternation of intestinal bacterial growth and/or pathological changes of intestinal bacterial growth in gut microbiota are not necessarily limited to a state affected by an intestinal disease, and can also be a state of having a factor for inducing an intestinal disease.

The term "treatment" used in this specification means attainment of desired pharmacological and/or physiological effects. The effects include partially or completely curing a disease and/or adverse effects (e.g., pathologies and symptoms) caused by the disease. These effects also include an effect of inhibiting or delaying the progression of a disease and/or adverse effects (e.g., pathologies and symptoms) caused by the disease; an effect of alleviating pathologies and symptoms (i.e., ameliorating a disease or symptoms, or causing reversal of the progression of a disease or symptoms); and an effect of preventing recurrence of a disease.

The above effects also include an effect of partially or completely preventing the onset of a disease and/or adverse effects (e.g., pathologies and symptoms) caused by the disease in individuals who can possess a predisposition to the disease and/or adverse effects (e.g., pathologies and symptoms) caused by the disease but who have not yet been diagnosed as having the predisposition. Accordingly, the term "treatment" also means "remission," "prevention of recurrence," "prevention of disease," and the like.

As described above, the monoclonal IgA antibody of the present invention is expected to exert excellent effects when used in the treatment of intestinal diseases. These effects are achieved when the monoclonal antibody is administered orally or enterally to an individual. This confirms that the monoclonal IgA antibody of the present invention is useful as an active ingredient of an orally or enterally administered composition or a pharmaceutical composition.

Nucleic Acid

The nucleic acid of the present invention encodes the monoclonal IgA antibody of the present invention. More specifically, the nucleic acid of the present invention has a base sequence encoding the amino acid sequence represented by any one of SEQ ID NOs: 1 to 50. The nucleic acid above may be a ribonucleotide or a deoxyribonucleotide. The form of the nucleic acid is not particularly limited, and may be a single chain or a double chain.

A base sequence encoding one of the amino acid sequences mentioned above is not limited to one kind of nucleic acid base sequence. In accordance with the purpose of the use of the nucleic acid, the base sequence may be determined by appropriately selecting codons coding for the amino acids. As the purpose of the use, for example, the base sequence may be used to express the monoclonal IgA antibody of the present invention in a cell to produce the monoclonal IgA antibody in the cell. In particular, each codon may be selected in consideration of the codon frequency depending to the species of host cell used in the production of the monoclonal IgA antibody.

Such a base sequence may be easily determined in silico by using, for example, a known program. It is also possible for the nucleic acid of the present invention to have a base sequence encoding the amino acid sequence represented by any one of SEQ ID NOs: 1 to 50 that has been mutated as described in detail in the "Monoclonal IgA Antibody" section.

More specific examples of the base sequence include, but are not particularly limited to, the base sequences of SEQ ID NOs: 51 to 60. Table 2 below shows the correspondence between these base sequences and the amino acid sequences of SEQ ID NOs: 1 to 50 shown in the "Monoclonal IgA Antibody" section above.

TABLE 2

|  | Base Sequence | Amino Acid Sequence |
|---|---|---|
| Heavy chain | SEQ ID NO: 51 | SEQ ID NO: 1 |
|  | SEQ ID NO: 52 | SEQ ID NO: 11 |
|  | SEQ ID NO: 53 | SEQ ID NO: 21 |
|  | SEQ ID NO: 54 | SEQ ID NO: 31 |
|  | SEQ ID NO: 55 | SEQ ID NO: 41 |
| Light Chain | SEQ ID NO: 56 | SEQ ID NO: 6 |
|  | SEQ ID NO: 57 | SEQ ID NO: 16 |
|  | SEQ ID NO: 58 | SEQ ID NO: 26 |
|  | SEQ ID NO: 59 | SEQ ID NO: 36 |
|  | SEQ ID NO: 60 | SEQ ID NO: 46 |

Method for Producing Monoclonal IgA Antibody

The method for producing a monoclonal IgA antibody of the present invention is a method for producing the monoclonal IgA described above, and characterized in that the method comprises the following steps 1 and 2.

Step 1

Step 1 is a step of mixing and fusing B cells collected from an intestinal lamina propria with other types of cells to prepare hybridomas.

Step 2

Step 2 is a step of culturing the hybridomas formed in step 1, determining cells that produce an IgA antibody that binds to at least two kinds of intestinal bacteria, and collecting the IgA antibody from the cells.

To obtain a structure in which a heavy chain variable region and/or a light chain variable region is appropriately combined as described below, the method for producing the monoclonal IgA antibody of the present invention may optionally further comprise, after step 2, for example, a step of treatment with an IgA-specific protease or the like, a step of functional group introduction, which enables chemical bond, such as a disulfide bond, and sequentially, a step of chemical bond formation via the functional group.

The following describes in detail step 1 and step 2 of the method for producing the monoclonal IgA antibody of the present invention.

Step 1

Step 1 of the method for producing the monoclonal IgA antibody of the present invention comprises mixing and fusing B cells collected from an intestinal lamina propria with other types of cells to prepare hybridomas.

The B cells used in step 1 are located in the intestinal lamina propria. The B cells are not necessarily limited to those that contain IgA antibody-encoding DNA or mRNA and produce an IgA antibody by translation of the mRNA, as long as they function to produce an IgA antibody. Examples of the B cells include cells in which an IgG antibody, an IgM antibody, and other immunoglobulin subtypes different from IgA antibody are intracellularly class-switched to an IgA antibody so that an IgA antibody is intracellularly produced.

The intestinal lamina propria is not particularly limited as long as it is one of the layers constituting mucosa which present in, for example, the esophagus, stomach, small intestine (including duodenum, jejunum, ileum, etc.), and large intestine (including cecum, colon, rectum, etc.), and as long as the layer is located between the epithelial cell layer and the muscularis mucosae. In particular, an intestinal lamina propria that is present in a small intestine and that contains lymphoid tissues, capillary vessels, lymphatic vessels, and the like, is preferable.

The method of collecting B cells from an intestinal lamina propria is not particularly limited. For example, an intestine is collected, and the obtained intestine after washing is cut open to expose the mucosal layer, followed by shaking in a saline containing EDTA at an appropriate concentration to release and remove epithelial cells. Subsequently, B cells are collected through treatment using a digestive enzyme, such as collagenase, at an appropriate concentration. Other than the method mentioned above, any known method may be used to collect B cells. It is also possible to use commercially available B cells derived from an intestinal lamina propria.

The origin of the intestinal lamina propria, i.e., the origin of the B cells, is not particularly limited. Examples include mouse, rat, hamster, rabbit, goat, sheep, donkey, pig, cow, horse, chicken, monkey, chimpanzee, human, and the like.

The type of cells other than the B cells above (in this specification, sometimes referred to as "other cells") are different from that of the B cells. The other cells are not limited as long as they fuse with the B cells when contact with the B cells and prepare hybridomas, and as long as the prepared hybridomas maintain the function of the B cells, i.e., the function to produce an IgA antibody.

The other cells mentioned above are preferably cells that fuse with the B cells and prepare hybridomas that have an immortalizing function. Specific examples of the other cells are preferably cancer cells which include myeloma cells, which are derived from myeloma. The other cells are preferably myeloma cells.

The origin of the other cells is not particularly limited. Examples include mouse, rat, hamster, rabbit, goat, sheep, donkey, pig, cow, horse, chicken, monkey, chimpanzee, human, and the like.

The term "to fuse" means that the B cells and the other cells are inseparably unified. The term "inseparably" as used herein excludes the phenomenon of cell division, which occurs when the fused cells proliferate. In this specification, the hybridoma are included in an example of fused cells.

The conditions at the time of mixing and fusing are not particularly limited. The conditions usually used in fusing cells may be appropriately used. For example, the conditions used for culturing the B cells or other cells may be appropriately modified and used. Examples of such methods include a method comprising mixing B cells and cells other than the B cells in an appropriate medium to contact each other in the presence of, for example, polyethylene glycol; a method further comprising, after the mixing above, applying electrical stimulation; and a method comprising, after, for example, a method using viruses, such as Sendai virus, incubating the resulting product at 37° C. in 5% carbon dioxide conditions.

The time for fusion is also not particularly limited. The time required for completion of fusion itself may be appropriately set. The completion of fusion may be confirmed by appropriately modifying a known method that is usually used for fusing cells. Examples of such a method include a method of observing the degree of the progress of fusion under a microscope. It is also possible to appropriately select and use a known kit to fuse cells under its usage conditions.

Step 2

Step 2 of the method for producing the monoclonal IgA antibody of the present invention comprises culturing the hybridomas prepared in step 1 above, determining cells that produce an IgA antibody that binds to at least two kinds of intestinal bacteria, and collecting the antibodies from the cells.

Before step 2 of the method of the present invention, the hybridomas obtained in step 1 may be subjected to, for example, a subcloning step, such as a limiting dilution method or the like, in which the subcloning step is usually used in the production of a monoclonal antibody.

The hybridoma that produces an IgA antibody that binds to at least two kinds of intestinal bacteria may be determined, for example, by means of ELISA, EIA, RIA, FLISA, FIA, or the like, or by means of FACS or the like, using an detectable anti-IgA antibody (optionally labeled with, for example, radioisotope, fluorescence, or colorant), as described in the Examples below.

Examples of a specific method for determining the "hybridoma that produces an IgA antibody that binds to at least two kinds of intestinal bacteria" include, but are not particularly limited to, the following two types of methods that use the anti-IgA antibody mentioned above. The two types of methods may also be appropriately used in combination.

The first method for determination is a method which comprises (A) a step of determining, from among the hybridomas obtained in step 1 above, individual hybridomas that each produce an IgA antibody that binds to an intestinal bacterium; and (B) a step of confirming whether the IgA antibody produced by the hybridomas determined in step A binds to other intestinal bacteria different from the intestinal bacterium described above, and determining, from among the hybridomas determined in step A, a hybridoma that produces an IgA antibody that bind to both kinds of the intestinal bacteria.

In this case, for example, when the ELISA method is used, step A may be performed in the following manner: the culture supernatant of the hybridomas obtained in step 1 is sampled, and the sampled culture supernatant is contacted with a first intestinal bacterium, which is immobilized in, for example, a well of a multi-well plate. Subsequently, the hybridoma is determined to be a hybridoma which produces an IgA antibody by confirming the presence of an IgA antibody that binds to the intestinal bacterium using the ELISA method.

Alternatively, step B may be performed in the following manner: the sampled culture supernatant of the hybridomas that are determined in step A to produce an IgA antibody is used as it is, or a culture supernatant of the hybridomas determined as above in step A is sampled again as required, and then the sampled culture supernatant is contacted with another (a second) intestinal bacterium, which is different from the first intestinal bacterium and which is immobilized in, for example, a well of a multi-well plate. Subsequently, the hybridoma is determined to be a hybridoma that produces an IgA antibody that binds to at least two kinds of intestinal bacteria by confirming the presence of an IgA antibody that binds to this intestinal bacterium is confirmed in the sampled product.

Of course, a step or steps similar to step B may be continuously performed using a third or a subsequent intestinal bacterium different from the first and the second bacteria, as the other intestinal bacteria mentioned above after step B.

When a means such as EIA, RIA, FLISA, or FIA is used, as with the ELISA method described above as an example, a first and a second (and optionally a third and a subsequent) intestinal bacteria may be immobilized in each well or on an experimental apparatus similar to a well plate.

When the FACS method is selected, the following procedures may be applied: the sampled culture supernatant is mixed with a variety of intestinal bacteria; thereafter, the resulting mixture is further contacted with an anti-IgA antibody. Subsequently, the hybridoma is determined to be the hybridoma which produces an IgA antibody that binds to intestinal bacteria by detecting the formations of complexes of the variety of intestinal bacteria, IgA antibodies that bind to the variety of intestinal bacteria, and anti-IgA antibodies, using FACS analysis in an appropriate manner.

Examples of the second method for determination include a method which determines a hybridoma that produces an IgA antibody that binds to at least two kinds of intestinal bacteria, from among the hybridomas obtained in step 1 above, using systems which detect the binding of the IgA antibody to each intestinal bacterium.

Regarding the above, when, for example, a means using the ELISA method is used, the following may be given as an example method: in step A in the first method above, two (optionally three or more) different kinds of intestinal bacteria are immobilized in, for example, different two (or three or more depending on the number of the kinds of intestinal bacteria) wells of a multi-well plate, the sampled culture supernatant of the hybridomas obtained in step 1 is contacted with two (or three or more) different intestinal bacteria in each well. Subsequently, the hybridoma is determined as a hybridoma which produces IgA that binds to at least two kinds of intestinal bacteria by confirming the presence of IgA that binds to both of the two kinds (or all of the three or more kinds) of intestinal bacteria using the ELISA method.

When a means such as EIA, RIA, FLISA, or FIA is used, as in the case when ELISA is used, the first and the second (optionally the third and subsequent) intestinal bacteria may be immobilized in each of wells or on an experimental apparatus similar to a well plate.

When the FACS method is selected, each sampled product is mixed with each kinds of intestinal bacteria, and the resulting mixture is further contacted to an anti-IgA antibody. Subsequently, the hybridoma is determined to be the hybridoma which produces an IgA antibody that binds to intestinal bacteria by detecting the formations of complexes of the variety of intestinal bacteria, IgA antibodies that bind to the variety of intestinal bacteria, and anti-IgA antibodies in an appropriate manner.

After a hybridoma that produces an IgA antibody that binds to at least two kinds of intestinal bacteria is determined in accordance with the method described above, a step which comprises cloning the hybridoma that produces an IgA antibody that binds to at least two kinds of intestinal bacteria, by using, for example, a limiting dilution used in the method for producing the monoclonal antibody described above may be preformed.

When the cloning is performed, the above step of determining the hybridoma may be repeatedly performed using two particular kinds of intestinal bacteria that are the same as those used to determine the hybridoma that produces an IgA antibody that binds to at least two kinds of intestinal bacteria.

The collection method in step 2 is not particularly limited in detail. Examples of the collection method include a method of collecting a supernatant of the culture medium of cells that produce an IgA antibody, and a method of collecting a lysate of the cells. The lysate of the cells may be obtained by cell-lysis suitably using a combination of a known mechanical means, such as sonication and French press, and/or a known chemical treatment method using a detergent, a cell wall-digesting enzyme, and a cellular membrane-digesting enzyme. Thereafter, the liquid phase fractions obtained after a solid-liquid-separation step are collected, and the monoclonal IgA antibody of the present invention may be produced.

Before collecting IgA from the hybridoma, the hybridoma may be cultured in an appropriate medium for a specific period of time, and then, the method of collecting its supernatant or the method of collecting IgA from a lysate of the cells may be performed as described above. Alternatively, the collection may be performed by intraperitoneal administration of the hybridoma to an individual animal that is capable of being transplanted with the origin of this hybridoma, such as an immunodeficient mouse, and collecting IgA from the ascites of the individual.

The monoclonal IgA antibody collected in the above manner may be appropriately subjected to a known purification step. The purification means is not particularly limited in detail. Known protein purification means, such as purification by precipitation using, for example, acetone and ammonium sulfate, and purification by, for example, affinity, anion-exchange, cation-exchange, size exclusion, or reversed-phase column chromatography, may be appropriately combined and used.

Examples of embodiments of the method for producing the monoclonal IgA antibody of the present invention also include a method which comprises introducing the nucleic acid described in detail in the "Nucleic Acid" section above into a cell which is capable of producing a monoclonal IgA antibody, culturing the cell, and collecting a monoclonal IgA antibody from the cell extract or culture supernatant, optionally followed by purification.

The cell which is capable of producing a monoclonal IgA antibody is not particularly limited as long as it is a cell that is capable of producing various proteins that usually function when folded into a higher-order structure from a mammal. The cell may be appropriately selected from known cells, including mammal-derived cells, such as COS cells, HEK cells, HELA cells, and CHO cells, and insect-derived cells, such as Sf9.

The detailed method for introducing a nucleic acid, the conditions for culturing cells into which the nucleic acid is introduced, the collection method, and the purification method are not particularly limited, and vary depending on, for example, the type of the cells used. Known methods may be appropriately modified and combined to produce the monoclonal IgA antibody of the present invention.

Regarding the nucleic acid described above, when the monoclonal IgA antibody of the present invention is a chimeric antibody, a nucleic acid having a base sequence encoding a heavy chain variable region and a nucleic acid having a base sequence encoding a heavy chain constant region of different species, as well as a nucleic acid having a base sequence encoding a light chain variable region and a nucleic acid having a base sequence encoding a light chain constant region of different species are produced. Next, the produced nucleic acid having a base sequence encoding a heavy chain variable region is bound to the nucleic acid having a base sequence encoding a heavy chain constant region, and the nucleic acid having a base sequence encoding a light chain variable region is bound to the nucleic acid having a base sequence encoding a light chain constant region. Then, the resulting nucleic acids may be introduced into a cell that is capable of producing the monoclonal IgA antibody as described above.

The monoclonal IgA antibody of the present invention may also be an antibody in which the heavy chain and/or light chain CDRs 1 to 3 have mouse-derived amino acid sequences while regions other than the CDRs have human-derived amino acid sequences (this antibody sometimes being referred to as a "humanized antibody"). This humanized antibody may be produced as is the case for a chimeric antibody as described above. The nucleic acids having base sequences encoding heavy chain and/or light chain CDRs 1 to 3, and nucleic acids having base sequences encoding the regions other than the CDRs are produced. Next, the nucleic acids having base sequences encoding heavy chain and CDRs 1 to 3 are again bound to regions other than the CDRs and the nucleic acids having base sequences encoding light chain and CDRs 1 to 3 are again bound to regions other than the CDRs to obtain nucleic acids encoding a heavy chain and a light chain. Then, the resulting nucleic acids are introduced into a cell that is capable of producing the monoclonal IgA antibody as described above. To maintain the binding ability of an antibody, replacement of some bases with other bases may be required.

When the monoclonal IgA antibody of the present invention contains a J chain, the monoclonal IgA antibody of the present invention may be produced by introducing a nucleic acid having a base sequence encoding the monoclonal IgA antibody and a nucleic acid having a base sequence encoding J chain into a cell that is capable of producing a monoclonal IgA antibody, as described above.

The base sequence encoding the J chain may be appropriately determined by using a known method, based on the J chain amino acid sequence shown on the NCBI website, as described in the "Monoclonal IgA Antibody" section above. The nucleic acid may be produced using a known method, based on the determined base sequence.

When the monoclonal IgA antibody of the present invention contains a secretory component, the monoclonal IgA antibody of the present invention may be produced by introducing a nucleic acid having a base sequence encoding the monoclonal IgA antibody and a nucleic acid having a base sequence encoding the J chain, as well as a nucleic acid having a base sequence encoding a secretory component, into a cell which is capable of producing a monoclonal IgA antibody, as described above. Such a method is disclosed in, for example, Li C et al., Sheng Wu Gong Cheng Xue Bao. 2011 February; 27(2): 219-25. The monoclonal IgA antibody containing a secretory component of the present invention may be produced based on this disclosure or by appropriately modifying the disclosure.

The nucleic acid base sequence encoding a secretory component may be appropriately determined by using a known method based on the amino acid sequence of, for example, a polyimmunoglobulin receptor shown on the NCBI website, as described in the "Monoclonal IgA Antibody" section above. The nucleic acid may be produced using a known method, based on the determined base sequence.

Hybridoma

The hybridoma of the present invention produces the monoclonal IgA antibody of the present invention.

Hybridomas are specifically those obtained in step 1 described in the "Method for Producing Monoclonal IgA Antibody" section above, i.e., cells obtained by mixing and fusing the B cells with other types of cells, which are cells other than the B cells, as described in step 1 of the method for producing the monoclonal IgA antibody of the present invention.

The hybridoma may be derived from the same species or different species. In the "Method for Producing Monoclonal IgA Antibody" section above, hybridomas derived from the same species may be obtained by arranging the origin of the B cells to be the same as the origin of cells other than the B cells, and hybridomas derived from different species may be obtained by arranging the origin of the B cells to be different from the origin of cells other than the B cells.

To obtain a hybridoma derived from the same species, the origin of the B cells and the origin of cells other than the B cells are appropriately selected, for example, from among the origins mentioned in relation to step 1 described in the "Method for Producing Monoclonal IgA Antibody" section above so that their origins overlap with each other. Examples of the origins of the hybridoma derived from the same species include human, mouse, rat, hamster, rabbit, goat, donkey, pig, cow, horse, chicken, monkey, chimpanzee, and the like.

To obtain a hybridoma derived from different species, the origin of the B cells and the origin of cells other than the B cells may be appropriately selected, for example, from among the origins mentioned in relation to step 1 described in the "Method for Producing Monoclonal IgA Antibody" section above, and combined. Examples of the origins of the hybridoma derived from different species include human, mouse, rat, hamster, rabbit, goat, donkey, pig, cow, horse, chicken, monkey, chimpanzee, and the like.

Pharmaceutical Composition

The pharmaceutical composition of the present invention contains the monoclonal IgA antibody of the present invention.

The pharmaceutical composition of the present invention is not particularly limited, and is suitably used for the treatment of, for example, an intestinal disease. The pharmaceutical composition of the present invention is more preferably used for treating an intestinal disease caused by alternation of intestinal bacterial growth and/or pathological changes of intestinal bacterial growth in gut microbiota. The alternation of intestinal bacterial growth and/or pathological changes of intestinal bacterial growth in gut microbiota are as described in the "Monoclonal IgA Antibody" section above.

The intestinal disease caused by alternation of intestinal bacterial growth and/or pathological changes of intestinal bacterial growth in gut microbiota is not particularly limited. Examples include inflammatory bowel disease, ulcerative colitis, Crohn's disease, allergies, asthma, obesity, autoimmune diseases, and the like. Inflammatory bowel disease is preferable among them.

The pharmaceutical composition of the present invention is sufficient if it contains an effective amount of the monoclonal IgA antibody of the present invention. For example, the amount of the antibody of the present invention contained in 100 wt % of the pharmaceutical composition may be appropriately set to be within a range of 0.001 to 99.99 wt %, in consideration of, for example, the type of the target intestinal disease, the dosage form, the administration method, the target for administration, the degree of symptoms of the target for administration, and the degree of the effect achieved by the administration.

The term "effective amount" used in this specification refers to an amount that allows the monoclonal IgA antibody of the present invention to exert the effect of treating an intestinal disease, or an amount that allows the desired pharmacological and/or physiological effects (intestinal disease treatment effect) described above to be achieved.

Pharmaceutically acceptable carriers or additives may be incorporated in the pharmaceutical composition of the present invention, together with the monoclonal IgA antibody of the present invention. The phrase "pharmaceutically acceptable carriers or additives" used herein refers to optional carriers, diluents, excipients, suspending agents, lubricants, adjuvants, vehicles, delivery systems, emulsifiers, disintegrants, absorbents, preservatives, detergents, colorants, fragrances, or sweeteners. Known carriers or additives may be used.

The pharmaceutical composition of the present invention is applicable to methods of treating an intestinal disease, comprising administering the composition to an individual suffering from the intestinal disease mentioned above. The pharmaceutical composition of the present invention is also applicable to methods of preventing an intestinal disease, in which the methods comprise administering the composition to an individual who has not yet developed pathologies or symptoms of the intestinal disease described above but can possess a predisposition to the intestinal disease. These individuals may be used as the target for administration of the pharmaceutical composition of the present invention.

The individuals used as the target for administration are not particularly limited. Examples include human, mouse, rat, guinea pig, rabbit, hamster, dog, cat, weasel, and the like.

The dosage and administration method of the pharmaceutical composition may be suitably determined according to the type of intestinal disease from which an individual as the target for administration suffers, the sex, the race, the age, the general conditions, the severity of the disease, and the degree of desired effects, and the like. The dosage may be suitably set within a range of 0.001 to 100 mg/kg/day.

The administration method is not particularly limited. Direct administration to the gastrointestinal tract is preferable. Examples of the administration method include oral administration, nasal administration, mucosal administration, enteral administration, and the like.

The enteral administration is not limited to administration through the anus. For example, the enteral administration includes administration through a tube or the like inserted into the gastrointestinal tract from outside the individual, as in gastrostoma. The site in the digestive tract into which a tube is inserted is not limited, and may be, for example, the esophagus, stomach, small intestine (including the duodenum, jejunum, ileum, etc.), large intestine (including the cecum, colon, rectum, etc.), and the like.

The pharmaceutical composition of the present invention in the above dosage may be administered in a single dose or in a plurality of doses per day. The administration interval may be every day, every other day, every week, every other week, every 2 to 3 weeks, every month, or every 2 to 3 months, as long as the effect of the treatment for the above disease is achieved.

Orally or Enterally Administered Composition

The orally or enterally administered composition of the present invention contains the monoclonal IgA antibody of the present invention. The use of the orally or enterally administered composition achieves the effect of suppressing alternation of intestinal bacterial growth and/or pathological changes of intestinal bacterial growth in gut microbiota. The alternation of intestinal bacterial growth and pathological changes of intestinal bacterial growth in gut microbiota are as described in the "Monoclonal IgA Antibody" section above.

The mixing ratio of the monoclonal IgA antibody contained in the orally or enterally administered composition is not particularly limited, and may be appropriately adjusted according to the form, usage, and the like of the orally or enterally administered composition. The mixing ratio may be usually about 0.001 to 99 wt % based on the total amount of the orally or enterally administered composition.

The individuals as a target in which the orally or enterally administered composition of the present invention is used are not particularly limited. Examples include human, mouse, rat, guinea pig, rabbit, hamster, dog, cat, weasel, and the like.

As described above, the monoclonal IgA antibody contained in the orally or enterally administered composition of the present invention has an effect of suppressing alternation of intestinal bacterial growth and/or pathological changes of intestinal bacterial growth in gut microbiota, and is thus particularly useful as a composition that controls intestinal function, a composition that improves the intestinal environment, a composition that optimizes the intestinal environment, or a composition that prevents intestinal putrefaction.

The dosage of the orally or enterally administered composition of the present invention is not particularly limited as long as it is within a range that allows the effects of the orally or enterally administered composition to be exerted, and may be set according to the species of individual who takes the orally or enterally administered composition, the target effect, the target degree of achieving the effect, other various conditions, and the like. Specifically, the dosage may be converted into the amount of the monoclonal IgA antibody of the present invention, which is usually about 0.001 to 100 mg/kg/day. The amount may be taken in a single portion or several portions per day.

The enteral administration is not limited to administration through the anus, as described in the "Pharmaceutical Composition" section above. For example, the enteral composition of the present invention may be blended with a known component so as to be used as intestinal lavage fluid.

The orally or enterally administered composition of the present invention contains the monoclonal IgA antibody of the present invention, which achieves the effect of suppressing alternation of intestinal bacterial growth and/or pathological changes of intestinal bacterial growth in gut microbiota. With the expectation of achieving such effects, the orally or enterally administered composition of the present invention may be suitably used in the fields of food or feed. Therefore, the orally or enterally administered composition of the present invention may be used as a food composition or a feed composition.

As a food composition, the orally or enterally administered composition of the present invention is most suitably used in the field of food. Such a food composition may be provided as a food composition indicated as controlling intestinal function, improving the intestinal environment, optimizing the intestinal environment, preventing intestinal putrefaction, or the like.

In addition to common food products, examples of the food composition include food for specified health use, including conditional food for specified health use, nutrition supplement food, functional food, medical food, and the like.

The specific form of the food composition is not particularly limited. Examples include drinks, such as soft drinks, carbonated drinks, energy drinks, fruit drinks, lactic-acid drinks, and milk drinks; frozen desserts, such as ice cream, ice sherbet, and shaved ice; confectionaries, such as candies, gum, chocolate, tablet candies, snack confectioneries, biscuits, jelly, jam, cream, baked confectioneries; noodles, such as buckwheat noodles, wheat-flour noodles, bean vermicelli, Chinese-style noodles, and instant noodles; fish or livestock processed food, such as kamaboko (fish sausage), ham, and sausage; dairy products, such as processed milk products and fermented milk products; oil- and fat-processed food products, such as salad oil, tempura oil, margarine, mayonnaise, shortening, whipped cream, and dressing; seasonings, such as dipping sauce and other sauces; and soups, stews, salads, daily dishes, rice seasonings, pickles, bread, cereal, and the like. The form of food for specified health use, nutrition supplement food, functional food, or the like, may be a powder, granules, a capsule, a lozenge, a tablet, a syrup, or the like.

As the feed composition, the orally or enterally administered composition of the present invention is most suitably used in the field of feed. Such a feed composition may be provided as a feed composition indicated as controlling intestinal function, improving the intestinal environment, optimizing the intestinal environment, preventing intestinal putrefaction, or the like.

The specific form of the feed composition is not particularly limited, and may be, for example, mixed with usual feed, optionally with a component that can be blended with usual feed, to obtain a feed composition, as long as the effect of the feed composition of the present invention described above is achieved. It is also possible to use the feed composition unmodified as feed.

Method for Treating a Disease

The method for treating a disease according to the present invention is a method for treating an intestinal disease, in which the method comprises administering an effective amount of the monoclonal IgA antibody of the present invention, the pharmaceutical composition of the present invention, or the orally administered composition of the present invention to a human suffering from an intestinal disease.

The human suffering from an intestinal disease may be a target for administration mentioned in the "Pharmaceutical Composition" section above. The specific administration method and dosage amount may also be as described in the "Pharmaceutical Composition" section above.

EXAMPLES

The present invention is described below in more detail but is, of course, not limited to the following Examples.

Example 1

Preparation of Antibodies 1-1: Separation of Intestinal Lamina Propria Cells 8-week-old wild-type C57BL/6 mice (CLEA Japan, Inc.) were fed until the age of 20 weeks with free access to food and water in an experiment facility of the Nagahama Institute of Bio-Science and Technology. Subsequently, the mice were euthanized with carbon dioxide and then subjected to laparotomy to remove the entire length of the small intestine. After the connective tissue and Peyer's patches were removed from the removed small-intestine sample, a longitudinal incision was made through the small intestine, and the intestinal contents were washed out in a 10-cm dish filled with PBS. The small intestine was washed well with three to four changes of PBS.

As with the wild-type C57BL/6 mice, the small intestine was also collected from mice expressing AID G23S (AID G23S mice), in which a mutation is introduced at the N-terminal side of AID protein. Such AID G23S mice can be created using a known method, for example, disclosed in Non-patent Literature 18.

Next, 50 ml of PBS containing 1 mM EDTA was placed into a 50-ml tube. The washed small intestine was cut into lengths of 0.5 to 1 cm and added into the tube. After shaking at 37° C. for 20 minutes, the small-intestine fragments were collected in a strainer, and PBS was then discarded. Further, the small-intestine fragments were placed into a tube as described above. After vigorous shaking for 10 seconds, the small-intestine fragments were collected in a strainer again, and PBS was then discarded in the same manner. This vigorous shaking of the small intestine with 50 ml of PBS for 10 seconds was repeated twice.

Thereafter, 50 ml of a digestive-enzyme solution (prepared using 500 ml of RPMI 1640, 25 ml of FCS (final concentration of 5%), 2 μl of 2-mercaptoethanol (final concentration of 55 μM), 0.75 g of collagenase, and 5 ml of dispase (final concentration of 1 U/ml)) warmed at 37° C. was placed into a 50-ml tube. The small-intestine fragments were further cut into pieces with scissors and added into the tube. After shaking at 37° C. for 60 minutes, the tube was allowed to stand for 10 seconds to allow the small-intestine tissue to sink. The supernatant was then transferred to a new 50-ml tube. This digestion process using the digestive-enzyme liquid was performed twice.

The supernatant separated in the digestion process was centrifuged at 1,500 rpm at 4° C. for 5 minutes, and the supernatant was discarded. The resulting precipitate was further suspended in 1 ml of RPMI 1640 containing 2% FCS. The suspension was passed through a filter to remove tissue fractions, and the resulting suspension of cells was stored on ice.

After the second enzyme reaction described above was performed for 60 minutes, the suspension of cells was collected in the same manner. The two suspensions of cells, i.e., the suspension of cells obtained after the first enzyme reaction and the suspension of cells obtained after the second enzyme reaction were combined, and the resulting suspension was used as intestinal lamina propria cells.

Preparation of IgA-producing Hybridomas

The intestinal lamina propria cells obtained in the Separation of Intestinal Lamina Propria Cells section above were fused with mouse myeloma NS1 cells to prepare hybridomas. Culture and maintenance of the NS1 cells were conducted before the cell fusion. The cell fusion was performed using the reagents of a ClonaCell (registered trademark)-HY Hybridoma Cloning Kit provided from STEMCELL Technologies according to the protocol of the kit.

The obtained hybridomas were then grown in a medium containing methylcellulose to perform cloning according to the protocol of the kit. Thereafter, the supernatants derived from each subclone were isolated from the growing hybridomas. For the antibodies contained in the supernatants, ELISA was performed to detect whether the produced antibodies were IgA, to measure the IgA antibody titer in the supernatants. Then, IgA-producing hybridoma clones were isorated. As a result, it was confirmed that a total of 37 clones were established.

RNA was extracted from each clone by IsogenII (Nippon Gene Co., Ltd.), and cDNA was synthesized using the RNA as a template. Then, RT-PCR was performed using seven primers for antibody Vh region (MH1 to MH7) and a Ca region-specific primer (IgAR). Table 3 shows the detailed base sequences of these primers.

TABLE 3

| Primer Name | Base Sequence |
| --- | --- |
| MH1 (SEQ ID NO: 61) | SARGTNMAGCTGSAGTC |
| MH2 (SEQ ID NO: 62) | SARGTNMAGCTGSAGSAGTCWGG |
| MH3 (SEQ ID NO: 63) | CAGGTTACTCTGAAAGWTSTG |
| MH4 (SEQ ID NO: 64) | GAGGTCCARCTGCAACARTC |
| MH5 (SEQ ID NO: 65) | CAGGTCCAACTVCAGCARCC |
| MH6 (SEQ ID NO: 66) | GAGGTGAASSTGGTGGAATC |
| MH7 (SEQ ID NO: 67) | GATGTGAACTTGGAAGTGTC |
| IgAR (SEQ ID NO 68) | GATGGTGGGATTTCTCGCAGAC |

In the base sequences shown in Table 3, S indicates G or C; R indicates A or G; N indicates A, C, G, or T; M indicates A or C; W indicates A or T; and V indicates G, C, or A.

The amplified PCR products of the VDJ region were directly sequenced to analyze the number of variations and VDJ usage. The analysis revealed that 17 kinds of IgA-producing hybridomas were obtained as independent clones. These are respectively referred to as W1, W2, W3, W4, W6, W7, W11, W14, W24, W27, W28, W30, W32, W34, W37, W43, and W47.

Ten independent clones of IgA-producing hybridomas were obtained from G23S mice by performing an experiment in the same manner. These are respectively referred to as G1, G8, G9, G10, G12, G14, G15, G16, G18, and G19.

1-2: Preparation of IgA Antibodies

The 27 clones of IgA antibody producing hybridomas obtained in the Preparation of IgA-producing Hybridomas section above were individually cultured on a large scale in RPMI 1640 containing 10% FCS, and the culture supernatants were collected by centrifugation. Subsequently, the obtained culture supernatants were passed through a 0.22-μm filter and then subjected to ammonium sulfate precipitation and dialysis against PBS, thereby partially purifying 27 kinds of monoclonal IgA antibodies (also referred to in the Example that follows as "monoclonal IgA antibodies," preceded by the clone name).

In another method, each of the 27 clones of hybridomas obtained in the Formation of IgA-producing Hybridomas section was individually injected intraperitoneally into immunodeficient mice and bred for 10 to 21 days, and then ascites was collected from the mice. After the collected ascites was subjected to ammonium sulfate precipitation, the buffer was replaced with PBS using a PD-10 column. 27 kinds of monoclonal IgA antibodies were also thereby partially purified.

The concentration of each of the 27 kinds of monoclonal IgA antibodies prepared by the methods described above were measured with ELISA. In the measurement, goat anti-mouse IgA (Southern Biotech) was used as an antibody for coating onto a solid phase in an amount of 2 μg/ml, and ALP-labeled goat anti-mouse IgA (Southern Biotech) was used as an antibody for detection in an amount of 0.5 μg/ml. Mouse IgA κ (Immunology Consultants Laboratory) was used as a standard sample.

1-3: Preparation of Indigenous Intestinal Bacteria

After feces of wild-type mice kept in the SPF room of the experiment facility of the Nagahama Institute of Bio-Science and Technology were suspended in PBS, the diluted suspension was spread on a blood agar plate and cultured at 37° C. for 48 to 72 hours. Thereafter, PCR of 16S rRNA gene was directly performed from the obtained colonies. The resulting PCR products were sequenced to identify the bacteria of each colony. Six species of mouse intestinal bacteria were cloned in this manner.

The cloned indigenous intestinal bacteria of the mice are specifically the following six species of bacteria:
Enterorhabdus mucosicola;
Escherichia coli;
Staphylococcus aureus;
Lactobacillus murinus;
Enterococcus faecalis;
Pseudomonas fulva.

1-4: Investigation of Binding Ability and Specificity for Intestinal Bacteria

A total of 13 species of intestinal bacteria, i.e., the six cloned species of indigenous intestinal bacteria described above and the following commercially available bacteria were cultured in optimal conditions, and the bacterial cells were collected by centrifugation: Escherichia coli (DH5α strain: obtained from TOYOBO Co., Ltd.), Lactobacillus casei (obtained from ATCC), Coprococcus eutactus (obtained from ATCC), Blautia coccoides (obtained from ATCC), Megamonas hypermegale (obtained from ATCC), Eubacterium rectale (obtained from ATCC), and Bifidobacterium bifidum (obtained from ATCC).

Specifically, each species of bacteria was suspended in 0.05 M Na$_2$CO$_3$ buffer and individually an ELISA plate was coated with each bacterial solution. After blocking by a known method, the 27 kinds of monoclonal IgA antibodies described above (concentration of 1.4 μg/ml) were individually added to measure the binding ability and specificity of these monoclonal IgA antibodies against the 13 species of intestinal bacteria. Then, the binding between the bacteria and the antibodies was detected according to the known ELISA method. The antibody used for detection was the same as above.

Figure 1:
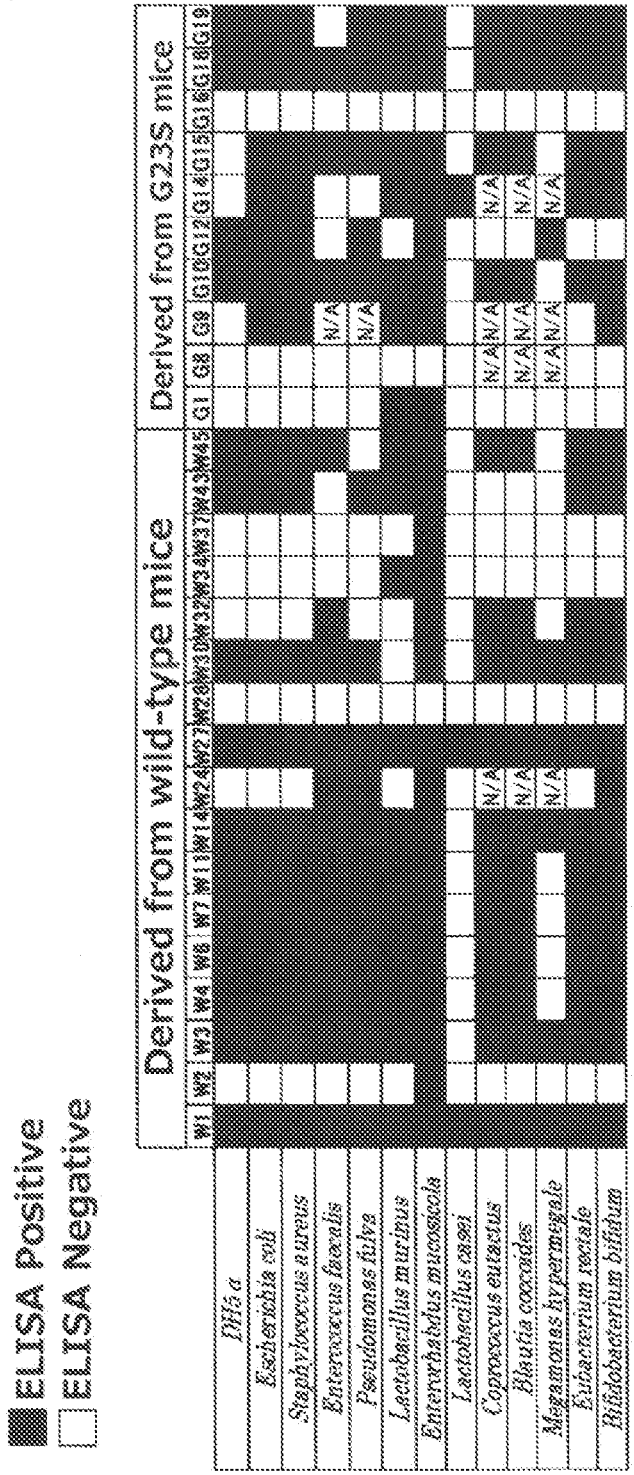
FIG. 1 shows experimental results to investigate the binding ability of monoclonal IgA for various intestinal bacteria.

FIG. 1 shows the results. The results revealed that, among the 27 kinds of monoclonal IgA, 22 kinds of monoclonal IgA (the W1, W3, W4, W6, W7, W11, W14, W24, W27, W30, W32, W34, W43, and W45 monoclonal IgA antibodies derived from wild-type mice; the G1, G9, G10, G12, G14, G15, G18, and G19 monoclonal IgA antibodies derived from G23S mice) bound to two or more species of the intestinal bacteria.

Subsequently, an experiment to compare the binding strength of such monoclonal IgA antibodies against intestinal bacteria was performed by changing the concentrations of the antibodies used. Specifically, the experiment was performed using a measurement method with the ELISA described above. The monoclonal IgA antibodies used were the W27, G15, and G19 monoclonal IgA antibodies. The W2 monoclonal IgA antibody was used as a negative control.

The indigenous intestinal bacteria used were Staphylococcus aureus, Escherichia coli, and Enterococcus faecalis.

Figure 2:
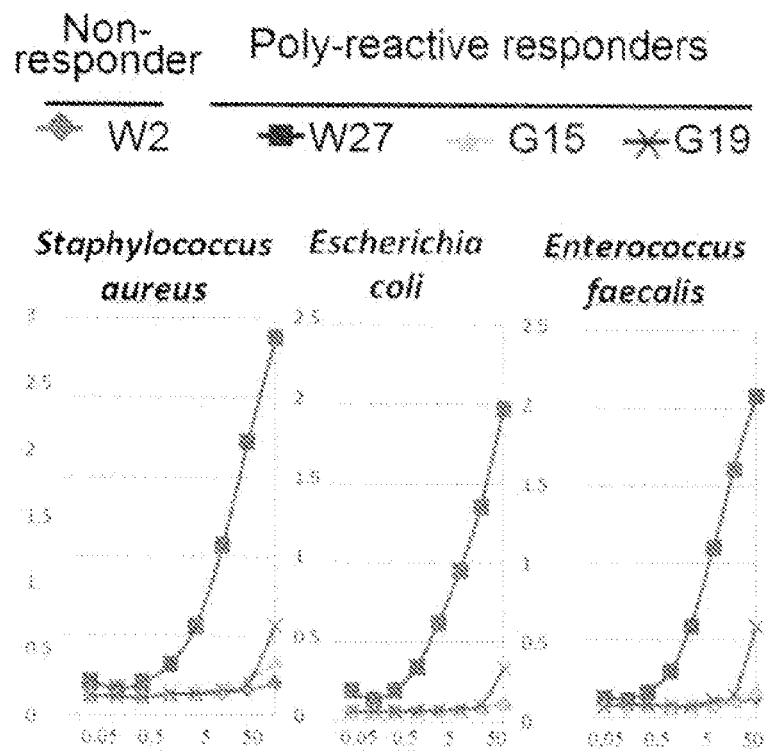
FIG. 2 shows experimental results to evaluate the concentration-dependent binding ability of monoclonal IgA for various intestinal bacteria. From left to right, the graphs illustrate results of binding to *Staphylococcus aureus, Escherichia coli,* and *Enterococcus faecalis.* In the graphs of FIG. 2, the ordinate indicates OD (405 nm) values, and the abscissa indicates the concentration of each IgA antibody used (0.017, 0.05, 0.17, 0.5, 1.7, 5.0, 17, and 50 µg/ml).

FIG. 2 shows the results. Among several monoclonal IgA antibodies, the W27 monoclonal IgA antibody most efficiently bound to each species of the intestinal bacteria in a concentration-dependent manner.

The same experiment as used for the W27 monoclonal IgA antibody was performed for W27SC3F monoclonal IgA antibody, in which a secretory component bound to the W27 monoclonal IgA antibody, the W11 monoclonal IgA antibody, the W34 monoclonal IgA antibody, the W43 monoclonal IgA antibody, and the G15 monoclonal IgA antibody. The W2 monoclonal IgA antibody was used as a negative control.

The W27SC3F monoclonal IgA antibody was produced as follows. First, RNA was extracted from a fragment of about 1 cm of the small intestine of a wild-type mouse. A reverse transcription reaction was performed using the RNA with SuperScript III produced by Invitrogen to obtain cDNA. The extracellular domain of the polyimmunoglobulin receptor was amplified by PCR using the cDNA as a template and using two primers (EcoRI SCF: 5'-gaattcaccatgaggctctacttg-3'; SEQ ID NO: 69 and Flag SC3R: 5'-ctcgagtcacttgtcgt-catcgtctttgtagtccccgggatt-3'; SEQ ID NO: 70). In the amplification, the base sequence of FLAG-tag was added to the reverse primer to make it possible to detect its protein expression in cells with anti-FLAG antibody. The base sequence of the amplified DNA encoded the amino acid sequence set forth in SEQ ID NO: 71. The sequence of FLAG-tag was added to the C-terminal (mSC3F-FLAG).

The obtained PCR product was subjected to restriction enzyme treatment and cloned into pcDNA3.1 (+) vector (Invitrogen). The completed expression vector is hereafter referred to as "pcDNA3.1 (+)/mSC3F." The plasmid DNA of pcDNA3.1 (+)/mSC3F was prepared from *Escherichia coli* and transfected into a hybridoma that produces the W27 monoclonal antibody with Nucleofector (AMAXA). Selection with G418 was then performed. The W27SC3F monoclonal IgA antibody was obtained from the thus-selected hybridoma, according to the method described above for collecting monoclonal IgA antibodies from hybridomas.

The indigenous intestinal bacteria used were *Enterococcus faecalis, Staphylococcus aureus, Escherichia coli*, and *Pseudomonas fulva*.

Figure 3:
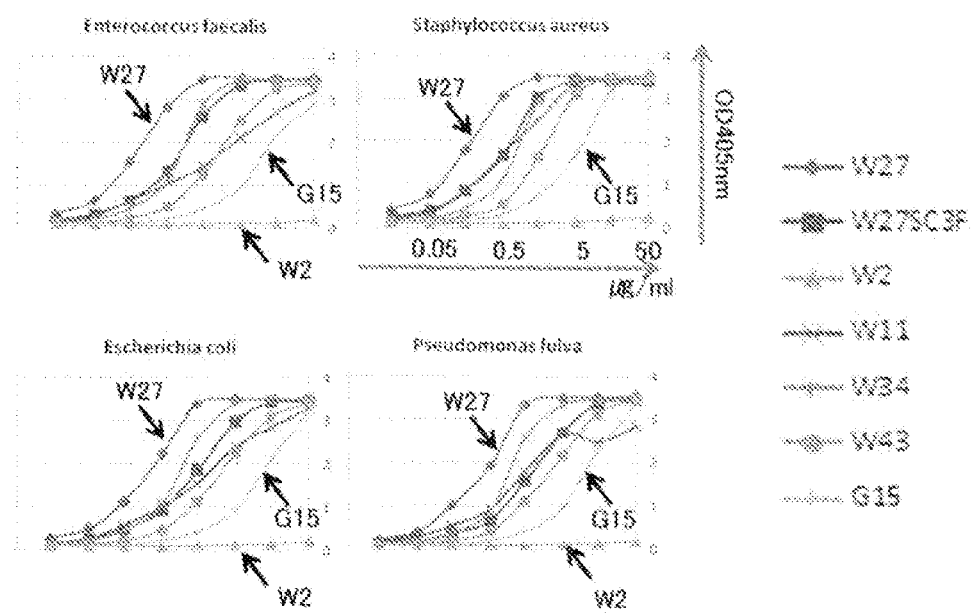
FIG. 3 shows experimental results to evaluate the concentration-dependent binding ability of monoclonal IgA for various intestinal bacteria. The graph in the upper left indicates results of binding to *Enterococcus faecalis,* the graph in the upper right indicates results of binding to *Staphylococcus aureus,* the graph in the lower left indicates results of binding to *Escherichia coli,* and the graph in the lower right indicates results of binding to *Pseudomonas fulva.* In the graphs of FIG. 3, the ordinate indicates OD (405 nm) values, and the abscissa indicates the concentration of each IgA antibody used (0.017, 0.05, 0.17, 0.5, 1.7, 5.0, 17, and 50 µg/ml).

FIG. 3 shows the results. This experiment also revealed that the W27 monoclonal IgA antibody most efficiently bound to each species of the intestinal bacteria in a concentration-dependent manner.

1-5: Western Blot Analysis for Bacteria Using Monoclonal IgA Antibodies

*Escherichia coli* (DH5α; commercially available product), *Escherichia coli* (a cloned strain from mouse intestinal content), *Pseudomonas fulva, Staphylococcus aureus*, and *Eubacterium rectale* were used as intestinal bacteria, and each was subjected to shaking culture in 10 ml of LB or an optimum culture medium under conditions appropriate for each species of the bacteria. After the bacterial cells were collected by centrifugation, they were suspended in PBS containing 1% NP-40, sonicated on ice, and allowed to stand on ice for 30 minutes. The supernatants were then obtained by centrifugation. SDS-buffer (containing 2-ME) was added to the supernatants, and protein denaturation was performed with heat treatment at 95° C. for 10 minutes. 8% SDS-PAGE was performed, followed by protein transfer to filters. After blocking, a Western blotting method in which reactions were performed using the W27, W30, and W45 monoclonal IgA antibodies (2 μg/m), followed by using goat anti-mouse IgA (1 μg/ml) (Southern Biotechnology) and IR800 anti-goat IgG (0.2 μg/ml) (Rockland), and if necessary labeled anti-Goat IgG, was performed to detect the signals with Odyssey (LI-COR).

Figure 4:
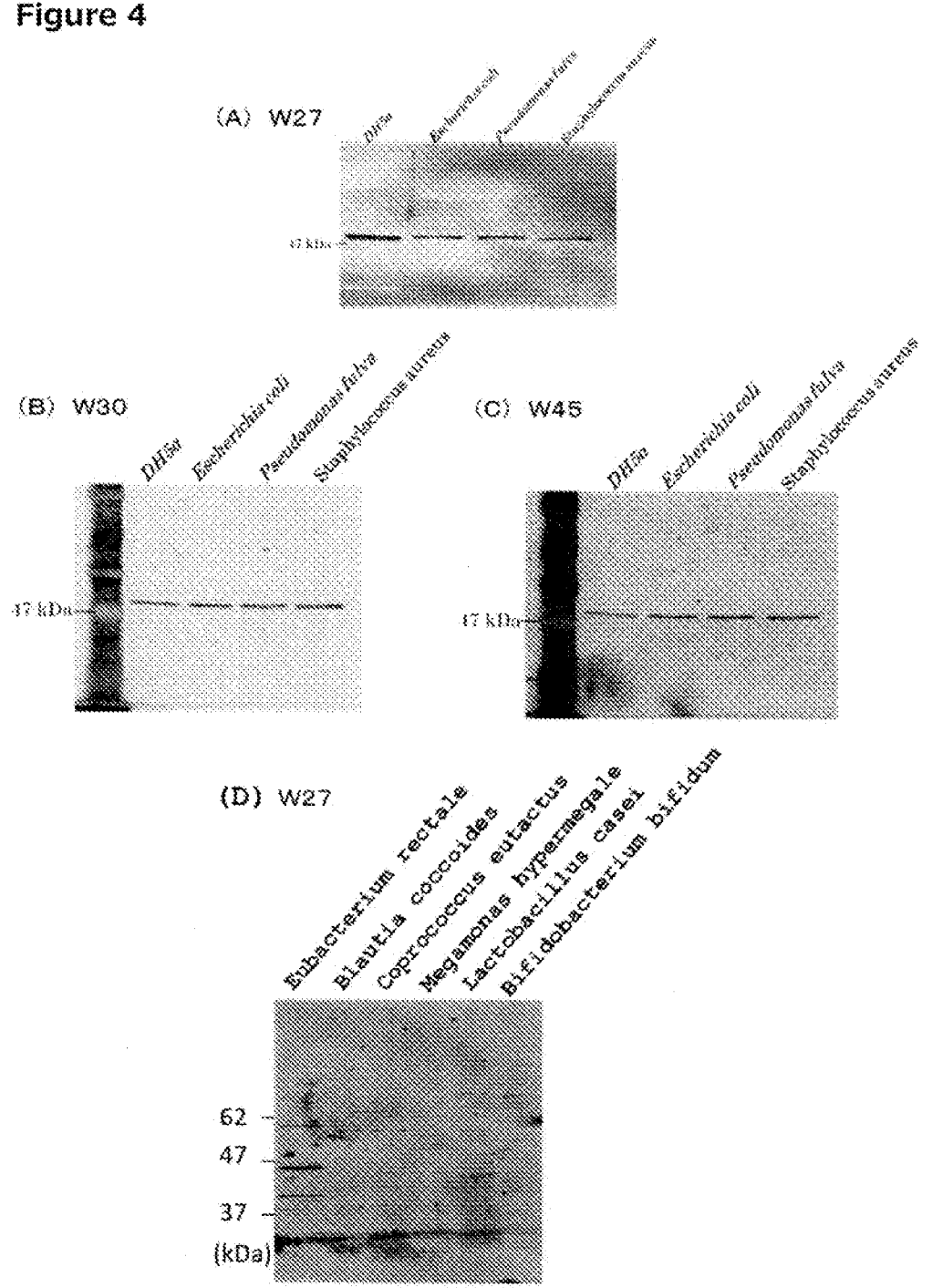
* FIG. 4 (D) indicates experimental results using W27 monoclonal IgA antibody. The lanes from the left to the right indicate the extracts of *Eubacterium rectale, Blautia coccoides, Coprococcus eutactus, Megamonas hypermegale, Lactobacillus casei,* and *Bifidobacterium bifidum.*

FIG. 4 shows the results. The results revealed that the W27, W30, and W45 monoclonal IgA antibodies bound to the extracts of all the bacteria described above. Thus, the experimental results suggested that the W27, W30, and W45 monoclonal IgA antibodies recognized one of the constituent proteins of intestinal bacteria as an antigen. Further, it was revealed that the molecular weight of this constituent protein was about 45 to 50 kDa.

Furthermore, an experiment was performed using *Eubacterium rectale, Blautia coccoides, Coprococcus eutactus, Megamonas hypermegale, Lactobacillus casei*, and *Bifidobacterium bifidum* in the same manner as described above. The monoclonal IgA antibody used was W27. FIG. 4 shows the results. The results revealed that the W27 monoclonal IgA antibody did not bind to the proteins in extracts of the bacteria, except for *Eubacterium rectale*.

1-6: Analysis of the Amino Acid Sequences of Monoclonal IgA Antibodies

A known method was used to analyze the amino acid sequences of, among the monoclonal IgA antibodies obtained by the method described above, five monoclonal IgA antibodies confirmed as binding to two or more species of intestinal bacteria, i.e., the W27, W30, W34, W43, and W11 monoclonal IgA antibodies.

The amino acid sequences were analyzed by using a known method. Specifically, 5' and 3' RACE reactions were performed to obtain the full-length base sequences. The RACE method was performed according to the procedure of an In-Fusion (registered trademark) SMARTer™ Directional cDNA library Construction Kit (Clontech). For the heavy chain, sequence analysis was performed using a combination of the primers included in the kit and the primers mentioned above. For the light chain, sequence analysis was performed using the following primers in combination.

```
CkR:
                                      (SEQ ID NO: 72)
5'-AACGTGAGGGTGCTGCTCATG-3' deg Vk:
                                      (SEQ ID NO: 73)
5'-GGCTGCAGSTTCAGTGGCAGTGGRTCWGGRAC-3'
```

Tables 4 to 8 show the results. The underlined portions in "Full-length Sequence" in these tables indicate variable region, and the portions in bold in "Full-length Sequence" and "Variable Region" indicate CDR1, CDR2, and CDR3 in order from the front to the back (from the N-terminus).

The nucleic acid sequences encoding these amino acids were as follows;

W27 monoclonal IgA antibody; heavy chain: SEQ ID NO: 51, light chain: SEQ ID NO: 52;

W30 monoclonal IgA antibody; heavy chain: SEQ ID NO: 53, light chain: SEQ ID NO: 54;

W34 monoclonal IgA antibody; heavy chain: SEQ ID NO: 55, light chain: SEQ ID NO: 56;

W43 monoclonal IgA antibody; heavy chain: SEQ ID NO: 57, light chain: SEQ ID NO: 58;

W11 monoclonal IgA antibody; heavy chain: SEQ ID NO: 59, light chain: SEQ ID NO: 60

TABLE 4

<Table 4: Amino acid Sequence of W27>

| | | |
|---|---|---|
| Heavy Chain | Full-length Sequence (SEQ ID NO: 1) | MAVVTGVNSEVQLQQSGSELVKSGASVKLSCTVSGFNFTDYYIHWVRQRTEQGLEWIGRIDPENDETTYAPKFQGKATMTADTSSNTAYLQLTSLTSEDTAVYYCARSTVLDYWGHGTTLTVSSESARNPTIYPLTLPRALSSDPVIIGCLIHDYFPSGTMNVTWGKSGKDITTVNFPPALASGGGYTMSSQLTLPAVECPEGESVKCSVQHDSNAVQELDVKCSGPPPPCPPCPPSCHPSLSLQRPALEDLLLGSDASLTCTLNGLRNPEGAVFTWEPSTGKDAVQKKAVQNSCGCYSVSSVLPGCAERWNSGASFKCTVTHPESDTLTGTIAKITVNTFPPQVHLLPPPSEELALNELVSLTCLVRAFNPKEVLVRWLHGNEELSPESYLVFEPLKEPGEGATTYLVTSVLRVSAELWKQGDQYSCMVGHEALPMNFTQKTIDRLSGKPTNVSVSVIMSEGDGICY |
| | Variable region (SEQ ID NO: 2) | MAVVTGVNSEVQLQQSGSELVYSGASVKLSCTVSGFNFTDYYIHWVRQRTEQGLEWIGRIDPENDETTYAPKFQGKATMTADTSSNTAYLQLTSLTSEDTAVYYCARSTVLDYWGHGTTLTVSS |
| | CDR1 (SEQ ID NO: 3) | DYYIH |
| | CDR2 (SEQ ID NO: 4) | RIDPENDETTYAPKFQG |
| | CDR3 (SEQ ID NO: 5) | STVL |
| Light Chain | Full-length Sequence (SEQ ID NO 6) | MFWIPGFSSDVLMTQTPLSLYVSLGDQASISCRASQSIVHTNGNTYLEWYLQKPGQSPKLLIYKVSNRFSGVPDRFSGSGSGTDFILKISRVEAEDLGVYYCFQGSHVPPTFGGGTKLEVKRADAAPTVSIFPPSSEQLTSGGASVVCFLNNFYPKDINVKWKIDGSERQNGVLNSWTDQDSKDSTYSMSSTLTLTKDEYERHNSYTCEATHKTSTSPIVKSFNRNEC |
| | Variable region (SEQ ID NO: 7) | MFWIPGFSSDVLMTQTPLSLPVSLGDQASISCRASQSIVHTNGNTYLEWYLQKPGQSPKLLIYKVSNRFSGVPDRFSGSGSGTDFILKISRVEAEDLGVYYCFQGSHVPPTFGGGTKLEVKRADAAPTVSIFPPSSEQLTSGG |
| | CDR1 (SEQ ID NO: 8) | RASQSIVHTNGNTYLE |
| | CDR2 (SEQ ID NO: 9) | KVSNRFS |
| | CDR3 (SEQ ID NO: 10) | FQGSHVPP |

TABLE 5

<Table 5: Amino acid Sequence of W30>

| | | |
|---|---|---|
| Heavy Chain | Full-length Sequence (SEQ ID NO: 11) | MSSPQTLNTLTLTMGWNWIFLFLLSGTAGVHSEVQLQQSGPVLVKPGASVKMSCKASGYTFTDYFLNWIKQSHGKSLELIGVINPYNDGVTYNRKFKGKATLTVDKSSSTAYMELTSLTSGDSAVYYCARSGDGFYLYYFDYKGQGTTLTVSSESARNPTIYPLTLPRALSSDPVIIGCLIHDYFPSGTMNVTWGKSGKDITTVNFPPALASGGGYTMSSQLTLPAVECPEGESVKCSVQHDSNAVQELDVKCSGPPPPCPPCPPSCHPSLSLQRPALEDLLLGSDASLTCTLNGLRNPEGAVFTWEPSTGKDAVQKKAVQNSCGCYSVSSVLPGCAERWNSGASFKCTVTHPESDTLTGTIAKITVNTFPPQVHLLPPPSEELALNELVSLTCLVRAFNPKEVLVRWLHGNEELSPESYLVFEPLKEPGEGATTYLVTSVLRVSAELWKQGDQYSCMVGHEALPMNFTQKTIDRLSGKPTNVSVSVIMSEGDGICY |
| | Variable region (SEQ ID NO: 12) | MSSPQTLNTLTLTMGWNWIFLFLLSGTAGVHSEVQLQQSGPVLVKPGASVKMSCKASGYTFTDYFLNWIKQSHGKSLELIGVINPYNDGVTYNRKFKGKATLTVDKSSSTAYMELTSLTSGDSAVYYCARSGDGFYLYYFDYWGQGTTLTVSS |
| | CDR1 (SEQ ID NO: 13) | DYFLN |
| | CDR2 (SEQ ID NO: 14) | VINPYNDGVTYNRKFKG |
| | CDR3 (SEQ ID NO: 15) | SGDGFYL |

TABLE 5-continued

<Table 5: Amino acid Sequence of W30>

| | | |
|---|---|---|
| Light Chain | Full-length Sequence (SEQ ID NO: 16) | MVFTPQILGLMLFWISASRGEIVLTQSPVTLSVTPGDN VSLSCRASQSISYNLHWFQQKSHESPRLLIKFASQSIS GIPSRFRGYGSGTDFTLSINSVETEDFGMYFCQQSNSW PQTFGGGTKLEIKRADAAPTVSIFPPSSEQLTSGGASV VCFLNNFYPKDINVKWKIDGSERQNGVLNSWTDQDSKD STYSMSSTLTLTKDEYERHNSYTCEATHKTSTSPIVKS FRNEC |
| | Variable region (SEQ ID NO: 17) | MVFTPQILGLMLFWISASRGEIVLTQSPVTLSVTPGDN VSLSCRASQSISYNLHWFQQKSHESPRLLIKFASQSIS GIPSRFRGYGSGTDFTLSINSVETEDFGMYFCQQSNSW PQTFGGGTKLEIKRADAAPTVSIFPPSSEQLTSGG |
| | CDR1 (SEQ ID NO: 18) | RASQSISYNLH |
| | CDR2 (SEQ ID NO: 19) | FASQSIS |
| | CDR3 (SEQ ID NO: 20) | QQSNSWPQ |

TABLE 6

<Table 6: Amino acid Sequence of W34>

| | | |
|---|---|---|
| Heavy Chain | Full-length Sequence (SEQ ID NO: 21) | MSVLILLWLFTAFPGILSDVQLQESGPGMVKPSQSLSL TCTVTGYSITSGYDWHWIRHFPGNKLEWMGYISYSGST DYNPALRSRISITRDTSTNHFFLKVNSVTTEDTATYYC ARDGYGSNYVMAYWGQGTSVTVSSESARNPTYYPLTLP RALSSDPVIIGCLIHDYFPSGTMNVTWGKSGKDITTVN FPPALASGGGYTMSSQLTLPAVECPEGESVKCSVQHDS NAVQELDVKCSGPPPPCPPCPPSCHPSLSLQRPALEDL LLGSDASLTCTLNGLRNPEGAVFTWEPSTGKDAVQKKA VQNSCGCYSVSSVLPGCAERWNSGASFKCTVTHPESDT LTGTIAKITVNTFPPQVHLLPPPSEELALNELVSLTCL VRAFNPKEVLVRWLHGNEELSPESYLVFEPLKEPGEGA TTYLVTSVLRVSAELWKQGDQYSCMVGHEALPMNFTQK TIDRLSGKPTNVSVSVIMSEGDGICY |
| | Variable region (SEQ ID NO: 22) | MSVLILLWLFTAFPGILSDVQLQESGPGMVKPSQSLSL TCTVTGYSITSGYDWHWIRHFPGNKLEWMGYISYSGST DYNPALRSRISITRDTSTNHFFLKVNSVTTEDTATYYC ARDGYGSNYVMAYWGQGTSVTVSS |
| | CDR1 (SEQ ID NO: 23) | SGYDWH |
| | CDR2 (SEQ ID NO: 24) | YISYSGSTDYNPALRS |
| | CDR3 SEQ ID NO: 25) | DGYGSN |
| Light Chain | Full-length Sequence (SEQ ID NO: 26) | MHFQVQIFSFLLISASVIMSRGQIVLTQSPAIMSASPG EKVTITCSASSSVHYIHWFQLKPGTSPKLWIYSTSNLA SGVPARFSGSGSGTSYSLTISRMEAEDAATYYCQQRSS YPLTFGAGTKLELKRADAAPTVSIFPPSSEQLTSGGAS VVCFLNNFYPKDINVKWKIDGSERQNGVLNSWTDQDSK DSTYSMSSTLTLTKDEYERHNSYTCEATHKTSTSPIVK SFNRNEC |
| | Variable region (SEQ ID NO: 27) | MHFQVQIFSFLLISASVIMSRGQIVLTQSPAIMSASPG EKVTITCSASSSVHYIHWFQLKPGTSPKLWIYSTSNLA SGVPARFSGSGSGTSYSLTISRMEAEDAATYYCQQRSS YPLTFGAGTKLELKRADAAPTVSIFPPSSEQLTSGG |
| | CDR1 (SEQ ID NO: 28) | SASSSVHYIH |
| | CDR2 (SEQ ID NO: 29) | STSNLAS |
| | CDR3 (SEQ ID NO: 30) | QQRSSYPL |

TABLE 7

<Table 7: Amino acid Sequence of W43>

| | | |
|---|---|---|
| Heavy Chain | Full-length Sequence (SEQ ID NO: 31) | MSSPQTLNTLTLTMGWSWIFLFLLSEAAGVLSEVQLQQ SGPELVKPGASVKMSCKASGYTFTDYNMHWVKQSHGKS LEWIGYINLYNDGTDYSQKFEGRSTLTLNKSSNTAYME LRSLTSEDSAVYYCARDYGNFAYFFDYWGQGTTLTVSS ESARNPTIYPLTLPRALSSDPVIIGCLIHDYFPSGTMN VTWGKSGKDITTVNFPPALASGGGYTMSSQLTLPAVEC PEGESVKCSVQHDSNAVQELDVKCSGPPPPCPPCPPSC HRSLSLQRPALEDLLLGSDASLTCTLNGLRNPEGAVFT WEPSTGKDAVQKKAVQNSCGCYSVSSVLPGCAERWNSG ASFKCTVTHPESDTLTGTIAKITVNTFPPQVHLLPPPS EELALNELVSLTCLVRAFNPKEVLVRWLHGNEELSPES YLVFEPLKEPGEGATTYLVTSVLRVSAELWKQGDQYSC MVGHEALPMNFTQKTIDRLSGKPTNVSVSVIMSEGDGI CY |
| | Variable region (SEQ ID NO: 32) | MSSPQTLNTLTLTMGWSWIFLFLLSEAAGVLSEVQLQQ SGPELVKPGASVKMSCKASGYTFTDYNMHWVKQSHGKS LEWIGYINLYNDGTDYSQKFEGRSTLTLNKSSNTAYME LRSLTSEDSAVYYCARDYGNFAYFFDYWGQGTTLTVSS |
| | CDR1 (SEQ ID NO: 33) | DYNNH |
| | CDR2 (SEQ ID NO: 34) | YINLYNDGTDYSQYFEG |
| | CDR3 (SEQ ID NO: 35) | DYGNFAYF |
| Light Chain | Full-length Sequence (SEQ ID NO: 36) | MTMLSLAPLLSLLLLCVSDSRAETTVTQSPASLSVATG EKVTIRCITSTDIDDDMNWFQQRPGEPPKLLISEGNVL RPGVPSRFSSSGYGTDFVFTIEDTLSEDVADYYCLQSD NMPLSFGAGTKLELKRADAAPTVSIFPFSSEQLTSGGA SVVCFLNNFYPKDINVKWKIDGSERQNGVLNSWTDQDS KDSTYSMSSTLTLTKDEYERHNSYTCEATHKTSTSPIV KSFNRNEC |
| | Variable region (SEQ ID NO: 37) | MTMLSLAPLLSLLLLCVSDSRAETTVTQSPASLSVATG EKVTIRCITSTDIDDDMNWFQQRPGEPPKLLISEGNVL RPGVPSRFSSSGYGTDFVFTIEDTLSEDVADYYCLQSD NMPLSFGAGTKLELKRADAAPTVSIFPPSSEQLTSGG |
| | CDR1 (SEQ ID NO: 38) | ITSTDIDDDMN |
| | CDR2 (SEQ ID NO: 39) | EGNVLRP |
| | CDR3 (SEQ ID NO: 40) | LQSDNMPLS |

TABLE 8

<Table 8: Amino acid Sequence of W11>

| | | |
|---|---|---|
| Heavy Chain | Full-length Sequence (SEQ ID NO: 41) | MAVLGLLFCLVTFPSCVLSQVQLKQSGPGLVQPSQSLS ITCTVSGFSLTNYGVHWIRQSPGKGLEWLGVIWSGGRI DYNAAFISRLNINKDNSKSQVFFKMNSLQTDDTAIYYC ARTYDGYYFFQYWGQGTPLTVSSESARNPTIYPLTLPR ALSSDPVIIGCLIHDYFPSGTMNVTWGKSGKDITTVNF PPALASGGGYTMSSQLTLPAVECPEGESVKCSVQHDSN AVQELDVKCSGPPRPCPPCPPSGHPSLSLQRPALEDLL LGSDASLTCTLNGLRNPEGAVFTWEPSTGKDAVQKKAV QNSCGCYSVSSVLPGCAERWNSGASFKCTVTHPESDTL TGTIAKITVNTFPPQVHLLPPPSEELALNELVSLTCLV RAFNPKEVLVRWLHGNEELSPESYLVFEPLKEPGEGAT TYLVTSVLRVSAELWKQGDQYSCMVGHEALPVNFTQKT IDRLSGKPTNVSVSVIMSEGDGICY |
| | Variable region (SEQ ID NO: 42) | MAVLGLLFCLVTFPSCVLSQVQLKQSGPGLVQPSQSLS ITCTVSGFSLTNYGVHWIRQSPOKGLEWLGVIWSGGRI DYNAAFISRLNINKDNSKSQVFFKMNSLQTDDTAIYYC ARTYDGYYFFQYWGQGTPLTVSS |
| | CDR1 (SEQ ID NO: 43) | NYGVH |
| | CDR2 (SEQ ID NO: 44) | VIWSGGRIDYNAAFIS |
| | CDR3 (SEQ ID NO: 45) | TYDGYYFFQ |

TABLE 8-continued

<Table 8: Amino acid Sequence of W11

| | | |
|---|---|---|
| Light Chain | Full-length Sequence (SEQ ID NO: 46) | MKLPVRLLVLMFWIPASSSDVVMTQTPLSLPVSLGDEA SISCRSSRSLTHSNGHTFLDWYLQKPGQSPKLLIYKVS NRFSGVPDRFSGSGSGTDFTLKISRVEAEDLGVYFCAQ STHAPLLTFGAGTKLELKRADAAPTVSIFPPSSEQLTS GGASVVCFLNNFYPKDINVKWKIDGSERQNGVLNSWTD QDSKDSTYSMSSTLTLTKDEYERHNSYTCEATHKTSTS PIVKSFNRNEC |
| | Variable region (SEQ ID NO: 47) | MKLPVRLLVLMFWIPASSSDVVMTQTPLSLPVSLGDEA SISCRSSRSLIHSNGHTFLDWYLQKPGQSPKLLIYKVS NRFSGVPDRFSGSGSGTDFTLKISRVEAEDLGVYFCAQ STHAPLLTFGAGTKLELERADAAPTVSIFPPSSEQLTS GG |
| | CDR1 (SEQ ID NO: 48) | RSSRSLIHSNGHTFLD |
| | CDR2 (SEQ ID NO: 49) | KVSNRFS |
| | CDR3 (SEQ ID NO: 50) | AQSTHAPL |

Example 2

Experiment to Identify Antigens for Monoclonal IgA Antibodies 2-1: Immunoprecipitation Experiment After cell extracts were prepared from three species of bacteria, i.e., *Escherichia coli* (DH5α), *Pseudomonas fulva*, and *Staphylococcus aureus*, by the method described in section 1-5 above, 2-ME (final concentration of 300 mM) and SDS (final concentration of 1%) were added, and heat denaturation was performed at 95° C. for 10 minutes. Thereafter, in each solution, the 2-ME concentration was adjusted to 60 mM, and the SDS concentration was adjusted to 0.2%. First, 100 µl of Protein G Sepharose 4 Fast Flow (GE) that had been washed was added to each cell extract, and the resulting mixtures were mixed by inversion at 4° C. for 30 minutes. Components that non-specifically bind to Protein G Sepharose were then eliminated by centrifugation. 5 µg of the W27 monoclonal IgA antibody was added to each of the cell extracts obtained after the pre-clear, and the resulting mixtures were allowed to stand on ice for 30 minutes. Thereafter, 5 µg of goat anti-mouse IgA was added, and the resulting mixtures were allowed to stand on ice for another 30 minutes. Subsequently, 30 µl of Protein G Sepharose 4 Fast Flow (GE) that had been washed was added, and the resulting mixtures were mixed by inversion at 4° C. for 15 hours. After a washing procedure with PBS containing 1% NP-40 was performed four times, a SDS-buffer (containing 2-ME) was added to the Protein G Sepharose, and protein denaturation was performed by heat treatment at 95° C. for 10 minutes (immunoprecipitation samples). These samples were subjected to 8% SDS-PAGE and then the Western blotting described above confirmed that the protein detected in section 1-5 above was concentrated (FIG. 5).

2-2: Two-dimensional Electrophoresis and MS Analysis

Each of the immunoprecipitation samples was subjected to acetone precipitation and dissolved in a buffer for two-dimensional electrophoresis. The gel used in the first dimension was agar gel (pH of 3 to 8; ATTO). In the second dimension, 6% SDS-PAGE was performed. Duplicated samples were prepared every time and simultaneously electrophoresed on two gels. One sample was then subjected to the Western blotting described above to confirm the location of the target protein in the gel. Specifically, after protein transfer to a filter, the transferred protein was stained with a MemCode™ Reversible Protein Stain Kit (Thermo Scientific) to obtain an image of the staining (FIG. 5).

Subsequently, after bleaching, the usual Western blotting described above was performed to obtain an image to confirm the location of the target protein (FIG. 5). The two images identified a spot of the target protein in two dimensions. The gel for the other sample was silver-stained (Sil-Best Stain; Nacalai Tesque) to visualize all the proteins. The target protein was identified based on the location information obtained from the first gel and excised from the second gel.

The excised gel was subjected to in-gel enzymatic digestion with trypsin at 37° C. for 15 hours.

MS analysis was performed with LCMS-IT-TOF (Shimadzu Corporation). The analysis results revealed that the protein in the spot was serine hydroxymethyltransferase as an antigen.

Subsequently, the full length of serine hydroxymethyltransferase represented by the amino acid sequence (SEQ ID NO: 74 that was c-Myc tagged at the C-terminus) was expressed in *Escherichia coli* (DH5α). Binding of each of the above antibodies (the W11, W27, W30, W34, and W43 monoclonal IgA antibodies) to serine hydroxymethyltransferase was examined by Western blotting. FIG. 9 shows the results.

The results revealed that not only the W27 monoclonal IgA antibody, but also the W11, W30, W34, and W43 monoclonal IgA antibodies, recognized serine hydroxymethyltransferase as an antigen.

2-3: Epitope Identification Experiment

Next, various mutants and wild type of serine hydroxymethyltransferase were expressed in *Escherichia coli* cells and 293T cells. An experiment was performed to investigate the epitope of the monoclonal antibodies described above.

The prepared mutants had the amino acid sequences at the following positions in the amino acid sequence represented by SEQ ID NO: 74:

(1) sequence represented by amino acids 1 to 417 (full length: wild-type),
(2) sequence represented by amino acids 11 to 417 (Δ2-10),
(3) sequence represented by amino acids 26 to 417 (Δ2-25),
(4) sequence represented by amino acids 29 to 417 (Δ2-28),
(5) sequence represented by amino acids 1 to 333 (Δ334-417), and
(6) sequence represented by amino acids 1 to 250 (Δ251-417).

Each sequence was added Myc-tag (40aa) at the C-terminus.

Cell lysates containing these wild type and mutants of serine hydroxymethyltransferase were subjected to Western blotting in the same manner as described above. The antibody used was the W27 monoclonal IgA antibody. FIG. 10 shows the results.

The results shown in FIG. 10 revealed that the W27 monoclonal IgA antibody bound to Δ2-25 mutant, but did not bind to Δ2-28 mutant. This fact was clear from the experiment using the 293T system, which was believed to be free of the influence of endogenous wild-type serine hydroxymethyltransferase derived from Escherichia coli. It was also revealed that the W27 monoclonal IgA antibody bound to Δ251-417 mutant and 6334-417 mutant.

Example 3

Oral Administration Experiment for W27 Monoclonal IgA Antibody 3-1: Analysis of Disease Model of G23S Mice Large intestinal tissue sections of AID G23S mice were prepared and stained with HE to investigate the degree of inflammation. As a result, significant reduction or atrophy in the crypts was observed even at 13-16 weeks of age compared with wild-type mice (FIG. 6). In particular, at 40 weeks or more of age, significant reduction or atrophy in the crypts and infiltration of inflammatory cells into mucosa of the large intestine were observed. Immunostaining showed that a larger number of $CD11b^+$ cells, IL-6 positive cells, IL-6, IL-17, and like inflammatory cells were present than in the wild-type mice.

Further, the results of measuring the expression levels of TNFα, IFNγ, IL-1β, IL-17, IL-6 and like inflammatory cytokines by a method using quantitative PCR similarly revealed that a larger number of inflammatory cells were present in the large intestinal tissues of AID G23S mice compared with those of the wild-type mice. The above facts revealed that AID G23S mice were suitable for use as a mouse model of inflammatory bowel disease, ulcerative colitis, and like diseases.

3-2: Effect of W27 Monoclonal IgA Antibody

The W27 monoclonal IgA antibody was orally administered to mice in a state of overreaction of the intestinal immune system. Hyperplasia of Peyer's patch germinal center and increase in the production of inflammatory cytokines was observed in intestinal tissue of the mice.

In the experiment, 10- to 12-week-old male AID G23S mice were used (Balb/c background). The W27 monoclonal IgA antibody was added to drinking water for feeding at a concentration of 25 μg/ml, and the resulting drinking water was orally given to AID G23S mice for 28 days. An experiment in which only water was given to AID G23S mice and an experiment in which only water was likewise given to wild-type mice were performed as negative controls.

Feed was also given to all the mice in the same manner as in usual feeding.

One month after the start of the administration of W27 monoclonal IgA antibody, the mice were euthanized, and the Peyer's patches were excised from the small intestine of tested mice. The Peyer's patch tissue was separated into single cells using glass slides, followed by staining of surface antigens of the cells with the antibodies described below. The percentage of the cell number of germinal center B cell fractions that exhibited $B220^+PNA^{high}$ was determined using flow cytometry analysis to investigate whether the germinal centers themselves regressed due to the administration of the W27 monoclonal IgA antibody.

The antibodies used in the flow cytometry are as follows:
PE-Cy7-labelled anti-mouse B220 (eBioscience);
Biotinylated peanut agglutinin (VECTOR laboratories);
Streptavidin APC (eBioscience).

Analysis of variance and t-test were performed to determine whether there was a significant difference in the percentage of Peyer's patch germinal center B cells between the administration group and the two negative control groups. Specifically, the percentage of Peyer's patch germinal center B cells of each group and the number of the Peyer's patch germinal center B cells of each group were analyzed. FIG. 7 shows the results.

The number of Peyer's patch germinal center B cells notably increased in the AID G23S mice not treated with W27 monoclonal IgA antibody. In contrast, it was revealed that the number of germinal center B cells in AID G23S mice treated with W27 monoclonal IgA antibody was notably reduced to a level similar to that of the wild-type mice by oral administration of the W27 monoclonal IgA antibody.

As described above, it is clear that AID G23S mice are suitable for use as a mouse model of inflammatory bowel disease, ulcerative colitis, and like diseases. In addition, Peyer's patch germinal center B cells grew excessively in the AID G23S mice. IgA antibodies in the intestinal immune system are produced in Peyer's patch germinal center B cells. Thus, an excessive increase in the B cells indicates that IgA antibodies are excessively produced in the intestinal immune system. This means that the state in AID G23S mice does not satisfactorily prevent entry of intestinal bacteria into intestinal mucosa. To improve such a state, T cells are complementarily activated in the intestinal immune system, which results in the increase in the production of inflammatory cytokines to cause inflammation, as described above.

Therefore, the W27 monoclonal IgA antibody, which has the effect of reducing the number of Peyer's patch germinal center B cells, makes it possible to normalize the intestinal immune system and suppress the function of, for example, T cells, thereby resolving inflammation. This clearly suggested that the W27 monoclonal IgA antibody is effective against diseases caused by alternation of intestinal bacterial growth and/or pathological changes of intestinal bacterial growth in gut microbiota, such as inflammatory bowel disease and ulcerative colitis, and, furthermore, intestinal diseases.

FIG. 11 shows the comparative results of analysis indicating reduction or pathological atrophy in the crypts between the large intestine of 13- to 15-week-old AID G23S mice to which the W27 monoclonal IgA antibody was orally administered for four weeks and the large intestine of 13- to 15-week-old wild-type mice or the large intestine of 13- to 15-week-old AID G23S mice not treated with W27 monoclonal IgA antibody. The contents of the entire large intestine were removed, and the large intestine was washed with saline, wound around a toothpick, embedded in OCT compound, and frozen. Thereafter, frozen sections with a thickness of 6 microns were prepared and subjected to hematoxylin eosin staining. Pathological portions in which reduction in the crypts was observed under a microscope were specified, and the extent of pathological portions in the entire large intestine was quantified and summarized graphically in FIG. 11a. Typical tissue images are shown in FIG. 11b.

3-3: Experiment for Kinetics of W27 Monoclonal IgA Antibody in the Body Through Oral Administration An experiment was performed to confirm whether the W27 monoclonal IgA antibody reaches the intestine via the digestive tract after being orally administered. AID knockout mice in which IgA is not produced were used in the experiment.

The W27 monoclonal IgA antibody was orally administered to the AID knockout mice in the same dose and method as in the oral administration experiment described above. Specifically, the W27 monoclonal IgA antibody was added to drinking water at a concentration of 25 μg/ml, and the resulting drinking water was administered by oral ingestion for 28 days in a sustained manner. On day 2, feces were collected. 100 mg of the collected feces was suspended in 0.9 ml of PBS, and the suspension was centrifuged to collect the supernatant. The IgA concentration in the supernatant was measured by ELISA.

FIG. 8 shows the results. The W27 monoclonal IgA antibody was detected from the feces. This fact revealed that after being orally administered, the W27 monoclonal IgA antibody reached the intestine with no influence of, for example, digestive enzymes in the gastrointestinal tract. This suggests that the W27 monoclonal antibody sufficiently exhibits a function as an orally administered composition.

3-4: Bacterial Cell Growth Suppression Effect Attained by Using Monoclonal IgA Antibodies

*Escherichia coli* strain DH5α was added to an LB liquid medium and subjected to shaking culture at 37° C. overnight. The following day, the resulting *Escherichia coli* liquid was suitably diluted, seeded onto an LB plate, and cultured at 37° C. overnight. The number of *Escherichia coli* in the *Escherichia coli* liquid was calculated by counting the number of colonies on the plate on the following day. The obtained number was defined as the number of *Escherichia coli* at the start of the growth suppression experiment.

At the same time as the *Escherichia coli* liquid was seeded onto the LB plate, 50 μl of *Escherichia coli* diluted in an LB liquid medium was added to a 96-well plate, and, further, the W27 monoclonal IgA antibody, the W27SC3F monoclonal IgA antibody, and the W2 monoclonal IgA antibody were individually added at a final concentration of 1.6 mg/ml.

The 96-well plate was subjected to static culture at 37° C. for 7 hours. After 7 hours, the resulting *Escherichia coli* liquids were individually diluted appropriately, seeded onto LB plates, and cultured at 37° C. overnight. On the following day, the number of colonies on each LB plate was counted to measure the number of *Escherichia coli*. The number of the bacterial cells calculated at the start of the experiment described above was defined as 1. Using this standard, the numbers of the bacterial cells after incubation with the IgA antibodies were calculated and plotted in a graph as the proliferation rate (the ordinate of the graph in FIG. 12). FIG. 12 shows the results.

From the results shown in FIG. 12, it can be found that there was a significant difference in the proliferation rate of *Escherichia coli* between the treatment of the W2 monoclonal IgA antibody and that of the W27 monoclonal IgA antibody. Although the detailed mechanism is unclear, the result of the above Example clarifies that the W2 monoclonal IgA antibody does not likely bind to *Escherichia coli*. The results thus suggested that the W27 monoclonal IgA antibody binds to *Escherichia coli*, thereby suppressing the growth of *Escherichia coli*.

Furthermore, the W27SC3F monoclonal IgA antibody, which is secretory IgA, exhibits the most potent growth suppression effect. This fact suggests that secretory IgA dimers actually secreted in the intestine in vivo recognize and bind to the bacteria and then exhibits unique effector functions, resulting in suppression of *Escherichia coli* growth. This suggested that when a monoclonal IgA antibody is used for controlling intestinal bacteria, it is preferably in the form of secretory IgA.

The invention claimed is:

1. A monoclonal antibody capable of binding to serine hydroxymethyltransferase, wherein the monoclonal antibody comprises a heavy chain variable region containing
    (1) a heavy chain CDR 1 consisting of the amino acid sequence represented by SEQ ID NO: 3,
    (2) a heavy chain CDR 2 consisting of the amino acid sequence represented by SEQ ID NO: 4, and
    (3) a heavy chain CDR 3 consisting of the amino acid sequence represented by SEQ ID NO: 5,
    and/or a light chain variable region containing
    (I) a light chain CDR 1 consisting of the amino acid sequence represented by SEQ ID NO: 8,
    (II) a light chain CDR 2 consisting of the amino acid sequence represented by SEQ ID NO: 9, and
    (III) a light chain CDR 3 consisting of the amino acid sequence represented by SEQ ID NO: 10.

2. The monoclonal antibody according to claim 1, wherein the monoclonal antibody comprises a heavy chain variable region consisting of the amino acid sequence represented by SEQ ID NO: 2, and/or a light chain variable region consisting of the amino acid sequence represented by SEQ ID NO: 7.

3. The monoclonal antibody according to claim 1, wherein the monoclonal antibody comprises a heavy chain consisting of the amino acid sequence represented by SEQ ID NO: 1, and/or a light chain consisting of the amino acid sequence represented by SEQ ID NO: 6.

4. The monoclonal antibody according to claim 3, wherein the monoclonal antibody inhibits the growth of at least two kinds of intestinal bacteria.

5. The monoclonal antibody according to claim 1, wherein the monoclonal antibody has a structure selected from the group consisting of F(ab')2, Fab, Fv, scFv, scFv-Fc, and mini body.

6. The monoclonal antibody according to claim 1, wherein the monoclonal antibody is an IgA antibody.

7. The monoclonal antibody according to claim 6, wherein the monoclonal IgA antibody is IgA1 or IgA2.

8. The monoclonal antibody according to claim 7, wherein the monoclonal IgA antibody is a J chain-containing polymer.

9. The monoclonal antibody according to claim 7, wherein the monoclonal IgA antibody comprises a secretory component.

10. The monoclonal antibody according to claim 1, wherein the monoclonal antibody is a humanized antibody.

11. The monoclonal antibody according to claim 1, wherein the monoclonal antibody is a chimeric antibody.

12. A pharmaceutical composition comprising the monoclonal antibody of claim 1.

13. A hybridoma producing the monoclonal antibody of claim 1.

* * * * *

SEQUENCE LISTING

```
<160> NUMBER OF SEQ ID NOS: 74

<210> SEQ ID NO 1
<211> LENGTH: 468
<212> TYPE: PRT
<213> ORGANISM: Artificial
<220> FEATURE:
<223> OTHER INFORMATION: W27 Heavy chain

<400> SEQUENCE: 1

Met Ala Val Val Thr Gly Val Asn Ser Glu Val Gln Leu Gln Gln Ser
1               5                   10                  15

Gly Ser Glu Leu Val Lys Ser Gly Ala Ser Val Lys Leu Ser Cys Thr
            20                  25                  30

Val Ser Gly Phe Asn Phe Thr Asp Tyr Tyr Ile His Trp Val Arg Gln
        35                  40                  45

Arg Thr Glu Gln Gly Leu Glu Trp Ile Gly Arg Ile Asp Pro Glu Asn
    50                  55                  60

Asp Glu Thr Thr Tyr Ala Pro Lys Phe Gln Gly Lys Ala Thr Met Thr
65                  70                  75                  80

Ala Asp Thr Ser Ser Asn Thr Ala Tyr Leu Gln Leu Thr Ser Leu Thr
                85                  90                  95

Ser Glu Asp Thr Ala Val Tyr Tyr Cys Ala Arg Ser Thr Val Leu Asp
            100                 105                 110
```

Tyr Trp Gly His Gly Thr Thr Leu Thr Val Ser Ser Glu Ser Ala Arg
            115                 120                 125

Asn Pro Thr Ile Tyr Pro Leu Thr Leu Pro Arg Ala Leu Ser Ser Asp
        130                 135                 140

Pro Val Ile Ile Gly Cys Leu Ile His Asp Tyr Phe Pro Ser Gly Thr
145                 150                 155                 160

Met Asn Val Thr Trp Gly Lys Ser Gly Lys Asp Ile Thr Thr Val Asn
                165                 170                 175

Phe Pro Pro Ala Leu Ala Ser Gly Gly Tyr Thr Met Ser Ser Gln
            180                 185                 190

Leu Thr Leu Pro Ala Val Glu Cys Pro Glu Gly Glu Ser Val Lys Cys
            195                 200                 205

Ser Val Gln His Asp Ser Asn Ala Val Gln Glu Leu Asp Val Lys Cys
        210                 215                 220

Ser Gly Pro Pro Pro Cys Pro Pro Cys Pro Ser Cys His Pro
225                 230                 235                 240

Ser Leu Ser Leu Gln Arg Pro Ala Leu Glu Asp Leu Leu Leu Gly Ser
            245                 250                 255

Asp Ala Ser Leu Thr Cys Thr Leu Asn Gly Leu Arg Asn Pro Glu Gly
            260                 265                 270

Ala Val Phe Thr Trp Glu Pro Ser Thr Gly Lys Asp Ala Val Gln Lys
            275                 280                 285

Lys Ala Val Gln Asn Ser Cys Gly Cys Tyr Ser Val Ser Ser Val Leu
        290                 295                 300

Pro Gly Cys Ala Glu Arg Trp Asn Ser Gly Ala Ser Phe Lys Cys Thr
305                 310                 315                 320

Val Thr His Pro Glu Ser Asp Thr Leu Thr Gly Thr Ile Ala Lys Ile
                325                 330                 335

Thr Val Asn Thr Phe Pro Pro Gln Val His Leu Pro Pro Pro Ser
            340                 345                 350

Glu Glu Leu Ala Leu Asn Glu Leu Val Ser Leu Thr Cys Leu Val Arg
            355                 360                 365

Ala Phe Asn Pro Lys Glu Val Leu Val Arg Trp Leu His Gly Asn Glu
        370                 375                 380

Glu Leu Ser Pro Glu Ser Tyr Leu Val Phe Glu Pro Leu Lys Glu Pro
385                 390                 395                 400

Gly Glu Gly Ala Thr Thr Tyr Leu Val Thr Ser Val Leu Arg Val Ser
            405                 410                 415

Ala Glu Leu Trp Lys Gln Gly Asp Gln Tyr Ser Cys Met Val Gly His
            420                 425                 430

Glu Ala Leu Pro Met Asn Phe Thr Gln Lys Thr Ile Asp Arg Leu Ser
        435                 440                 445

Gly Lys Pro Thr Asn Val Ser Val Ser Val Ile Met Ser Glu Gly Asp
    450                 455                 460

Gly Ile Cys Tyr
465

<210> SEQ ID NO 2
<211> LENGTH: 124
<212> TYPE: PRT
<213> ORGANISM: Artificial
<220> FEATURE:
<223> OTHER INFORMATION: W27 Heavy chain VR

<400> SEQUENCE: 2

```
Met Ala Val Val Thr Gly Val Asn Ser Glu Val Gln Leu Gln Gln Ser
1               5                   10                  15

Gly Ser Glu Leu Val Lys Ser Gly Ala Ser Val Lys Leu Ser Cys Thr
            20                  25                  30

Val Ser Gly Phe Asn Phe Thr Asp Tyr Tyr Ile His Trp Val Arg Gln
        35                  40                  45

Arg Thr Glu Gln Gly Leu Glu Trp Ile Gly Arg Ile Asp Pro Glu Asn
    50                  55                  60

Asp Glu Thr Thr Tyr Ala Pro Lys Phe Gln Gly Lys Ala Thr Met Thr
65                  70                  75                  80

Ala Asp Thr Ser Ser Asn Thr Ala Tyr Leu Gln Leu Thr Ser Leu Thr
                85                  90                  95

Ser Glu Asp Thr Ala Val Tyr Tyr Cys Ala Arg Ser Thr Val Leu Asp
            100                 105                 110

Tyr Trp Gly His Gly Thr Thr Leu Thr Val Ser Ser
        115                 120
```

<210> SEQ ID NO 3
<211> LENGTH: 5
<212> TYPE: PRT
<213> ORGANISM: Artificial
<220> FEATURE:
<223> OTHER INFORMATION: W27 Heavy chain CDR1

<400> SEQUENCE: 3

```
Asp Tyr Tyr Ile His
1               5
```

<210> SEQ ID NO 4
<211> LENGTH: 17
<212> TYPE: PRT
<213> ORGANISM: Artificial
<220> FEATURE:
<223> OTHER INFORMATION: W27 Heavy Chain CDR2

<400> SEQUENCE: 4

```
Arg Ile Asp Pro Glu Asn Asp Glu Thr Thr Tyr Ala Pro Lys Phe Gln
1               5                   10                  15

Gly
```

<210> SEQ ID NO 5
<211> LENGTH: 4
<212> TYPE: PRT
<213> ORGANISM: Artificial
<220> FEATURE:
<223> OTHER INFORMATION: W27 Heavy chain CDR3

<400> SEQUENCE: 5

```
Ser Thr Val Leu
1
```

<210> SEQ ID NO 6
<211> LENGTH: 228
<212> TYPE: PRT
<213> ORGANISM: Artificial
<220> FEATURE:
<223> OTHER INFORMATION: W27 Light chain

<400> SEQUENCE: 6

```
Met Phe Trp Ile Pro Gly Phe Ser Asp Val Leu Met Thr Gln Thr
1               5                   10                  15
```

```
Pro Leu Ser Leu Pro Val Ser Leu Gly Asp Gln Ala Ser Ile Ser Cys
            20                  25                  30

Arg Ala Ser Gln Ser Ile Val His Thr Asn Gly Asn Thr Tyr Leu Glu
        35                  40                  45

Trp Tyr Leu Gln Lys Pro Gly Gln Ser Pro Lys Leu Leu Ile Tyr Lys
    50                  55                  60

Val Ser Asn Arg Phe Ser Gly Val Pro Asp Arg Phe Ser Gly Ser Gly
65                  70                  75                  80

Ser Gly Thr Asp Phe Ile Leu Lys Ile Ser Arg Val Glu Ala Glu Asp
                85                  90                  95

Leu Gly Val Tyr Tyr Cys Phe Gln Gly Ser His Val Pro Pro Thr Phe
            100                 105                 110

Gly Gly Gly Thr Lys Leu Glu Val Lys Arg Ala Asp Ala Ala Pro Thr
        115                 120                 125

Val Ser Ile Phe Pro Pro Ser Ser Glu Gln Leu Thr Ser Gly Gly Ala
    130                 135                 140

Ser Val Val Cys Phe Leu Asn Asn Phe Tyr Pro Lys Asp Ile Asn Val
145                 150                 155                 160

Lys Trp Lys Ile Asp Gly Ser Glu Arg Gln Asn Gly Val Leu Asn Ser
                165                 170                 175

Trp Thr Asp Gln Asp Ser Lys Asp Ser Thr Tyr Ser Met Ser Ser Thr
            180                 185                 190

Leu Thr Leu Thr Lys Asp Glu Tyr Glu Arg His Asn Ser Tyr Thr Cys
        195                 200                 205

Glu Ala Thr His Lys Thr Ser Thr Ser Pro Ile Val Lys Ser Phe Asn
    210                 215                 220

Arg Asn Glu Cys
225

<210> SEQ ID NO 7
<211> LENGTH: 143
<212> TYPE: PRT
<213> ORGANISM: Artificial
<220> FEATURE:
<223> OTHER INFORMATION: W27 Light chain VR

<400> SEQUENCE: 7

Met Phe Trp Ile Pro Gly Phe Ser Ser Asp Val Leu Met Thr Gln Thr
1               5                   10                  15

Pro Leu Ser Leu Pro Val Ser Leu Gly Asp Gln Ala Ser Ile Ser Cys
            20                  25                  30

Arg Ala Ser Gln Ser Ile Val His Thr Asn Gly Asn Thr Tyr Leu Glu
        35                  40                  45

Trp Tyr Leu Gln Lys Pro Gly Gln Ser Pro Lys Leu Leu Ile Tyr Lys
    50                  55                  60

Val Ser Asn Arg Phe Ser Gly Val Pro Asp Arg Phe Ser Gly Ser Gly
65                  70                  75                  80

Ser Gly Thr Asp Phe Ile Leu Lys Ile Ser Arg Val Glu Ala Glu Asp
                85                  90                  95

Leu Gly Val Tyr Tyr Cys Phe Gln Gly Ser His Val Pro Pro Thr Phe
            100                 105                 110

Gly Gly Gly Thr Lys Leu Glu Val Lys Arg Ala Asp Ala Ala Pro Thr
        115                 120                 125

Val Ser Ile Phe Pro Pro Ser Ser Glu Gln Leu Thr Ser Gly Gly
    130                 135                 140
```

<210> SEQ ID NO 8
<211> LENGTH: 16
<212> TYPE: PRT
<213> ORGANISM: Artificial
<220> FEATURE:
<223> OTHER INFORMATION: W27 Light chain CDR1

<400> SEQUENCE: 8

```
Arg Ala Ser Gln Ser Ile Val His Thr Asn Gly Asn Thr Tyr Leu Glu
1               5                   10                  15
```

<210> SEQ ID NO 9
<211> LENGTH: 7
<212> TYPE: PRT
<213> ORGANISM: Artificial
<220> FEATURE:
<223> OTHER INFORMATION: W27 Light chain CDR2

<400> SEQUENCE: 9

```
Lys Val Ser Asn Arg Phe Ser
1               5
```

<210> SEQ ID NO 10
<211> LENGTH: 8
<212> TYPE: PRT
<213> ORGANISM: Artificial
<220> FEATURE:
<223> OTHER INFORMATION: W27 Light chain CDR3

<400> SEQUENCE: 10

```
Phe Gln Gly Ser His Val Pro Pro
1               5
```

<210> SEQ ID NO 11
<211> LENGTH: 497
<212> TYPE: PRT
<213> ORGANISM: Artificial
<220> FEATURE:
<223> OTHER INFORMATION: W30 Heavy chain

<400> SEQUENCE: 11

```
Met Ser Ser Pro Gln Thr Leu Asn Thr Leu Thr Leu Thr Met Gly Trp
1               5                   10                  15

Asn Trp Ile Phe Leu Phe Leu Leu Ser Gly Thr Ala Gly Val His Ser
                20                  25                  30

Glu Val Gln Leu Gln Gln Ser Gly Pro Val Leu Val Lys Pro Gly Ala
            35                  40                  45

Ser Val Lys Met Ser Cys Lys Ala Ser Gly Tyr Thr Phe Thr Asp Tyr
        50                  55                  60

Phe Leu Asn Trp Ile Lys Gln Ser His Gly Lys Ser Leu Glu Leu Ile
65                  70                  75                  80

Gly Val Ile Asn Pro Tyr Asn Asp Gly Val Thr Tyr Asn Arg Lys Phe
                85                  90                  95

Lys Gly Lys Ala Thr Leu Thr Val Asp Lys Ser Ser Ser Thr Ala Tyr
            100                 105                 110

Met Glu Leu Thr Ser Leu Thr Ser Gly Asp Ser Ala Val Tyr Tyr Cys
        115                 120                 125

Ala Arg Ser Gly Asp Gly Phe Tyr Leu Tyr Tyr Phe Asp Tyr Trp Gly
    130                 135                 140

Gln Gly Thr Thr Leu Thr Val Ser Ser Glu Ser Ala Arg Asn Pro Thr
145                 150                 155                 160
```

-continued

```
Ile Tyr Pro Leu Thr Leu Pro Arg Ala Leu Ser Ser Asp Pro Val Ile
            165                 170                 175

Ile Gly Cys Leu Ile His Asp Tyr Phe Pro Ser Gly Thr Met Asn Val
        180                 185                 190

Thr Trp Gly Lys Ser Gly Lys Asp Ile Thr Thr Val Asn Phe Pro Pro
    195                 200                 205

Ala Leu Ala Ser Gly Gly Tyr Thr Met Ser Ser Gln Leu Thr Leu
210                 215                 220

Pro Ala Val Glu Cys Pro Glu Gly Glu Ser Val Lys Cys Ser Val Gln
225                 230                 235                 240

His Asp Ser Asn Ala Val Gln Glu Leu Asp Val Lys Cys Ser Gly Pro
                245                 250                 255

Pro Pro Pro Cys Pro Pro Cys Pro Ser Cys His Pro Ser Leu Ser
            260                 265                 270

Leu Gln Arg Pro Ala Leu Glu Asp Leu Leu Leu Gly Ser Asp Ala Ser
        275                 280                 285

Leu Thr Cys Thr Leu Asn Gly Leu Arg Asn Pro Glu Gly Ala Val Phe
    290                 295                 300

Thr Trp Glu Pro Ser Thr Gly Lys Asp Ala Val Gln Lys Lys Ala Val
305                 310                 315                 320

Gln Asn Ser Cys Gly Cys Tyr Ser Val Ser Ser Val Leu Pro Gly Cys
                325                 330                 335

Ala Glu Arg Trp Asn Ser Gly Ala Ser Phe Lys Cys Thr Val Thr His
            340                 345                 350

Pro Glu Ser Asp Thr Leu Thr Gly Thr Ile Ala Lys Ile Thr Val Asn
        355                 360                 365

Thr Phe Pro Pro Gln Val His Leu Leu Pro Pro Ser Glu Glu Leu
    370                 375                 380

Ala Leu Asn Glu Leu Val Ser Leu Thr Cys Leu Val Arg Ala Phe Asn
385                 390                 395                 400

Pro Lys Glu Val Leu Val Arg Trp Leu His Gly Asn Glu Glu Leu Ser
                405                 410                 415

Pro Glu Ser Tyr Leu Val Phe Glu Pro Leu Lys Glu Pro Gly Glu Gly
            420                 425                 430

Ala Thr Thr Tyr Leu Val Thr Ser Val Leu Arg Val Ser Ala Glu Leu
        435                 440                 445

Trp Lys Gln Gly Asp Gln Tyr Ser Cys Met Val Gly His Glu Ala Leu
    450                 455                 460

Pro Met Asn Phe Thr Gln Lys Thr Ile Asp Arg Leu Ser Gly Lys Pro
465                 470                 475                 480

Thr Asn Val Ser Val Ser Val Ile Met Ser Glu Gly Asp Gly Ile Cys
                485                 490                 495

Tyr
```

<210> SEQ ID NO 12
<211> LENGTH: 153
<212> TYPE: PRT
<213> ORGANISM: Artificial
<220> FEATURE:
<223> OTHER INFORMATION: W30 Heavy chain VR

<400> SEQUENCE: 12

```
Met Ser Ser Pro Gln Thr Leu Asn Thr Leu Thr Leu Thr Met Gly Trp
1               5                   10                  15

Asn Trp Ile Phe Leu Phe Leu Leu Ser Gly Thr Ala Gly Val His Ser
```

```
                    20                  25                  30
Glu Val Gln Leu Gln Gln Ser Gly Pro Val Leu Val Lys Pro Gly Ala
         35                  40                  45

Ser Val Lys Met Ser Cys Lys Ala Ser Gly Tyr Thr Phe Thr Asp Tyr
     50                  55                  60

Phe Leu Asn Trp Ile Lys Gln Ser His Gly Lys Ser Leu Glu Leu Ile
 65                  70                  75                  80

Gly Val Ile Asn Pro Tyr Asn Asp Gly Val Thr Tyr Asn Arg Lys Phe
                 85                  90                  95

Lys Gly Lys Ala Thr Leu Thr Val Asp Lys Ser Ser Thr Ala Tyr
            100                 105                 110

Met Glu Leu Thr Ser Leu Thr Ser Gly Asp Ser Ala Val Tyr Tyr Cys
            115                 120                 125

Ala Arg Ser Gly Asp Gly Phe Tyr Leu Tyr Tyr Phe Asp Tyr Trp Gly
        130                 135                 140

Gln Gly Thr Thr Leu Thr Val Ser Ser
145                 150

<210> SEQ ID NO 13
<211> LENGTH: 5
<212> TYPE: PRT
<213> ORGANISM: Artificial
<220> FEATURE:
<223> OTHER INFORMATION: W30 Heavy chain CDR1

<400> SEQUENCE: 13

Asp Tyr Phe Leu Asn
1               5

<210> SEQ ID NO 14
<211> LENGTH: 17
<212> TYPE: PRT
<213> ORGANISM: Artificial
<220> FEATURE:
<223> OTHER INFORMATION: W30 Heavy chain CDR2

<400> SEQUENCE: 14

Val Ile Asn Pro Tyr Asn Asp Gly Val Thr Tyr Asn Arg Lys Phe Lys
1               5                   10                  15

Gly

<210> SEQ ID NO 15
<211> LENGTH: 7
<212> TYPE: PRT
<213> ORGANISM: Artificial
<220> FEATURE:
<223> OTHER INFORMATION: W30 Heavy chain CDR3

<400> SEQUENCE: 15

Ser Gly Asp Gly Phe Tyr Leu
1               5

<210> SEQ ID NO 16
<211> LENGTH: 234
<212> TYPE: PRT
<213> ORGANISM: Artificial
<220> FEATURE:
<223> OTHER INFORMATION: W30 Light chain

<400> SEQUENCE: 16

Met Val Phe Thr Pro Gln Ile Leu Gly Leu Met Leu Phe Trp Ile Ser
1               5                   10                  15
```

```
Ala Ser Arg Gly Glu Ile Val Leu Thr Gln Ser Pro Val Thr Leu Ser
            20                  25                  30

Val Thr Pro Gly Asp Asn Val Ser Leu Ser Cys Arg Ala Ser Gln Ser
            35                  40                  45

Ile Ser Tyr Asn Leu His Trp Phe Gln Gln Lys Ser His Glu Ser Pro
 50                  55                  60

Arg Leu Leu Ile Lys Phe Ala Ser Gln Ser Ile Ser Gly Ile Pro Ser
 65                  70                  75                  80

Arg Phe Arg Gly Tyr Gly Ser Gly Thr Asp Phe Thr Leu Ser Ile Asn
            85                  90                  95

Ser Val Glu Thr Glu Asp Phe Gly Met Tyr Phe Cys Gln Gln Ser Asn
            100                 105                 110

Ser Trp Pro Gln Thr Phe Gly Gly Gly Thr Lys Leu Glu Ile Lys Arg
            115                 120                 125

Ala Asp Ala Ala Pro Thr Val Ser Ile Phe Pro Pro Ser Ser Glu Gln
130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
            195                 200                 205

His Asn Ser Tyr Thr Cys Glu Ala Thr His Lys Thr Ser Thr Ser Pro
210                 215                 220

Ile Val Lys Ser Phe Asn Arg Asn Glu Cys
225                 230

<210> SEQ ID NO 17
<211> LENGTH: 149
<212> TYPE: PRT
<213> ORGANISM: Artificial
<220> FEATURE:
<223> OTHER INFORMATION: W30 Light chain VR

<400> SEQUENCE: 17

Met Val Phe Thr Pro Gln Ile Leu Gly Leu Met Leu Phe Trp Ile Ser
 1               5                   10                  15

Ala Ser Arg Gly Glu Ile Val Leu Thr Gln Ser Pro Val Thr Leu Ser
            20                  25                  30

Val Thr Pro Gly Asp Asn Val Ser Leu Ser Cys Arg Ala Ser Gln Ser
            35                  40                  45

Ile Ser Tyr Asn Leu His Trp Phe Gln Gln Lys Ser His Glu Ser Pro
 50                  55                  60

Arg Leu Leu Ile Lys Phe Ala Ser Gln Ser Ile Ser Gly Ile Pro Ser
 65                  70                  75                  80

Arg Phe Arg Gly Tyr Gly Ser Gly Thr Asp Phe Thr Leu Ser Ile Asn
            85                  90                  95

Ser Val Glu Thr Glu Asp Phe Gly Met Tyr Phe Cys Gln Gln Ser Asn
            100                 105                 110

Ser Trp Pro Gln Thr Phe Gly Gly Gly Thr Lys Leu Glu Ile Lys Arg
            115                 120                 125

Ala Asp Ala Ala Pro Thr Val Ser Ile Phe Pro Pro Ser Ser Glu Gln
130                 135                 140
```

```
Leu Thr Ser Gly Gly
145

<210> SEQ ID NO 18
<211> LENGTH: 11
<212> TYPE: PRT
<213> ORGANISM: Artificial
<220> FEATURE:
<223> OTHER INFORMATION: W30 Light chain CDR1

<400> SEQUENCE: 18

Arg Ala Ser Gln Ser Ile Ser Tyr Asn Leu His
1               5                   10

<210> SEQ ID NO 19
<211> LENGTH: 7
<212> TYPE: PRT
<213> ORGANISM: Artificial
<220> FEATURE:
<223> OTHER INFORMATION: W30 Light chain CDR2

<400> SEQUENCE: 19

Phe Ala Ser Gln Ser Ile Ser
1               5

<210> SEQ ID NO 20
<211> LENGTH: 8
<212> TYPE: PRT
<213> ORGANISM: Artificial
<220> FEATURE:
<223> OTHER INFORMATION: W30 Light chain CDR3

<400> SEQUENCE: 20

Gln Gln Ser Asn Ser Trp Pro Gln
1               5

<210> SEQ ID NO 21
<211> LENGTH: 482
<212> TYPE: PRT
<213> ORGANISM: Artificial
<220> FEATURE:
<223> OTHER INFORMATION: W34 Heavy chain

<400> SEQUENCE: 21

Met Ser Val Leu Ile Leu Leu Trp Leu Phe Thr Ala Phe Pro Gly Ile
1               5                   10                  15

Leu Ser Asp Val Gln Leu Gln Glu Ser Gly Pro Gly Met Val Lys Pro
                20                  25                  30

Ser Gln Ser Leu Ser Leu Thr Cys Thr Val Thr Gly Tyr Ser Ile Thr
            35                  40                  45

Ser Gly Tyr Asp Trp His Trp Ile Arg His Phe Pro Gly Asn Lys Leu
        50                  55                  60

Glu Trp Met Gly Tyr Ile Ser Tyr Ser Gly Ser Thr Asp Tyr Asn Pro
65                  70                  75                  80

Ala Leu Arg Ser Arg Ile Ser Ile Thr Arg Asp Thr Ser Thr Asn His
                85                  90                  95

Phe Phe Leu Lys Val Asn Ser Val Thr Thr Glu Asp Thr Ala Thr Tyr
                100                 105                 110

Tyr Cys Ala Arg Asp Gly Tyr Gly Ser Asn Tyr Val Met Ala Tyr Trp
            115                 120                 125

Gly Gln Gly Thr Ser Val Thr Val Ser Ser Glu Ser Ala Arg Asn Pro
        130                 135                 140
```

```
Thr Ile Tyr Pro Leu Thr Leu Pro Arg Ala Leu Ser Ser Asp Pro Val
145                 150                 155                 160

Ile Ile Gly Cys Leu Ile His Asp Tyr Phe Pro Ser Gly Thr Met Asn
            165                 170                 175

Val Thr Trp Gly Lys Ser Gly Lys Asp Ile Thr Thr Val Asn Phe Pro
            180                 185                 190

Pro Ala Leu Ala Ser Gly Gly Tyr Thr Met Ser Ser Gln Leu Thr
        195                 200                 205

Leu Pro Ala Val Glu Cys Pro Glu Gly Glu Ser Val Lys Cys Ser Val
        210                 215                 220

Gln His Asp Ser Asn Ala Val Gln Glu Leu Asp Val Lys Cys Ser Gly
225                 230                 235                 240

Pro Pro Pro Pro Cys Pro Pro Cys Pro Ser Cys His Pro Ser Leu
                245                 250                 255

Ser Leu Gln Arg Pro Ala Leu Glu Asp Leu Leu Gly Ser Asp Ala
        260                 265                 270

Ser Leu Thr Cys Thr Leu Asn Gly Leu Arg Asn Pro Glu Gly Ala Val
        275                 280                 285

Phe Thr Trp Glu Pro Ser Thr Gly Lys Asp Ala Val Gln Lys Ala
        290                 295                 300

Val Gln Asn Ser Cys Gly Cys Tyr Ser Val Ser Ser Val Leu Pro Gly
305                 310                 315                 320

Cys Ala Glu Arg Trp Asn Ser Gly Ala Ser Phe Lys Cys Thr Val Thr
                325                 330                 335

His Pro Glu Ser Asp Thr Leu Thr Gly Thr Ile Ala Lys Ile Thr Val
                340                 345                 350

Asn Thr Phe Pro Pro Gln Val His Leu Leu Pro Pro Pro Ser Glu Glu
            355                 360                 365

Leu Ala Leu Asn Glu Leu Val Ser Leu Thr Cys Leu Val Arg Ala Phe
        370                 375                 380

Asn Pro Lys Glu Val Leu Val Arg Trp Leu His Gly Asn Glu Glu Leu
385                 390                 395                 400

Ser Pro Glu Ser Tyr Leu Val Phe Glu Pro Leu Lys Glu Pro Gly Glu
                405                 410                 415

Gly Ala Thr Thr Tyr Leu Val Thr Ser Val Leu Arg Val Ser Ala Glu
                420                 425                 430

Leu Trp Lys Gln Gly Asp Gln Tyr Ser Cys Met Val Gly His Glu Ala
        435                 440                 445

Leu Pro Met Asn Phe Thr Gln Lys Thr Ile Asp Arg Leu Ser Gly Lys
        450                 455                 460

Pro Thr Asn Val Ser Val Ser Val Ile Met Ser Glu Gly Asp Gly Ile
465                 470                 475                 480

Cys Tyr

<210> SEQ ID NO 22
<211> LENGTH: 138
<212> TYPE: PRT
<213> ORGANISM: Artificial
<220> FEATURE:
<223> OTHER INFORMATION: W34 Heavy chain VR

<400> SEQUENCE: 22

Met Ser Val Leu Ile Leu Leu Trp Leu Phe Thr Ala Phe Pro Gly Ile
1               5                   10                  15
```

```
Leu Ser Asp Val Gln Leu Gln Glu Ser Gly Pro Gly Met Val Lys Pro
            20                  25                  30

Ser Gln Ser Leu Ser Leu Thr Cys Thr Val Gly Tyr Ser Ile Thr
        35                  40                  45

Ser Gly Tyr Asp Trp His Trp Ile Arg His Phe Pro Gly Asn Lys Leu
    50                  55                  60

Glu Trp Met Gly Tyr Ile Ser Tyr Ser Gly Ser Thr Asp Tyr Asn Pro
65                  70                  75                  80

Ala Leu Arg Ser Arg Ile Ser Ile Thr Arg Asp Thr Ser Thr Asn His
                85                  90                  95

Phe Phe Leu Lys Val Asn Ser Val Thr Thr Glu Asp Thr Ala Thr Tyr
            100                 105                 110

Tyr Cys Ala Arg Asp Gly Tyr Gly Ser Asn Tyr Val Met Ala Tyr Trp
        115                 120                 125

Gly Gln Gly Thr Ser Val Thr Val Ser Ser
        130                 135

<210> SEQ ID NO 23
<211> LENGTH: 6
<212> TYPE: PRT
<213> ORGANISM: Artificial
<220> FEATURE:
<223> OTHER INFORMATION: W34 Heavy chain CDR1

<400> SEQUENCE: 23

Ser Gly Tyr Asp Trp His
1               5

<210> SEQ ID NO 24
<211> LENGTH: 16
<212> TYPE: PRT
<213> ORGANISM: Artificial
<220> FEATURE:
<223> OTHER INFORMATION: W34 Heavy chain CDR2

<400> SEQUENCE: 24

Tyr Ile Ser Tyr Ser Gly Ser Thr Asp Tyr Asn Pro Ala Leu Arg Ser
1               5                   10                  15

<210> SEQ ID NO 25
<211> LENGTH: 6
<212> TYPE: PRT
<213> ORGANISM: Artificial
<220> FEATURE:
<223> OTHER INFORMATION: W34 Heavy chain CDR3

<400> SEQUENCE: 25

Asp Gly Tyr Gly Ser Asn
1               5

<210> SEQ ID NO 26
<211> LENGTH: 235
<212> TYPE: PRT
<213> ORGANISM: Artificial
<220> FEATURE:
<223> OTHER INFORMATION: W34 Light chain

<400> SEQUENCE: 26

Met His Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30
```

```
Met Ser Ala Ser Pro Gly Glu Lys Val Thr Ile Thr Cys Ser Ala Ser
            35                  40                  45

Ser Ser Val His Tyr Ile His Trp Phe Gln Leu Lys Pro Gly Thr Ser
 50                  55                  60

Pro Lys Leu Trp Ile Tyr Ser Thr Ser Asn Leu Ala Ser Gly Val Pro
 65                  70                  75                  80

Ala Arg Phe Ser Gly Ser Gly Ser Gly Thr Ser Tyr Ser Leu Thr Ile
                85                  90                  95

Ser Arg Met Glu Ala Glu Asp Ala Ala Thr Tyr Tyr Cys Gln Gln Arg
            100                 105                 110

Ser Ser Tyr Pro Leu Thr Phe Gly Ala Gly Thr Lys Leu Glu Leu Lys
            115                 120                 125

Arg Ala Asp Ala Ala Pro Thr Val Ser Ile Phe Pro Pro Ser Ser Glu
130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
            195                 200                 205

Arg His Asn Ser Tyr Thr Cys Glu Ala Thr His Lys Thr Ser Thr Ser
            210                 215                 220

Pro Ile Val Lys Ser Phe Asn Arg Asn Glu Cys
225                 230                 235

<210> SEQ ID NO 27
<211> LENGTH: 150
<212> TYPE: PRT
<213> ORGANISM: Artificial
<220> FEATURE:
<223> OTHER INFORMATION: W34 Light chain VR

<400> SEQUENCE: 27

Met His Phe Gln Val Gln Ile Phe Ser Phe Leu Leu Ile Ser Ala Ser
 1               5                   10                  15

Val Ile Met Ser Arg Gly Gln Ile Val Leu Thr Gln Ser Pro Ala Ile
                20                  25                  30

Met Ser Ala Ser Pro Gly Glu Lys Val Thr Ile Thr Cys Ser Ala Ser
            35                  40                  45

Ser Ser Val His Tyr Ile His Trp Phe Gln Leu Lys Pro Gly Thr Ser
 50                  55                  60

Pro Lys Leu Trp Ile Tyr Ser Thr Ser Asn Leu Ala Ser Gly Val Pro
 65                  70                  75                  80

Ala Arg Phe Ser Gly Ser Gly Ser Gly Thr Ser Tyr Ser Leu Thr Ile
                85                  90                  95

Ser Arg Met Glu Ala Glu Asp Ala Ala Thr Tyr Tyr Cys Gln Gln Arg
            100                 105                 110

Ser Ser Tyr Pro Leu Thr Phe Gly Ala Gly Thr Lys Leu Glu Leu Lys
            115                 120                 125

Arg Ala Asp Ala Ala Pro Thr Val Ser Ile Phe Pro Pro Ser Ser Glu
130                 135                 140

Gln Leu Thr Ser Gly Gly
145                 150
```

<210> SEQ ID NO 28
<211> LENGTH: 10
<212> TYPE: PRT
<213> ORGANISM: Artificial
<220> FEATURE:
<223> OTHER INFORMATION: W34 Light chain CDR1

<400> SEQUENCE: 28

```
Ser Ala Ser Ser Ser Val His Tyr Ile His
1               5                   10
```

<210> SEQ ID NO 29
<211> LENGTH: 7
<212> TYPE: PRT
<213> ORGANISM: Artificial
<220> FEATURE:
<223> OTHER INFORMATION: W34 Light chain CDR2

<400> SEQUENCE: 29

```
Ser Thr Ser Asn Leu Ala Ser
1               5
```

<210> SEQ ID NO 30
<211> LENGTH: 8
<212> TYPE: PRT
<213> ORGANISM: Artificial
<220> FEATURE:
<223> OTHER INFORMATION: W34 Light chain CDR3

<400> SEQUENCE: 30

```
Gln Gln Arg Ser Ser Tyr Pro Leu
1               5
```

<210> SEQ ID NO 31
<211> LENGTH: 496
<212> TYPE: PRT
<213> ORGANISM: Artificial
<220> FEATURE:
<223> OTHER INFORMATION: W43 Heavy chain

<400> SEQUENCE: 31

```
Met Ser Ser Pro Gln Thr Leu Asn Thr Leu Thr Leu Thr Met Gly Trp
1               5                   10                  15

Ser Trp Ile Phe Leu Phe Leu Leu Ser Glu Ala Ala Gly Val Leu Ser
            20                  25                  30

Glu Val Gln Leu Gln Gln Ser Gly Pro Glu Leu Val Lys Pro Gly Ala
        35                  40                  45

Ser Val Lys Met Ser Cys Lys Ala Ser Gly Tyr Thr Phe Thr Asp Tyr
    50                  55                  60

Asn Met His Trp Val Lys Gln Ser His Gly Lys Ser Leu Glu Trp Ile
65                  70                  75                  80

Gly Tyr Ile Asn Leu Tyr Asn Asp Gly Thr Asp Tyr Ser Gln Lys Phe
                85                  90                  95

Glu Gly Arg Ser Thr Leu Thr Leu Asn Lys Ser Ser Asn Thr Ala Tyr
            100                 105                 110

Met Glu Leu Arg Ser Leu Thr Ser Glu Asp Ser Ala Val Tyr Tyr Cys
        115                 120                 125

Ala Arg Asp Tyr Gly Asn Phe Ala Tyr Phe Phe Asp Tyr Trp Gly Gln
    130                 135                 140

Gly Thr Thr Leu Thr Val Ser Ser Glu Ser Ala Arg Asn Pro Thr Ile
145                 150                 155                 160
```

Tyr Pro Leu Thr Leu Pro Arg Ala Leu Ser Ser Asp Pro Val Ile Ile
                165                 170                 175

Gly Cys Leu Ile His Asp Tyr Phe Pro Ser Gly Thr Met Asn Val Thr
            180                 185                 190

Trp Gly Lys Ser Gly Lys Asp Ile Thr Thr Val Asn Phe Pro Pro Ala
        195                 200                 205

Leu Ala Ser Gly Gly Tyr Thr Met Ser Ser Gln Leu Thr Leu Pro
210                 215                 220

Ala Val Glu Cys Pro Glu Gly Glu Ser Val Lys Cys Ser Val Gln His
225                 230                 235                 240

Asp Ser Asn Ala Val Gln Glu Leu Asp Val Lys Cys Ser Gly Pro Pro
                245                 250                 255

Pro Pro Cys Pro Pro Cys Pro Ser Cys His Pro Ser Leu Ser Leu
            260                 265                 270

Gln Arg Pro Ala Leu Glu Asp Leu Leu Leu Gly Ser Asp Ala Ser Leu
        275                 280                 285

Thr Cys Thr Leu Asn Gly Leu Arg Asn Pro Glu Gly Ala Val Phe Thr
290                 295                 300

Trp Glu Pro Ser Thr Gly Lys Asp Ala Val Gln Lys Lys Ala Val Gln
305                 310                 315                 320

Asn Ser Cys Gly Cys Tyr Ser Val Ser Ser Val Leu Pro Gly Cys Ala
                325                 330                 335

Glu Arg Trp Asn Ser Gly Ala Ser Phe Lys Cys Thr Val Thr His Pro
            340                 345                 350

Glu Ser Asp Thr Leu Thr Gly Thr Ile Ala Lys Ile Thr Val Asn Thr
        355                 360                 365

Phe Pro Pro Gln Val His Leu Leu Pro Pro Pro Ser Glu Glu Leu Ala
370                 375                 380

Leu Asn Glu Leu Val Ser Leu Thr Cys Leu Val Arg Ala Phe Asn Pro
385                 390                 395                 400

Lys Glu Val Leu Val Arg Trp Leu His Gly Asn Glu Glu Leu Ser Pro
                405                 410                 415

Glu Ser Tyr Leu Val Phe Glu Pro Leu Lys Glu Pro Gly Glu Gly Ala
            420                 425                 430

Thr Thr Tyr Leu Val Thr Ser Val Leu Arg Val Ser Ala Glu Leu Trp
        435                 440                 445

Lys Gln Gly Asp Gln Tyr Ser Cys Met Val Gly His Glu Ala Leu Pro
450                 455                 460

Met Asn Phe Thr Gln Lys Thr Ile Asp Arg Leu Ser Gly Lys Pro Thr
465                 470                 475                 480

Asn Val Ser Val Ser Val Ile Met Ser Glu Gly Asp Gly Ile Cys Tyr
                485                 490                 495

<210> SEQ ID NO 32
<211> LENGTH: 152
<212> TYPE: PRT
<213> ORGANISM: Artificial
<220> FEATURE:
<223> OTHER INFORMATION: W43 Heavy chain VR

<400> SEQUENCE: 32

Met Ser Ser Pro Gln Thr Leu Asn Thr Leu Thr Leu Thr Met Gly Trp
1               5                   10                  15

Ser Trp Ile Phe Leu Phe Leu Leu Ser Glu Ala Ala Gly Val Leu Ser
                20                  25                  30

```
Glu Val Gln Leu Gln Gln Ser Gly Pro Glu Leu Val Lys Pro Gly Ala
             35                  40                  45

Ser Val Lys Met Ser Cys Lys Ala Ser Gly Tyr Thr Phe Thr Asp Tyr
 50                  55                  60

Asn Met His Trp Val Lys Gln Ser His Gly Lys Ser Leu Glu Trp Ile
 65                  70                  75                  80

Gly Tyr Ile Asn Leu Tyr Asn Asp Gly Thr Asp Tyr Ser Gln Lys Phe
                 85                  90                  95

Glu Gly Arg Ser Thr Leu Thr Leu Asn Lys Ser Ser Asn Thr Ala Tyr
            100                 105                 110

Met Glu Leu Arg Ser Leu Thr Ser Glu Asp Ser Ala Val Tyr Tyr Cys
            115                 120                 125

Ala Arg Asp Tyr Gly Asn Phe Ala Tyr Phe Phe Asp Tyr Trp Gly Gln
        130                 135                 140

Gly Thr Thr Leu Thr Val Ser Ser
145                 150
```

<210> SEQ ID NO 33
<211> LENGTH: 5
<212> TYPE: PRT
<213> ORGANISM: Artificial
<220> FEATURE:
<223> OTHER INFORMATION: W43 Heavy chain CDR1

<400> SEQUENCE: 33

```
Asp Tyr Asn Met His
1               5
```

<210> SEQ ID NO 34
<211> LENGTH: 17
<212> TYPE: PRT
<213> ORGANISM: Artificial
<220> FEATURE:
<223> OTHER INFORMATION: W43 Heavy chain CDR2

<400> SEQUENCE: 34

```
Tyr Ile Asn Leu Tyr Asn Asp Gly Thr Asp Tyr Ser Gln Lys Phe Glu
1               5                   10                  15

Gly
```

<210> SEQ ID NO 35
<211> LENGTH: 8
<212> TYPE: PRT
<213> ORGANISM: Artificial
<220> FEATURE:
<223> OTHER INFORMATION: W43 Heavy chain CDR3

<400> SEQUENCE: 35

```
Asp Tyr Gly Asn Phe Ala Tyr Phe
1               5
```

<210> SEQ ID NO 36
<211> LENGTH: 236
<212> TYPE: PRT
<213> ORGANISM: Artificial
<220> FEATURE:
<223> OTHER INFORMATION: W43 Light chain

<400> SEQUENCE: 36

```
Met Thr Met Leu Ser Leu Ala Pro Leu Leu Ser Leu Leu Leu Leu Cys
1               5                   10                  15

Val Ser Asp Ser Arg Ala Glu Thr Thr Val Thr Gln Ser Pro Ala Ser
```

```
                    20                  25                  30

Leu Ser Val Ala Thr Gly Glu Lys Val Thr Ile Arg Cys Ile Thr Ser
             35                  40                  45

Thr Asp Ile Asp Asp Asp Met Asn Trp Phe Gln Gln Arg Pro Gly Glu
         50                  55                  60

Pro Pro Lys Leu Leu Ile Ser Glu Gly Asn Val Leu Arg Pro Gly Val
 65                  70                  75                  80

Pro Ser Arg Phe Ser Ser Ser Gly Tyr Gly Thr Asp Phe Val Phe Thr
                 85                  90                  95

Ile Glu Asp Thr Leu Ser Glu Asp Val Ala Asp Tyr Tyr Cys Leu Gln
            100                 105                 110

Ser Asp Asn Met Pro Leu Ser Phe Gly Ala Gly Thr Lys Leu Glu Leu
            115                 120                 125

Lys Arg Ala Asp Ala Ala Pro Thr Val Ser Ile Phe Pro Pro Ser Ser
        130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
            195                 200                 205

Glu Arg His Asn Ser Tyr Thr Cys Glu Ala Thr His Lys Thr Ser Thr
        210                 215                 220

Ser Pro Ile Val Lys Ser Phe Asn Arg Asn Glu Cys
225                 230                 235

<210> SEQ ID NO 37
<211> LENGTH: 151
<212> TYPE: PRT
<213> ORGANISM: Artificial
<220> FEATURE:
<223> OTHER INFORMATION: W43 Light chain VR

<400> SEQUENCE: 37

Met Thr Met Leu Ser Leu Ala Pro Leu Leu Ser Leu Leu Leu Leu Cys
  1               5                  10                  15

Val Ser Asp Ser Arg Ala Glu Thr Thr Val Thr Gln Ser Pro Ala Ser
             20                  25                  30

Leu Ser Val Ala Thr Gly Glu Lys Val Thr Ile Arg Cys Ile Thr Ser
             35                  40                  45

Thr Asp Ile Asp Asp Asp Met Asn Trp Phe Gln Gln Arg Pro Gly Glu
         50                  55                  60

Pro Pro Lys Leu Leu Ile Ser Glu Gly Asn Val Leu Arg Pro Gly Val
 65                  70                  75                  80

Pro Ser Arg Phe Ser Ser Ser Gly Tyr Gly Thr Asp Phe Val Phe Thr
                 85                  90                  95

Ile Glu Asp Thr Leu Ser Glu Asp Val Ala Asp Tyr Tyr Cys Leu Gln
            100                 105                 110

Ser Asp Asn Met Pro Leu Ser Phe Gly Ala Gly Thr Lys Leu Glu Leu
            115                 120                 125

Lys Arg Ala Asp Ala Ala Pro Thr Val Ser Ile Phe Pro Pro Ser Ser
        130                 135                 140

Glu Gln Leu Thr Ser Gly Gly
```

-continued

```
145                 150

<210> SEQ ID NO 38
<211> LENGTH: 11
<212> TYPE: PRT
<213> ORGANISM: Artificial
<220> FEATURE:
<223> OTHER INFORMATION: W43 Light chain CDR1

<400> SEQUENCE: 38

Ile Thr Ser Thr Asp Ile Asp Asp Asp Met Asn
1               5                   10

<210> SEQ ID NO 39
<211> LENGTH: 7
<212> TYPE: PRT
<213> ORGANISM: Artificial
<220> FEATURE:
<223> OTHER INFORMATION: W43 Light chain CDR2

<400> SEQUENCE: 39

Glu Gly Asn Val Leu Arg Pro
1               5

<210> SEQ ID NO 40
<211> LENGTH: 9
<212> TYPE: PRT
<213> ORGANISM: Artificial
<220> FEATURE:
<223> OTHER INFORMATION: W43 light chain CDR3

<400> SEQUENCE: 40

Leu Gln Ser Asp Asn Met Pro Leu Ser
1               5

<210> SEQ ID NO 41
<211> LENGTH: 481
<212> TYPE: PRT
<213> ORGANISM: Artificial
<220> FEATURE:
<223> OTHER INFORMATION: W11 Heavy chain

<400> SEQUENCE: 41

Met Ala Val Leu Gly Leu Leu Phe Cys Leu Val Thr Phe Pro Ser Cys
1               5                   10                  15

Val Leu Ser Gln Val Gln Leu Lys Gln Ser Gly Pro Gly Leu Val Gln
                20                  25                  30

Pro Ser Gln Ser Leu Ser Ile Thr Cys Thr Val Ser Gly Phe Ser Leu
            35                  40                  45

Thr Asn Tyr Gly Val His Trp Ile Arg Gln Ser Pro Gly Lys Gly Leu
        50                  55                  60

Glu Trp Leu Gly Val Ile Trp Ser Gly Gly Arg Ile Asp Tyr Asn Ala
65                  70                  75                  80

Ala Phe Ile Ser Arg Leu Asn Ile Asn Lys Asp Asn Ser Lys Ser Gln
                85                  90                  95

Val Phe Phe Lys Met Asn Ser Leu Gln Thr Asp Asp Thr Ala Ile Tyr
                100                 105                 110

Tyr Cys Ala Arg Thr Tyr Asp Gly Tyr Tyr Phe Phe Gln Tyr Trp Gly
            115                 120                 125

Gln Gly Thr Pro Leu Thr Val Ser Ser Glu Ser Ala Arg Asn Pro Thr
        130                 135                 140

Ile Tyr Pro Leu Thr Leu Pro Arg Ala Leu Ser Ser Asp Pro Val Ile
```

```
                145                 150                 155                 160
        Ile Gly Cys Leu Ile His Asp Tyr Phe Pro Ser Gly Thr Met Asn Val
                        165                 170                 175

Thr Trp Gly Lys Ser Gly Lys Asp Ile Thr Thr Val Asn Phe Pro Pro
                        180                 185                 190

Ala Leu Ala Ser Gly Gly Tyr Thr Met Ser Ser Gln Leu Thr Leu
                        195                 200                 205

Pro Ala Val Glu Cys Pro Glu Gly Glu Ser Val Lys Cys Ser Val Gln
                        210                 215                 220

His Asp Ser Asn Ala Val Gln Glu Leu Asp Val Lys Cys Ser Gly Pro
        225                 230                 235                 240

Pro Pro Pro Cys Pro Pro Cys Pro Pro Ser Cys His Pro Ser Leu Ser
                        245                 250                 255

Leu Gln Arg Pro Ala Leu Glu Asp Leu Leu Leu Gly Ser Asp Ala Ser
                        260                 265                 270

Leu Thr Cys Thr Leu Asn Gly Leu Arg Asn Pro Glu Gly Ala Val Phe
                        275                 280                 285

Thr Trp Glu Pro Ser Thr Gly Lys Asp Ala Val Gln Lys Lys Ala Val
                        290                 295                 300

Gln Asn Ser Cys Gly Cys Tyr Ser Val Ser Val Leu Pro Gly Cys
        305                 310                 315                 320

Ala Glu Arg Trp Asn Ser Gly Ala Ser Phe Lys Cys Thr Val Thr His
                        325                 330                 335

Pro Glu Ser Asp Thr Leu Thr Gly Thr Ile Ala Lys Ile Thr Val Asn
                        340                 345                 350

Thr Phe Pro Pro Gln Val His Leu Leu Pro Pro Ser Glu Glu Leu
                        355                 360                 365

Ala Leu Asn Glu Leu Val Ser Leu Thr Cys Leu Val Arg Ala Phe Asn
                        370                 375                 380

Pro Lys Glu Val Leu Val Arg Trp Leu His Gly Asn Glu Glu Leu Ser
        385                 390                 395                 400

Pro Glu Ser Tyr Leu Val Phe Glu Pro Leu Lys Glu Pro Gly Glu Gly
                        405                 410                 415

Ala Thr Thr Tyr Leu Val Thr Ser Val Leu Arg Val Ser Ala Glu Leu
                        420                 425                 430

Trp Lys Gln Gly Asp Gln Tyr Ser Cys Met Val Gly His Glu Ala Leu
                        435                 440                 445

Pro Met Asn Phe Thr Gln Lys Thr Ile Asp Arg Leu Ser Gly Lys Pro
                        450                 455                 460

Thr Asn Val Ser Val Ser Val Ile Met Ser Glu Gly Asp Gly Ile Cys
        465                 470                 475                 480

Tyr

<210> SEQ ID NO 42
<211> LENGTH: 137
<212> TYPE: PRT
<213> ORGANISM: Artificial
<220> FEATURE:
<223> OTHER INFORMATION: W11 Heavy chain VR

<400> SEQUENCE: 42

Met Ala Val Leu Gly Leu Leu Phe Cys Leu Val Thr Phe Pro Ser Cys
1               5                   10                  15

Val Leu Ser Gln Val Gln Leu Lys Gln Ser Gly Pro Gly Leu Val Gln
                20                  25                  30
```

```
Pro Ser Gln Ser Leu Ser Ile Thr Cys Thr Val Ser Gly Phe Ser Leu
        35                  40                  45

Thr Asn Tyr Gly Val His Trp Ile Arg Gln Ser Pro Gly Lys Gly Leu
    50                  55                  60

Glu Trp Leu Gly Val Ile Trp Ser Gly Gly Arg Ile Asp Tyr Asn Ala
65                  70                  75                  80

Ala Phe Ile Ser Arg Leu Asn Ile Asn Lys Asp Asn Ser Lys Ser Gln
                85                  90                  95

Val Phe Phe Lys Met Asn Ser Leu Gln Thr Asp Asp Thr Ala Ile Tyr
            100                 105                 110

Tyr Cys Ala Arg Thr Tyr Asp Gly Tyr Tyr Phe Phe Gln Tyr Trp Gly
        115                 120                 125

Gln Gly Thr Pro Leu Thr Val Ser Ser
    130                 135
```

<210> SEQ ID NO 43
<211> LENGTH: 5
<212> TYPE: PRT
<213> ORGANISM: Artificial
<220> FEATURE:
<223> OTHER INFORMATION: W11 Heavy chain CDR1

<400> SEQUENCE: 43

```
Asn Tyr Gly Val His
1               5
```

<210> SEQ ID NO 44
<211> LENGTH: 16
<212> TYPE: PRT
<213> ORGANISM: Artificial
<220> FEATURE:
<223> OTHER INFORMATION: W11 Heavy chain CDR2

<400> SEQUENCE: 44

```
Val Ile Trp Ser Gly Gly Arg Ile Asp Tyr Asn Ala Ala Phe Ile Ser
1               5                   10                  15
```

<210> SEQ ID NO 45
<211> LENGTH: 9
<212> TYPE: PRT
<213> ORGANISM: Artificial
<220> FEATURE:
<223> OTHER INFORMATION: W11 Heavy chain CDR3

<400> SEQUENCE: 45

```
Thr Tyr Asp Gly Tyr Tyr Phe Phe Gln
1               5
```

<210> SEQ ID NO 46
<211> LENGTH: 239
<212> TYPE: PRT
<213> ORGANISM: Artificial
<220> FEATURE:
<223> OTHER INFORMATION: W11 light chain

<400> SEQUENCE: 46

```
Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Glu Ala Ser Ile Ser Cys Arg Ser Arg Ser Leu
        35                  40                  45
```

Ile His Ser Asn Gly His Thr Phe Leu Asp Trp Tyr Leu Gln Lys Pro
         50                  55                  60

Gly Gln Ser Pro Lys Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Leu Gly Val Tyr Phe Cys
                100                 105                 110

Ala Gln Ser Thr His Ala Pro Leu Leu Thr Phe Gly Ala Gly Thr Lys
                115                 120                 125

Leu Glu Leu Lys Arg Ala Asp Ala Ala Pro Thr Val Ser Ile Phe Pro
130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
                180                 185                 190

Ser Lys Asp Ser Thr Tyr Ser Met Ser Ser Thr Leu Thr Leu Thr Lys
                195                 200                 205

Asp Glu Tyr Glu Arg His Asn Ser Tyr Thr Cys Glu Ala Thr His Lys
210                 215                 220

Thr Ser Thr Ser Pro Ile Val Lys Ser Phe Asn Arg Asn Glu Cys
225                 230                 235

<210> SEQ ID NO 47
<211> LENGTH: 154
<212> TYPE: PRT
<213> ORGANISM: Artificial
<220> FEATURE:
<223> OTHER INFORMATION: W11 Light chain VR

<400> SEQUENCE: 47

Met Lys Leu Pro Val Arg Leu Leu Val Leu Met Phe Trp Ile Pro Ala
 1                   5                  10                  15

Ser Ser Ser Asp Val Val Met Thr Gln Thr Pro Leu Ser Leu Pro Val
                 20                  25                  30

Ser Leu Gly Asp Glu Ala Ser Ile Ser Cys Arg Ser Ser Arg Ser Leu
                 35                  40                  45

Ile His Ser Asn Gly His Thr Phe Leu Asp Trp Tyr Leu Gln Lys Pro
         50                  55                  60

Gly Gln Ser Pro Lys Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Leu Gly Val Tyr Phe Cys
                100                 105                 110

Ala Gln Ser Thr His Ala Pro Leu Leu Thr Phe Gly Ala Gly Thr Lys
                115                 120                 125

Leu Glu Leu Lys Arg Ala Asp Ala Ala Pro Thr Val Ser Ile Phe Pro
130                 135                 140

Pro Ser Ser Glu Gln Leu Thr Ser Gly Gly
145                 150

<210> SEQ ID NO 48

```
<211> LENGTH: 16
<212> TYPE: PRT
<213> ORGANISM: Artificial
<220> FEATURE:
<223> OTHER INFORMATION: W11 Light chain CDR1

<400> SEQUENCE: 48

Arg Ser Ser Arg Ser Leu Ile His Ser Asn Gly His Thr Phe Leu Asp
1               5                   10                  15

<210> SEQ ID NO 49
<211> LENGTH: 7
<212> TYPE: PRT
<213> ORGANISM: Artificial
<220> FEATURE:
<223> OTHER INFORMATION: W11 Light chain CDR2

<400> SEQUENCE: 49

Lys Val Ser Asn Arg Phe Ser
1               5

<210> SEQ ID NO 50
<211> LENGTH: 8
<212> TYPE: PRT
<213> ORGANISM: Artificial
<220> FEATURE:
<223> OTHER INFORMATION: W11 Light chain CDR3

<400> SEQUENCE: 50

Ala Gln Ser Thr His Ala Pro Leu
1               5

<210> SEQ ID NO 51
<211> LENGTH: 1437
<212> TYPE: DNA
<213> ORGANISM: Artificial
<220> FEATURE:
<223> OTHER INFORMATION: W27 Heavy chain IGHV14-2 - IGHD1-1 -IGHJ2

<400> SEQUENCE: 51
atgaaatgca gctggatcat cttcttcctg atggcagtgg ttacagggt caattcagag      60 gttcagctgc agcagtctgg gtcagagctt gtgaagtctg ggcctcagt caagttgtcc     120 tgcacagttt ctgggttcaa ctttacagac tactatatac actgggtgag gcagaggact    180
gaacagggcc tggaatggat tggaaggatt gatcctgaga tgatgaaac tacatatgcc     240 ccgaaattcc agggcaaggc cactatgaca gcagacacat cttccaacac agcctacctg    300
cagctcacca gcctgacatc tgaagacact gccgtctatt actgtgctag atctacggtc    360
cttgactact ggggccacgg caccactctc acagtctcct cagagtctgc gagaaatccc    420
accatctacc cactgacact cccacgagct ctgtcaagtg acccagtgat aatcggctgc    480
ctgattcacg attacttccc ttccggcacg atgaatgtga cctggggaaa gagtgggaag    540
gatataacca ccgtaaactt cccacctgcc ctggcctctg gggagggta ccatgagc      600 agccagttga ccctgccagc tgtcgagtgc ccagaaggag aatccgtgaa atgttccgtg    660
caacatgact ctaacgccgt ccaagaattg gatgtgaagt gctctggtcc tcctcctcct    720
tgtcctcctt gtcctccttc ctgccatccc agcctgtcac tgcagcggcc agctcttgag    780
gacctgctcc tgggttcaga tgccagcctc acatgtactc tgaatggcct gagaaatcct    840
gagggagctg tcttcacctg ggagccctcc actgggaagg atgcagtgca agaaaagct    900 gtgcagaatt cctgcggctg ctacagtgtg tccagcgtcc tgcctggctg tgctgagcgc    960
```

| | |
|---|---|
| tggaacagtg gcgcatcatt caagtgcaca gttacccatc ctgagtctga caccttaact | 1020 |
| ggcacaattg ccaaaatcac agtgaacacc ttcccacccc aggtccacct gctaccgccg | 1080 |
| ccgtcggagg agctggccct gaatgagctc gtgtccctga catgcctggt gcgagctttc | 1140 |
| aaccctaaag aagtgctggt gcgatggctg catggaaatg aggagctgtc ccagaaagc | 1200 |
| tacctagtgt ttgagcccct aaaggagcca ggcgagggag ccaccaccta cctggtgaca | 1260 |
| agcgtgttgc gtgtatcagc tgaactctgg aaacagggtg accagtactc ctgcatggtg | 1320 |
| ggccacgagg ccttgcccat gaacttcacc cagaagacca tcgaccgtct gtcgggtaaa | 1380 |
| cccaccaatg tcagcgtgtc tgtgatcatg tcagagggag atggcatctg ctactga | 1437 |

<210> SEQ ID NO 52
<211> LENGTH: 717
<212> TYPE: DNA
<213> ORGANISM: Artificial
<220> FEATURE:
<223> OTHER INFORMATION: W27 Light chain IGKV1-117-IGKJ1

<400> SEQUENCE: 52

| | |
|---|---|
| atgaagttgc ctgttaggct gttggtgctg atgttctgga ttcctggatt cagcagtgat | 60 |
| gttttgatga cccaaactcc actctccctg cctgtcagtc ttggagatca agcctccatc | 120 |
| tcttgtagag ctagtcagag cattgtacac actaatggga cacctattt agaatggtac | 180 |
| ctgcagaaac caggccagtc tccaaagctc ctgatctaca agtttccaa ccgattttct | 240 |
| ggggtcccag acaggttcag tggcagtgga tctgggacag atttcatact caagatcagc | 300 |
| agagtggagg ctgaggatct gggagtttat tactgctttc aaggttcaca tgttcctccg | 360 |
| acgttcggtg gaggcaccaa gctggaagtc aaacgggctg atgctgcacc aactgtatcc | 420 |
| atcttcccac catccagtga gcagttaaca tctggaggtg cctcagtcgt gtgcttcttg | 480 |
| aacaacttct accccaaaga catcaatgtc aagtggaaga ttgatggcag tgaacgacaa | 540 |
| aatggcgtcc tgaacagttg gactgatcag gacagcaaag acagcaccta cagcatgagc | 600 |
| agcacccta cgttgaccaa ggacgagtat gaacgacata cagctatac ctgtgaggcc | 660 |
| actcacaaga catcaacttc acccattgtc aagagcttca acaggaatga gtgttag | 717 |

<210> SEQ ID NO 53
<211> LENGTH: 1494
<212> TYPE: DNA
<213> ORGANISM: Artificial
<220> FEATURE:
<223> OTHER INFORMATION: W30 Heavy chain IGHV1-19 - IGHD2-3 - IGHJ2

<400> SEQUENCE: 53

| | |
|---|---|
| atgtcctctc cacagacact gaacacactg actctaacca tgggatggaa ctggatctttt | 60 |
| ctcttcctcc tgtcaggaac tgcaggtgtc cactctgagg tccagctgca acagtctgga | 120 |
| cctgtgctgg tgaagcctgg ggcttcagtg aagatgtcct gtaaggcttc tggatacaca | 180 |
| ttcactgact actttttgaa ctggataaaa cagagccatg gaaagagcct tgagttgatt | 240 |
| ggagttatta atcctacaa cgatggtgtt acctataacc ggaaattcaa gggcaaggcc | 300 |
| acattgactt tgacaagtc ctccagcaca gcctacatgg agctcaccag cctgacatct | 360 |
| ggggactctg cagtctatta ctgtgcaaga tctggggatg gtttctacct gtactacttt | 420 |
| gactactggg gccaaggcac cactctcaca gtctcctcag agtctgcgag aaatccacc | 480 |
| atctacccac tgacactccc acgagctctg tcaagtgacc cagtgataat cggctgcctg | 540 |
| attcacgatt acttcccttc cggcacgatg aatgtgacct ggggaaagag tgggaaggat | 600 |

```
ataaccaccg taaacttccc acctgccctg gcctctgggg gagggtacac catgagcagc    660
cagttgaccc tgccagctgt cgagtgccca aaggagaat ccgtgaaatg ttccgtgcaa    720
catgactcta acgccgtcca agaattggat gtgaagtgct ctggtcctcc tcctccttgt    780
cctccttgtc ctccttcctg ccatcccagc ctgtcactgc agcggccagc tcttgaggac    840
ctgctcctgg gttcagatgc cagcctcaca tgtactctga atggcctgag aaatcctgag    900
ggagctgtct tcacctggga gccctccact gggaaggatg cagtgcagaa gaaagctgtg    960
cagaattcct gcggctgcta cagtgtgtcc agcgtcctgc ctggctgtgc tgagcgctgg   1020
aacagtggcg catcattcaa gtgcacagtt acccatcctg agtctgacac cttaactggc   1080
acaattgcca aaatcacagt gaacaccttc ccaccccagg tccacctgct accgccgccg   1140
tcggaggagc tggccctgaa tgagctcgtg tccctgacat gctggtgcg agctttcaac    1200 cctaaagaag tgctggtgcg atggctgcat ggaaatgagg agctgtcccc agaaagctac   1260
ctagtgtttg agcccctaaa ggagccaggc gagggagcca ccacctacct ggtgacaagc   1320
gtgttgcgtg tatcagctga actctggaaa cagggtgacc agtactcctg catggtgggc   1380
cacgaggcct tgcccatgaa cttcacccag aagaccatcg accgtctgtc gggtaaaccc   1440
accaatgtca gcgtgtctgt gatcatgtca gagggagatg catctgcta ctga          1494
```

<210> SEQ ID NO 54
<211> LENGTH: 705
<212> TYPE: DNA
<213> ORGANISM: Artificial
<220> FEATURE:
<223> OTHER INFORMATION: W30 Light chain IGKV5-43-IGKJ1

<400> SEQUENCE: 54

```
atggttttca cacctcagat acttggactt atgctttttt ggatttcagc ctccagaggt     60
gaaattgtac taactcagtc tccagtcacc ctgtctgtga ctccaggaga taacgtcagt    120
ctttcctgca gggccagcca gagtattagc tacaacctac actggtttca acaaaaatca    180
catgagtctc caaggcttct catcaagttt gcttcccagt ccatctctgg gatcccctcc    240
agattcaggg gctatggatc aggaacagat ttcactctca gtatcaacag tgtggagact    300
gaagattttg gaatgtattt ctgtcaacag agtaacagct ggcctcagac gttcggtgga    360
ggcaccaagc tggaaataaa acgggctgat gctgcaccaa ctgtatccat cttcccacca    420
tccagtgagc agttaacatc tggaggtgcc tcagtcgtgt gcttcttgaa caacttctac    480
cccaaagaca tcaatgtcaa gtggaagatt gatggcagtg aacgacaaaa tggcgtcctg    540
aacagttgga ctgatcagga cagcaaagac agcacctaca gcatgagcag caccctcacg    600
ttgaccaagg acgagtatga acgacataac agctatacct gtgaggccac tcacaagaca    660
tcaacttcac ccattgtcaa gagcttcaac aggaatgagt gttag                    705
```

<210> SEQ ID NO 55
<211> LENGTH: 1449
<212> TYPE: DNA
<213> ORGANISM: Artificial
<220> FEATURE:
<223> OTHER INFORMATION: W34 Heavy chain IGHV3-1 - IGHD1-1 - IGHJ4

<400> SEQUENCE: 55

```
atgagcgtgc tgattctttt gtggctgttc acagcctttc ctggtatcct gtctgatgtg     60
cagcttcagg agtcaggacc tggcatggtg aaaccttctc agtcactttc cctcacctgc    120
```

```
accgtcacag gctactccat caccagcggt tatgactggc actggatccg acattttcca      180
ggaaacaaac tggagtggat gggctacata agttacagtg gtagcactga ctataatcca      240
gccctcagaa gtcgaatctc catcactcgt gacacatcta cgaatcattt cttcctgaag      300
gtgaattctg tgactactga agatacagcc acatattact gtgcaagaga cggctacggt      360
agtaactatg ttatggccta ctggggtcaa ggaacctcgg tcaccgtctc ctcagagtct      420
gcgagaaatc ccaccatcta cccactgaca ctcccacgag ctctgtcaag tgacccagtg      480
ataatcggct gcctgattca cgattacttc ccttccggca cgatgaatgt gacctgggga      540
aagagtggga aggatataac caccgtaaac ttcccacctg ccctggcctc tggggggagg      600
tacaccatga gcagccagtt gaccctgcca gctgtcgagt gcccagaagg agaatccgtg      660
aaatgttccg tgcaacatga ctctaacgcc gtccaagaat tggatgtgaa gtgctctggt      720
cctcctcctc cttgtcctcc ttgtcctcct tcctgccatc ccagcctgtc actgcagcgg      780
ccagctcttg aggacctgct cctgggttca gatgccagcc tcacatgtac tctgaatggc      840
ctgagaaatc ctgagggagc tgtcttcacc tgggagccct ccactgggaa ggatgcagtg      900
cagaagaaag ctgtgcagaa ttcctgcggc tgctacagtg tgtccagcgt cctgcctggc      960
tgtgctgagc gctggaacag tggcgcatca ttcaagtgca cagttaccca tcctgagtct     1020
gacaccttaa ctggcacaat tgccaaaatc acagtgaaca ccttcccacc ccaggtccac     1080
ctgctaccgc cgccgtcgga ggagctgcc ctgaatgagc tcgtgtccct gacatgcctg     1140
gtgcgagctt tcaaccctaa agaagtgctg gtgcgatggc tgcatggaaa tgaggagctg     1200
tccccagaaa gctacctagt gtttgagccc ctaaaggagc aggcgagggg agccaccacc     1260
tacctggtga caagcgtgtt gcgtgtatca gctgaactct ggaaacaggg tgaccagtac     1320
tcctgcatgg tgggccacga ggccttgccc atgaacttca cccagaagac catcgaccgt     1380
ctgtcgggta acccaccaa tgtcagcgtg tctgtgatca tgtcagaggg agatggcatc     1440
tgctactga                                                              1449

<210> SEQ ID NO 56
<211> LENGTH: 708
<212> TYPE: DNA
<213> ORGANISM: Artificial
<220> FEATURE:
<223> OTHER INFORMATION: W34 Light chain IGKV4-57-IGKJ5

<400> SEQUENCE: 56
atgcattttc aagtgcagat tttcagcttc ctgctaatca gtgcctcagt cataatgtcc       60
agaggacaaa ttgttctcac ccagtctcca gcaatcatgt ctgcatctcc aggggagaag      120
gtcaccataa cctgcagtgc cagctcaagt gtacattaca tacactggtt ccagctgaaa      180
ccaggcactt ctcccaaact ctggatttat agcacatcca acctggcttc tggagtccct      240
gctcgcttca gtggcagtgg atctgggacc tcttactctc tcacaatcag ccgaatggag      300
gctgaagatg ctgccactta ttactgtcag caaaggagta gttacccact cacgttcggt      360
gctgggacca agctggagct gaaacgggct gatgctgcac caactgtatc catcttccca      420
ccatccagtg agcagttaac atctggaggt gcctcagtcg tgtgcttctt gaacaacttc      480
taccccaaag acatcaatgt caagtggaag attgatggca gtgaacgaca aaatggcgtc      540
ctgaacagtt ggactgatca ggacagcaaa gacagcacct acagcatgag cagcaccctc      600
acgttgacca aggacgagta tgaacgacat aacagctata cctgtgaggc cactcacaag      660
acatcaactt cacccattgt caagagcttc aacaggaatg agtgttag               708
```

<210> SEQ ID NO 57
<211> LENGTH: 1491
<212> TYPE: DNA
<213> ORGANISM: Artificial
<220> FEATURE:
<223> OTHER INFORMATION: W43 Heavy chain IGHV1-22 - IGHD2-1 - IGHJ2

<400> SEQUENCE: 57

```
atgtcctctc ctcagacact gaacacactg actctaacca tgggatggag ctggatcttt      60
ctctttctcc tgtcagaagc tgcaggtgtc ctctctgagg tccagctgca acagtctgga     120
cctgaactgg tgaagcctgg gcttcagtg aagatgtcct gcaaggcttc tggatacaca     180
ttcactgact acaacatgca ctgggtgaag cagagccatg gaaagagcct tgagtggatt     240
ggatatatta acctttacaa tgatggtact gattacagcc agaagttcga gggcaggtcc     300
acattgactt aaacaagtc ctccaacaca gcctacatgg agctccgcag cctgacatcg     360
gaggattctg cagtctatta ctgtgcacga gactatggta acttcgcgta cttctttgac     420
tactggggcc aaggcaccac tctcacagtc tcctcagagt ctgcgagaaa tcccaccatc     480
taccactga cactcccacg agctctgtca agtgacccag tgataatcgg ctgcctgatt     540
cacgattact ccccttccgg cacgatgaat gtgacctggg aaagagtgg aaggatata     600
accaccgtaa acttcccacc tgccctggcc tctggggag gtacaccat gagcagccag     660
ttgaccctgc cagctgtcga gtcccagaa ggagaatccg tgaaatgttc cgtgcaacat     720
gactctaacg ccgtccaaga attggatgtg aagtgctctg gtcctcctcc tccttgtcct     780
ccttgtcctc cttcctgcca tcccagcctg tcactgcagc ggccagctct tgaggacctg     840
ctcctgggtt cagatgccag cctcacatgt actctgaatg gcctgagaaa tcctgaggga     900
gctgtcttca cctgggagcc ctccactggg aaggatgcag tgcagaagaa agctgtgcag     960
aattcctgcg gctgctacag tgtgtccagc gtcctgcctg gctgtgctga gcgctggaac    1020
agtggcgcat cattcaagtg cacagttacc catcctgagt ctgacacctt aactggcaca    1080
attgccaaaa tcacagtgaa caccttccca ccccaggtcc acctgctacc gccgccgtcg    1140
gaggagctgg ccctgaatga gctcgtgtcc ctgacatgcc tggtgcgagc tttcaaccct    1200
aaagaagtgc tggtgcgatg gctgcatgga aatgaggagc tgtccccaga aagctaccta    1260
gtgtttgagc ccctaaagga gccaggcgag ggagccacca cctacctggt gacaagcgtg    1320
ttgcgtgtat cagctgaact ctggaaacag ggtgaccagt actcctgcat ggtgggccac    1380
gaggccttgc ccatgaactt cacccagaag accatcgacc gtcgtcgggg taaacccacc    1440
aatgtcagcg tgtctgtgat catgtcagag ggagatggca tctgctactg a              1491
```

<210> SEQ ID NO 58
<211> LENGTH: 711
<212> TYPE: DNA
<213> ORGANISM: Artificial
<220> FEATURE:
<223> OTHER INFORMATION: W43 Light chain IGKV17-127-IGKJ5

<400> SEQUENCE: 58

```
atgaccatgc tctcactagc tcctctcctc agccttcttc cctctgtgt ctctgattct       60
agggcagaaa caactgtgac ccagtctcca gcatccctgt ccgtggctac aggagaaaaa     120
gtcactatca gatgcataac cagcactgat attgatgatg atatgaactg gttccaacag     180
aggccagggg aacctcctaa actccttatt tcagaaggca atgttcttcg tcctggagtc     240
```

```
ccatcccgat tctccagcag tggctatggc acagattttg ttttacaat tgaagacacg      300 ctctcagaag atgttgcaga ttattattgt ttacaaagtg ataacatgcc tctctcgttc      360
ggtgctggga ccaagctgga gctgaaacgg gctgatgctg caccaactgt atccatcttc      420
ccaccatcca gtgagcagtt aacatctgga ggtgcctcag tcgtgtgctt cttgaacaac      480
ttctacccca aagacatcaa tgtcaagtgg aagattgatg gcagtgaacg acaaaatggc      540
gtcctgaaca gttggactga tcaggacagc aaagacagca cctacagcat gagcagcacc      600
ctcacgttga ccaaggacga gtatgaacga cataacagct atacctgtga ggccactcac      660
aagacatcaa cttcacccat tgtcaagagc ttcaacagga atgagtgtta g              711
```

<210> SEQ ID NO 59
<211> LENGTH: 1446
<212> TYPE: DNA
<213> ORGANISM: Artificial
<220> FEATURE:
<223> OTHER INFORMATION: W11 Heavy chain IGHV2-2 - IGHD2-3 - IGHJ2

<400> SEQUENCE: 59

```
atggctgtct tggggctgct cttctgcctg gtgacattcc caagctgtgt cctatcccag      60
gtgcagctga agcagtcagg acctggccta gtgcagccct cacagagcct gtccatcacc     120
tgcacggtct ctggtttctc attaactaac tatggtgtac actggattcg ccagtctcca     180
ggaaagggtc tggaatggct gggagtgata tggagtggtg aagaatagac tataatgca      240 gctttcatat ccagactgaa catcaacaag gacaattcca agagccaagt tttcttaaa      300 atgaacagtc tacaaactga tgacacagcc atatactact gtgccaggac ttatgatggt     360
tactacttct ttcaatactg gggccaaggc accctctca cagtctcctc agagtctgcg      420
agaaatccca ccatctaccc actgacactc ccacgagctc tgtcaagtga cccagtgata     480
atcggctgcc tgattcacga ttacttccct tccggcacga tgaatgtgac ctggggaaag     540
agtgggaagg atataaccac cgtaaacttc ccacctgccc tggcctctgg ggagggtac      600 accatgagca gccagttgac cctgccagct gtcgagtgcc agaaggaga tccgtgaaa      660 tgttccgtgc aacatgactc taacgccgtc aagaattgg atgtgaagtg ctctggtcct      720
cctcctcctt gtcctccttg tcctccttcc tgccatccca gcctgtcact gcagcggcca     780
gctcttgagg acctgctcct gggttcagat gccagcctca catgtactct gaatggcctg     840
agaaatcctg agggagctgt cttcacctgg gagccctcca ctgggaagga tgcagtgcag     900
aagaaagctg tgcagaattc ctgcggctgc tacagtgtgt ccagcgtcct gcctggctgt     960
gctgagcgct ggaacagtgg cgcatcattc aagtgcacag ttacccatcc tgagtctgac    1020 acctaactg gcacaattgc caaaatcaca gtgaacacct tcccacccca ggtccacctg    1080
ctaccgccgc cgtcggagga gctggccctg aatgagctcg tgtccctgac atgcctggtg    1140
cgagctttca accctaaaga agtgctggtc gatggctgc atggaaatga ggagctgtcc    1200
ccagaaagct acctagtgtt tgagcccta aaggagccag cgagggagc caccacctac    1260 ctggtgacaa gcgtgttgcg tgtatcagct gaactctgga acagggtga ccagtactcc    1320 tgcatggtgg gccacgaggc cttgcccatg aacttcaccc agaagaccat cgaccgtctg    1380
tcgggtaaac ccaccaatgt cagcgtgtct gtgatcatgt cagaggga tggcatctgc     1440 tactga                                                               1446
```

<210> SEQ ID NO 60
<211> LENGTH: 720

<212> TYPE: DNA
<213> ORGANISM: Artificial
<220> FEATURE:
<223> OTHER INFORMATION: W11 Light chain IGKV1-110-IGKJ5

<400> SEQUENCE: 60

| | | | | | |
|---|---|---|---|---|---|
| atgaagttgc | ctgttaggct | gttggtgctg | atgttctgga | ttcctgcttc | cagcagtgat | 60 |
| gttgtgatga | cccaaactcc | actctccctg | cctgtcagtc | ttggagatga | agcctccatc | 120 |
| tcttgcagat | ctagtcggag | ccttatacac | agtaatggac | acaccttctt | agattggtac | 180 |
| ctgcagaagc | caggccagtc | tccaaagctc | ctcatctaca | agtttcgaa | ccgattttct | 240 |
| ggggtcccag | acaggttcag | tggcagtgga | tcagggacag | atttcacact | caagatcagc | 300 |
| agagtggagg | ctgaggatct | gggagtttat | ttctgcgctc | aaagtacaca | tgctcctctg | 360 |
| ctcacgttcg | gtgctgggac | caagctggag | ctgaaacggg | ctgatgctgc | accaactgta | 420 |
| tccatcttcc | caccatccag | tgagcagtta | acatctggag | gtgcctcagt | cgtgtgcttc | 480 |
| ttgaacaact | tctaccccaa | agacatcaat | gtcaagtgga | agattgatgg | cagtgaacga | 540 |
| caaaatggcg | tcctgaacag | ttggactgat | caggacagca | agacagcac | ctacagcatg | 600 |
| agcagcaccc | tcacgttgac | caaggacgag | tatgaacgac | ataacagcta | tacctgtgag | 660 |
| gccactcaca | agacatcaac | ttcacccatt | gtcaagagct | caacaggaa | tgagtgttag | 720 |

<210> SEQ ID NO 61
<211> LENGTH: 17
<212> TYPE: DNA
<213> ORGANISM: Artificial
<220> FEATURE:
<223> OTHER INFORMATION: Primer MH1
<220> FEATURE:
<221> NAME/KEY: misc_feature
<222> LOCATION: (6)..(6)
<223> OTHER INFORMATION: n is a, c, g, or t

<400> SEQUENCE: 61
sargtnmagc tgsagtc                                                  17

<210> SEQ ID NO 62
<211> LENGTH: 23
<212> TYPE: DNA
<213> ORGANISM: Artificial
<220> FEATURE:
<223> OTHER INFORMATION: Primer MH2
<220> FEATURE:
<221> NAME/KEY: misc_feature
<222> LOCATION: (6)..(6)
<223> OTHER INFORMATION: n is a, c, g, or t

<400> SEQUENCE: 62
sargtnmagc tgsagsagtc wgg                                           23

<210> SEQ ID NO 63
<211> LENGTH: 21
<212> TYPE: DNA
<213> ORGANISM: Artificial
<220> FEATURE:
<223> OTHER INFORMATION: Primer MH3

<400> SEQUENCE: 63
caggttactc tgaaagwtst g                                             21

<210> SEQ ID NO 64
<211> LENGTH: 20
<212> TYPE: DNA

```
<213> ORGANISM: Artificial
<220> FEATURE:
<223> OTHER INFORMATION: Primer MH4

<400> SEQUENCE: 64
gaggtccarc tgcaacartc                                              20

<210> SEQ ID NO 65
<211> LENGTH: 20
<212> TYPE: DNA
<213> ORGANISM: Artificial
<220> FEATURE:
<223> OTHER INFORMATION: Primer MH5

<400> SEQUENCE: 65
caggtccaac tvcagcarcc                                              20

<210> SEQ ID NO 66
<211> LENGTH: 20
<212> TYPE: DNA
<213> ORGANISM: Artificial
<220> FEATURE:
<223> OTHER INFORMATION: Primer MH6

<400> SEQUENCE: 66
gaggtgaass tggtggaatc                                              20

<210> SEQ ID NO 67
<211> LENGTH: 20
<212> TYPE: DNA
<213> ORGANISM: Artificial
<220> FEATURE:
<223> OTHER INFORMATION: Primer MH7

<400> SEQUENCE: 67
gatgtgaact tggaagtgtc                                              20

<210> SEQ ID NO 68
<211> LENGTH: 22
<212> TYPE: DNA
<213> ORGANISM: Artificial
<220> FEATURE:
<223> OTHER INFORMATION: Primer IgAR

<400> SEQUENCE: 68
gatggtggga tttctcgcag ac                                           22

<210> SEQ ID NO 69
<211> LENGTH: 24
<212> TYPE: DNA
<213> ORGANISM: Artificial
<220> FEATURE:
<223> OTHER INFORMATION: Primer ECORI SCF

<400> SEQUENCE: 69
gaattcacca tgaggctcta cttg                                         24

<210> SEQ ID NO 70
<211> LENGTH: 42
<212> TYPE: DNA
<213> ORGANISM: Artificial
<220> FEATURE:
<223> OTHER INFORMATION: Primer Flag SC3R

<400> SEQUENCE: 70
ctcgagtcac ttgtcgtcat cgtctttgta gtccccggga tt                     42
```

```
<210> SEQ ID NO 71
<211> LENGTH: 616
<212> TYPE: PRT
<213> ORGANISM: Artificial
<220> FEATURE:
<223> OTHER INFORMATION: mSC3F FLAG

<400> SEQUENCE: 71

Met Arg Leu Tyr Leu Phe Thr Leu Val Thr Val Phe Ser Gly Val
1               5                   10                  15

Ser Thr Lys Ser Pro Ile Phe Gly Pro Gln Glu Val Ser Ser Ile Glu
            20                  25                  30

Gly Asp Ser Val Ser Ile Thr Cys Tyr Tyr Pro Asp Thr Ser Val Asn
        35                  40                  45

Arg His Thr Arg Lys Tyr Trp Cys Arg Gln Gly Ala Ser Gly Met Cys
    50                  55                  60

Thr Thr Leu Ile Ser Ser Asn Gly Tyr Leu Ser Lys Glu Tyr Ser Gly
65                  70                  75                  80

Arg Ala Asn Leu Ile Asn Phe Pro Glu Asn Asn Thr Phe Val Ile Asn
                85                  90                  95

Ile Glu Gln Leu Thr Gln Asp Thr Gly Ser Tyr Lys Cys Gly Leu
            100                 105                 110

Gly Thr Ser Asn Arg Gly Leu Ser Phe Asp Val Ser Leu Glu Val Ser
        115                 120                 125

Gln Val Pro Glu Leu Pro Ser Asp Thr His Val Tyr Thr Lys Asp Ile
    130                 135                 140

Gly Arg Asn Val Thr Ile Glu Cys Pro Phe Lys Arg Glu Asn Val Pro
145                 150                 155                 160

Ser Lys Lys Ser Leu Cys Lys Lys Thr Asn Gln Ser Cys Glu Leu Val
                165                 170                 175

Ile Asp Ser Thr Glu Lys Val Asn Pro Ser Tyr Ile Gly Arg Ala Lys
            180                 185                 190

Leu Phe Met Lys Gly Thr Asp Leu Thr Val Phe Tyr Val Asn Ile Ser
        195                 200                 205

His Leu Thr His Asn Asp Ala Gly Leu Tyr Ile Cys Gln Ala Gly Glu
    210                 215                 220

Gly Pro Ser Ala Asp Lys Lys Asn Val Asp Leu Gln Val Leu Ala Pro
225                 230                 235                 240

Glu Pro Glu Leu Leu Tyr Lys Asp Leu Arg Ser Ser Val Thr Phe Glu
                245                 250                 255

Cys Asp Leu Gly Arg Glu Val Ala Asn Glu Ala Lys Tyr Leu Cys Arg
            260                 265                 270

Met Asn Lys Glu Thr Cys Asp Val Ile Ile Asn Thr Leu Gly Lys Arg
        275                 280                 285

Asp Pro Asp Phe Glu Gly Arg Ile Leu Ile Thr Pro Lys Asp Asn
    290                 295                 300

Gly Arg Phe Ser Val Leu Ile Thr Gly Leu Arg Lys Glu Asp Ala Gly
305                 310                 315                 320

His Tyr Gln Cys Gly Ala His Ser Ser Gly Leu Pro Gln Glu Gly Trp
                325                 330                 335

Pro Ile Gln Thr Trp Gln Leu Phe Val Asn Glu Glu Ser Thr Ile Pro
            340                 345                 350

Asn Arg Arg Ser Val Val Lys Gly Val Thr Gly Gly Ser Val Ala Ile
        355                 360                 365
```

Ala Cys Pro Tyr Asn Pro Lys Glu Ser Ser Leu Lys Tyr Trp Cys
370                 375                 380

Arg Trp Glu Gly Asp Gly Asn Gly His Cys Pro Ala Leu Val Gly Thr
385                 390                 395                 400

Gln Ala Gln Val Gln Glu Glu Tyr Glu Gly Arg Leu Ala Leu Phe Asp
                405                 410                 415

Gln Pro Gly Asn Gly Thr Tyr Thr Val Ile Leu Asn Gln Leu Thr Thr
                420                 425                 430

Glu Asp Ala Gly Phe Tyr Trp Cys Leu Thr Asn Gly Asp Ser Arg Trp
435                 440                 445

Arg Thr Thr Ile Glu Leu Gln Val Ala Glu Ala Thr Arg Glu Pro Asn
450                 455                 460

Leu Glu Val Thr Pro Gln Asn Ala Thr Ala Val Leu Gly Glu Thr Phe
465                 470                 475                 480

Thr Val Ser Cys His Tyr Pro Cys Lys Phe Tyr Ser Gln Glu Lys Tyr
                485                 490                 495

Trp Cys Lys Trp Ser Asn Lys Gly Cys His Ile Leu Pro Ser His Asp
                500                 505                 510

Glu Gly Ala Arg Gln Ser Ser Val Ser Cys Asp Gln Ser Ser Gln Leu
                515                 520                 525

Val Ser Met Thr Leu Asn Pro Val Ser Lys Glu Asp Glu Gly Trp Tyr
                530                 535                 540

Trp Cys Gly Val Lys Gln Gly Gln Thr Tyr Gly Glu Thr Thr Ala Ile
545                 550                 555                 560

Tyr Ile Ala Val Glu Glu Arg Thr Arg Gly Ser Ser His Val Asn Pro
                565                 570                 575

Thr Asp Ala Asn Ala Arg Ala Lys Val Ala Leu Glu Glu Glu Val Val
                580                 585                 590

Asp Ser Ser Ile Ser Glu Lys Glu Asn Lys Ala Ile Pro Asn Pro Gly
                595                 600                 605

Asp Tyr Lys Asp Asp Asp Asp Lys
                610                 615

<210> SEQ ID NO 72
<211> LENGTH: 21
<212> TYPE: DNA
<213> ORGANISM: Artificial
<220> FEATURE:
<223> OTHER INFORMATION: Primer CkR

<400> SEQUENCE: 72
aacgtgaggg tgctgctcat g                                         21

<210> SEQ ID NO 73
<211> LENGTH: 32
<212> TYPE: DNA
<213> ORGANISM: Artificial
<220> FEATURE:
<223> OTHER INFORMATION: Primer deg Vk

<400> SEQUENCE: 73
ggctgcagst tcagtggcag tggrtcwggr ac                             32

<210> SEQ ID NO 74
<211> LENGTH: 417
<212> TYPE: PRT
<213> ORGANISM: Escherichia coli

<400> SEQUENCE: 74

```
Met Leu Lys Arg Glu Met Asn Ile Ala Asp Tyr Asp Ala Glu Leu Trp
1               5                   10                  15

Gln Ala Met Glu Gln Glu Lys Val Arg Gln Glu His Ile Glu Leu
            20                  25                  30

Ile Ala Ser Glu Asn Tyr Thr Ser Pro Arg Val Met Gln Ala Gln Gly
        35                  40                  45

Ser Gln Leu Thr Asn Lys Tyr Ala Glu Gly Tyr Pro Gly Lys Arg Tyr
    50                  55                  60

Tyr Gly Gly Cys Glu Tyr Val Asp Ile Val Glu Gln Leu Ala Ile Asp
65                  70                  75                  80

Arg Ala Lys Glu Leu Phe Gly Ala Asp Tyr Ala Asn Val Gln Pro His
                85                  90                  95

Ser Gly Ser Gln Ala Asn Phe Ala Val Tyr Thr Ala Leu Leu Glu Pro
            100                 105                 110

Gly Asp Thr Val Leu Gly Met Asn Leu Ala His Gly Gly His Leu Thr
        115                 120                 125

His Gly Ser Pro Val Asn Phe Ser Gly Lys Leu Tyr Asn Ile Val Pro
    130                 135                 140

Tyr Gly Ile Asp Ala Thr Gly His Ile Asp Tyr Ala Asp Leu Glu Lys
145                 150                 155                 160

Gln Ala Lys Glu His Lys Pro Lys Met Ile Ile Gly Gly Phe Ser Ala
                165                 170                 175

Tyr Ser Gly Val Val Asp Trp Ala Lys Met Arg Glu Ile Ala Asp Ser
            180                 185                 190

Ile Gly Ala Tyr Leu Phe Val Asp Met Ala His Val Ala Gly Leu Val
        195                 200                 205

Ala Ala Gly Val Tyr Pro Asn Pro Val Pro His Ala His Val Val Thr
    210                 215                 220

Thr Thr Thr His Lys Thr Leu Ala Gly Pro Arg Gly Gly Leu Ile Leu
225                 230                 235                 240

Ala Lys Gly Gly Ser Glu Glu Leu Tyr Lys Lys Leu Asn Ser Ala Val
                245                 250                 255

Phe Pro Gly Gly Gln Gly Gly Pro Leu Met His Val Ile Ala Gly Lys
            260                 265                 270

Ala Val Ala Leu Lys Glu Ala Met Glu Pro Glu Phe Lys Thr Tyr Gln
        275                 280                 285

Gln Gln Val Ala Lys Asn Ala Lys Ala Met Val Glu Val Phe Leu Glu
    290                 295                 300

Arg Gly Tyr Lys Val Val Ser Gly Gly Thr Asp Asn His Leu Phe Leu
305                 310                 315                 320

Val Asp Leu Val Asp Lys Asn Leu Thr Gly Lys Glu Ala Asp Ala Ala
                325                 330                 335

Leu Gly Arg Ala Asn Ile Thr Val Asn Lys Asn Ser Val Pro Asn Asp
            340                 345                 350

Pro Lys Ser Pro Phe Val Thr Ser Gly Ile Arg Val Gly Thr Pro Ala
        355                 360                 365

Ile Thr Arg Arg Gly Phe Lys Glu Ala Glu Ala Lys Glu Leu Ala Gly
    370                 375                 380
```

-continued

```
Trp Met Cys Asp Val Leu Asp Ser Ile Asn Asp Glu Ala Val Ile Glu
385                 390                 395                 400

Arg Ile Lys Gly Lys Val Leu Asp Ile Cys Ala Arg Tyr Pro Val Tyr
                405                 410                 415

Ala
```